United States Patent
Wynne et al.

(10) Patent No.: US 10,117,436 B2
(45) Date of Patent: Nov. 6, 2018

(54) ANTIMICROBIAL POLYMERIC COMPOSITIONS

(71) Applicant: Virginia Commonwealth University, Richmond, VA (US)

(72) Inventors: Kenneth J. Wynne, Midlothian, VA (US); Souvik Chakrabarty, Ithaca, NY (US); Wei Zhang, Midlothian, VA (US); Asima Chakravorty, Richmond, VA (US); Olufemi O. Oyesanya, Chesapeake, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 0 days.

(21) Appl. No.: 15/080,567

(22) Filed: Mar. 24, 2016

(65) Prior Publication Data
US 2017/0049109 A1 Feb. 23, 2017

Related U.S. Application Data

(63) Continuation of application No. 13/665,915, filed on Oct. 31, 2012, now abandoned.
(Continued)

(51) Int. Cl.
*A01N 55/00* (2006.01)
*C08G 65/22* (2006.01)
(Continued)

(52) U.S. Cl.
CPC ............. *A01N 55/00* (2013.01); *C07F 7/184* (2013.01); *C07F 7/1804* (2013.01);
(Continued)

(58) Field of Classification Search
None
See application file for complete search history.

(56) References Cited

U.S. PATENT DOCUMENTS 6,534,568 B1    3/2003    Katz et al.
2004/0241522 A1*    12/2004    Ono ........................ C08G 77/04
                                                               429/494

FOREIGN PATENT DOCUMENTS

WO    WO2012083011 A1    6/2012

OTHER PUBLICATIONS

Jul. 8, 2013, Kenneth J. Wynne, "Health and Safety via Surface Modification of Polyurethanes" American Chemical Society, 2013, 16, ACS Symposium Series; American Chemical Society: Washington DC, USA.
(Continued)

*Primary Examiner* — Robert A Wax
*Assistant Examiner* — Melissa S Mercier
(74) *Attorney, Agent, or Firm* — Neifeld IP Law, PC

(57) ABSTRACT

A compound having the formula:

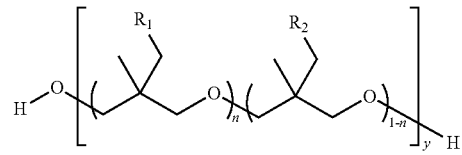

wherein n, y, $R_1$ and $R_2$ are defined herein, and others, methods of making of and using, and compositions made thereby which have an antimicrobial resistance effect are described.

20 Claims, 23 Drawing Sheets

Related U.S. Application Data

(60) Provisional application No. 61/552,452, filed on Oct. 27, 2011, provisional application No. 61/552,454, filed on Oct. 27, 2011.

(51) Int. Cl.

| | |
|---|---|
| *C08G 18/50* | (2006.01) |
| *C08G 65/336* | (2006.01) |
| *C07F 7/18* | (2006.01) |
| *C08G 18/48* | (2006.01) |
| *C08G 18/61* | (2006.01) |
| *C08G 18/66* | (2006.01) |
| *C08G 18/71* | (2006.01) |
| *C08G 18/75* | (2006.01) |
| *C09D 175/04* | (2006.01) |
| *C08G 65/18* | (2006.01) |

(52) U.S. Cl.
CPC ..... *C08G 18/4862* (2013.01); *C08G 18/5066* (2013.01); *C08G 18/61* (2013.01); *C08G 18/6674* (2013.01); *C08G 18/718* (2013.01); *C08G 18/758* (2013.01); *C08G 65/18* (2013.01); *C08G 65/22* (2013.01); *C08G 65/226* (2013.01); *C08G 65/336* (2013.01); *C09D 175/04* (2013.01); *C08G 2650/04* (2013.01); *C08G 2650/38* (2013.01); *C08G 2650/48* (2013.01); *C08G 2650/50* (2013.01); *C08G 2650/64* (2013.01)

(56) References Cited

OTHER PUBLICATIONS

Jan. 31, 2011, Souvik Chakrabarty, "Highly Effective, Water-Soluble, Hemocompatible 1,3-Propylene Oxide-Based Antimicrobials", Biomacromolecules, 2011, 12, 757-769, ACS Publications, American Chemical Society, Washington DC, USA.
Jan. 14, 2014, Allison King, "High Antimicrobial Effectiveness with Low Hemolytic and Cytotoxic Activity for PEG/Quaternary Copolyoxetanes", Biomacromolecules, 2014, 15, 456-457, ACS Publications, American Chemical Society, Washington DC, USA.
Sep. 21, 2005, Umit Makal, "Polyurethane biocidal polymeric surface modifiers" Biomaterials, 2006, 27, 1316-1326, Science Direct, Elsevier, USA.
Mar. 31, 2005, Umit Makal, "Water Induced Hydrophobic Surface", Langmuir, 2005, 21, 3742-3745, American Chemical Society, Washington DC, USA.
Mar. 28, 2007, Pinar Kurt, "Highly Effective Contact Antimicrobial Surfaces via Polymer Surface Modifiers", Langmuir, 2007, 23, 4719-4723, American Chemical Society, Washington DC, USA.
Aug. 8, 2006, Umit Makal, "Water Makes It Hydrophobic: Contraphilic Wetting for Polyurethanes with Soft Blocks Having Semifluorinated and 5,5-Dimethylhydantoin Side Chains", Langmuir, 2007, 23, 209-216, American Chemical Society, Washington DC, USA.
Apr. 30, 2008, Pinar Kurt, "Surface Characterization of Biocidal Polyurethane Modifiers Having Poly(3,3-substituted)oxetane Soft Blocks with Alkylammonium Side Chains", Langmuir, 2008, 24, 5816-5824, American Chemical Society, Washington DC, USA.
Mar. 24, 2010, Murari L. Gupta, "Quantifying Surface-Accessible Quaternary Charge for Surface Modified Coatings via Streaming Potential Measurements", Langmuir, 2010, 26, 9032-9039, American Chemical Society, Washington DC, USA.
Dec. 9, 2009, Wei Zhang, "More Fluorous Surface Modifier Makes it Less Oleophobic: Fluorinated Siloxane Copolymer/PDMS Coatings", Langmuir, 2010, 26, 5848-5855, American Chemical Society, Washington DC, USA.
Mar. 6, 2016, Congzhou Wang, "Real-Time Observation of Antimicrobial Polycation Effects on *Escherichia coli*: Adapting the Carpet Model for Membrane Disruption to Quaternary Copolyoxetanes", Langmuir, 2016, 32, 2975-2984, American Chemical Society, Washington DC, USA.
Nov. 30, 2007, Pinar Kurt, "Co-Polyoxetanes with Alkylammonium and Fluorous or PEG-Like Side Chains: Soft Blocks for Surface Modifying Polyurethanes", Macromolecules, 2007, 40, 9537-9543, American Chemical Society, Washington DC, USA.
Stephen J. Grunzinger, "Polyurethanes from novel 1,3-propyleneoxide co-telechelics having pendant hydantoin and methoxymethyl groups", Polymer, 2006, 47, 4230-4237, Science Direct, Elsevier, USA.
Jun. 10, 2017, Stephen J. Grunzinger, "Biocidal activity of hydantoin-containing polyurethane polymeric surface modifiers", Polymer, 2007, 48, 4653-4662, Science Direct, Elsevier, USA.
Aug. 28, 2012, Chakrabarty et al, "PDMS-fluorous polyoxetane-PDMS triblock hybrid elastomers: tough and transparent with novel bulk morphologies", Macromolecules, 2012, 45, p. 7900-7913. Of Record in U.S. Appl. No. 13/665,915.
Jena et al, "Novel waterborne hyperbranched polyurethane-urea-silica hybrid crosslinked coating films", PaintIndia (2011), 61(12), p. 56-62. Of Record in U.S. Appl. No. 13/665,915.
Sep. 2012, Qiu et al, "Preparation, characterization and properties of UV-curable waterborne polyurethane acrylate/SiO2 coating", J. Coat. Technol. Res., 9(5) 503-514 (Sep. 2012), Of Record in U.S. Appl. No. 13/665,915.
Wynne et al, "TM-AFM Applied to the Elucidation of Topology and Morphology of Novel Fluorous Polyurethanes", Polymer Preprints, 53(2), 5 (2012).

* cited by examiner

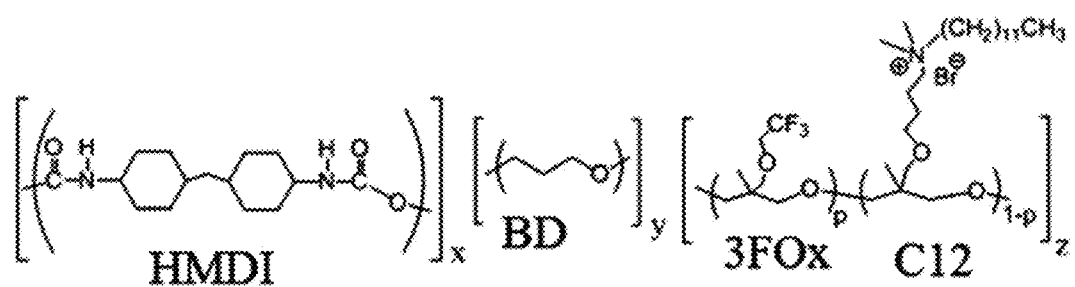
Figure 1. HMDI-BD(30)-P[(3FOx)(C12)-86:13-$M_n$]

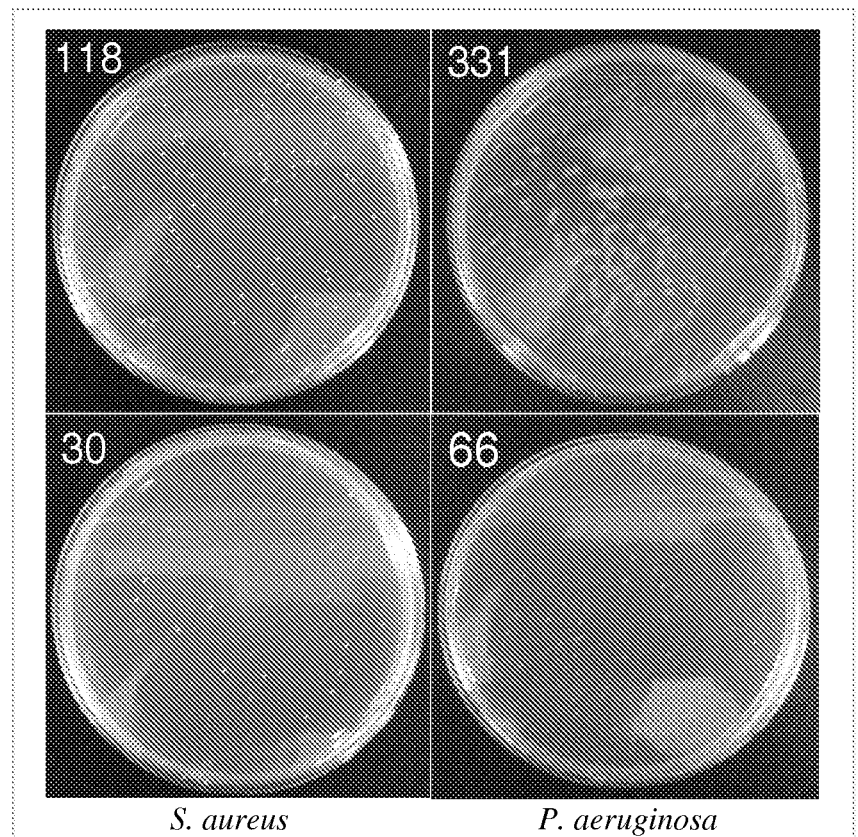
Figure 2. Biocidal tests with the 0.5% PQ-C12 modified PDMS showing the control (top) and the 0.5% (bottom) results.

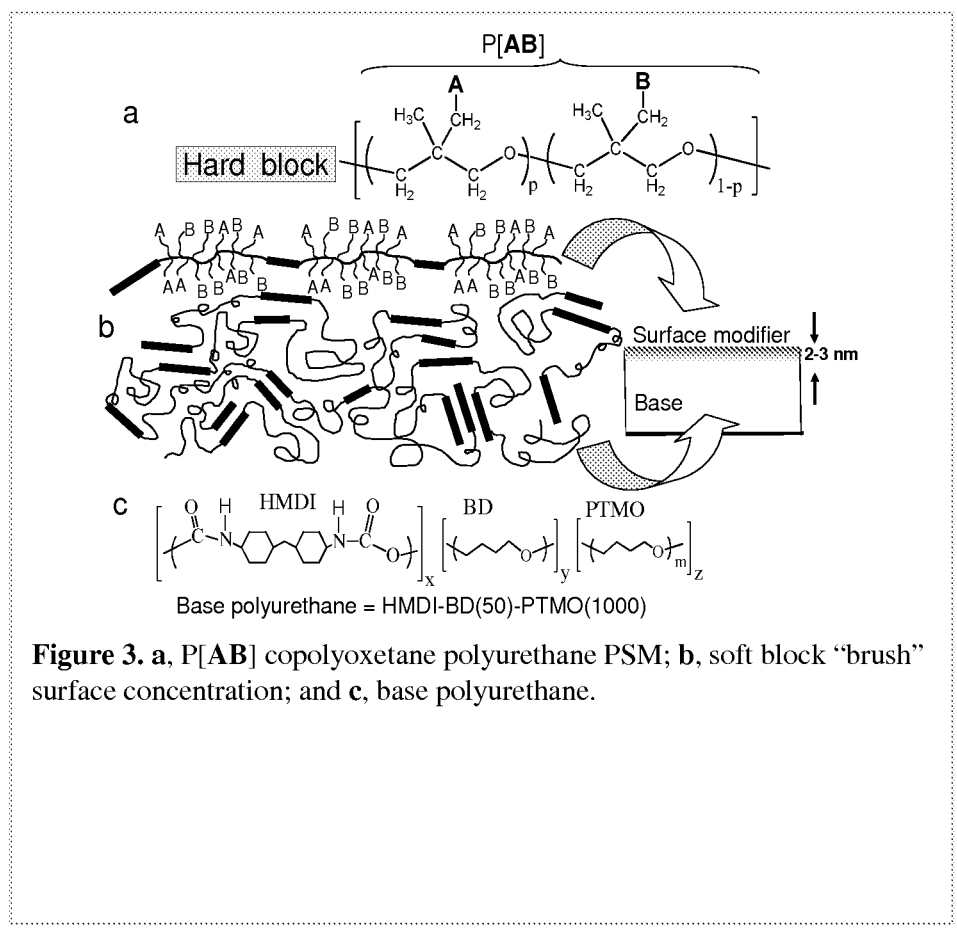
Figure 3. a, P[AB] copolyoxetane polyurethane PSM; b, soft block "brush" surface concentration; and c, base polyurethane.

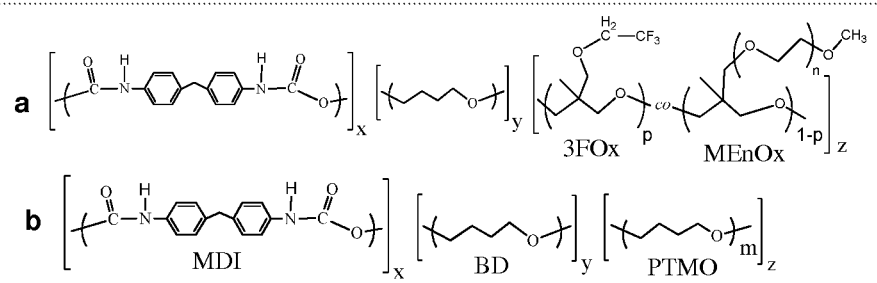
Figure 4. Components in a, PSM MDI/BD-P[(3FOx)(MEnOx)-p:(1-p)], 27-42 hard block wt%, depending on P[AB] soft block and b, base MDI/BD(36)-PTMO(2200).

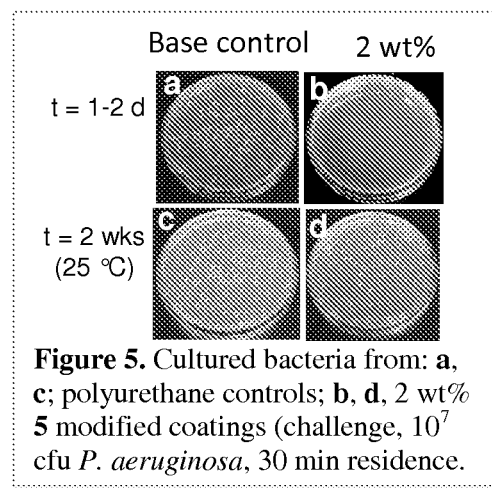
Figure 5. Cultured bacteria from: a, c; polyurethane controls; b, d, 2 wt% 5 modified coatings (challenge, $10^7$ cfu *P. aeruginosa*, 30 min residence.

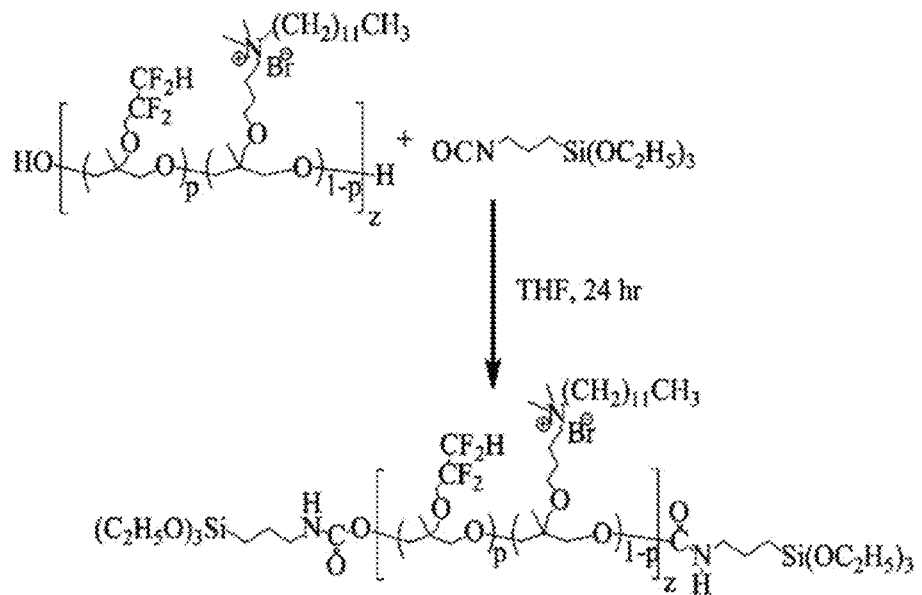

Figure 6. End-capping P[(4FOx)(C12)-64:24] diol with triethoxysilyl functionality. For this example, p = 64, 1-p = 24. The resulting end-capped P[AB] copolyoxetane is designated 9. "TES" designates triethoxysilyl (TES) end-capped. Modification of base polyurethane (Figure 2) with 1 wt% 9 and BTSE (10 wt%) resulted in antimicrobial surface functionality that effected 100% kill of sprayed-on *P. aeruginosa* ($10^6$ cfu/ml, 1 hr residence) confirming feasibility. Importantly, two weeks later 100% kill was once again realized ind

Figure 9. Antimicrobial property of the 4FOx blends with *Escherichia coli*.

Figure 10. Antimicrobial property of the 4FOx blends with *Pseudomonas aeruginosa*

Figure 11. End capping of the diol

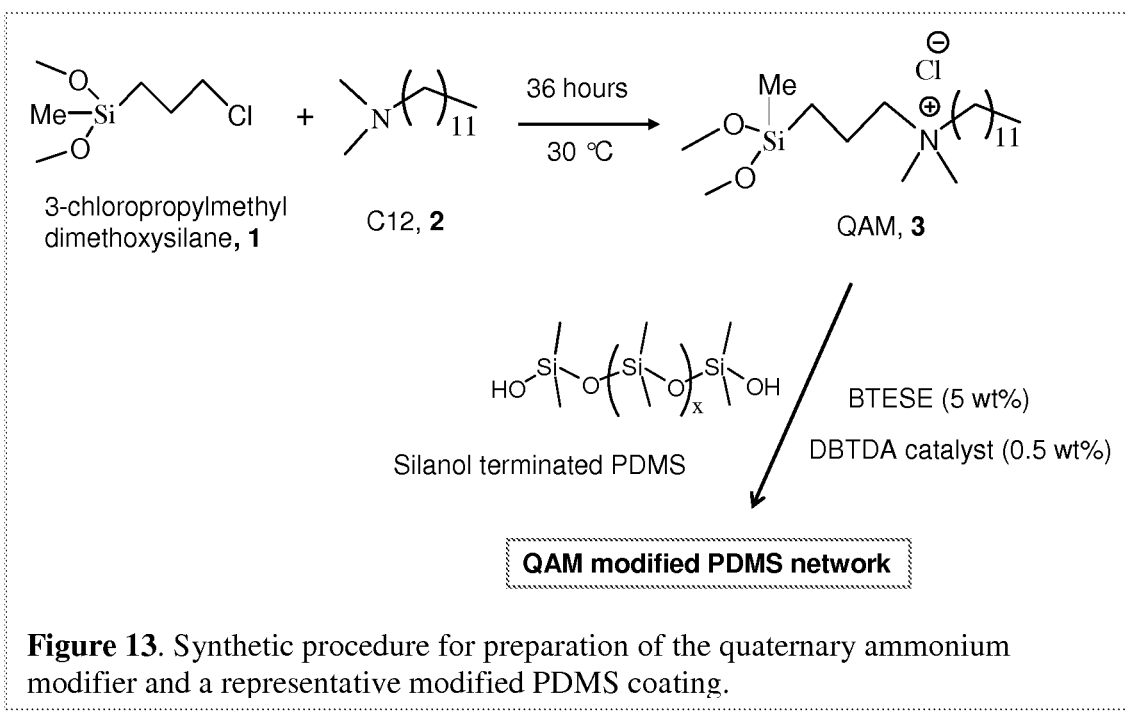
Figure 13. Synthetic procedure for preparation of the quaternary ammonium modifier and a representative modified PDMS coating.

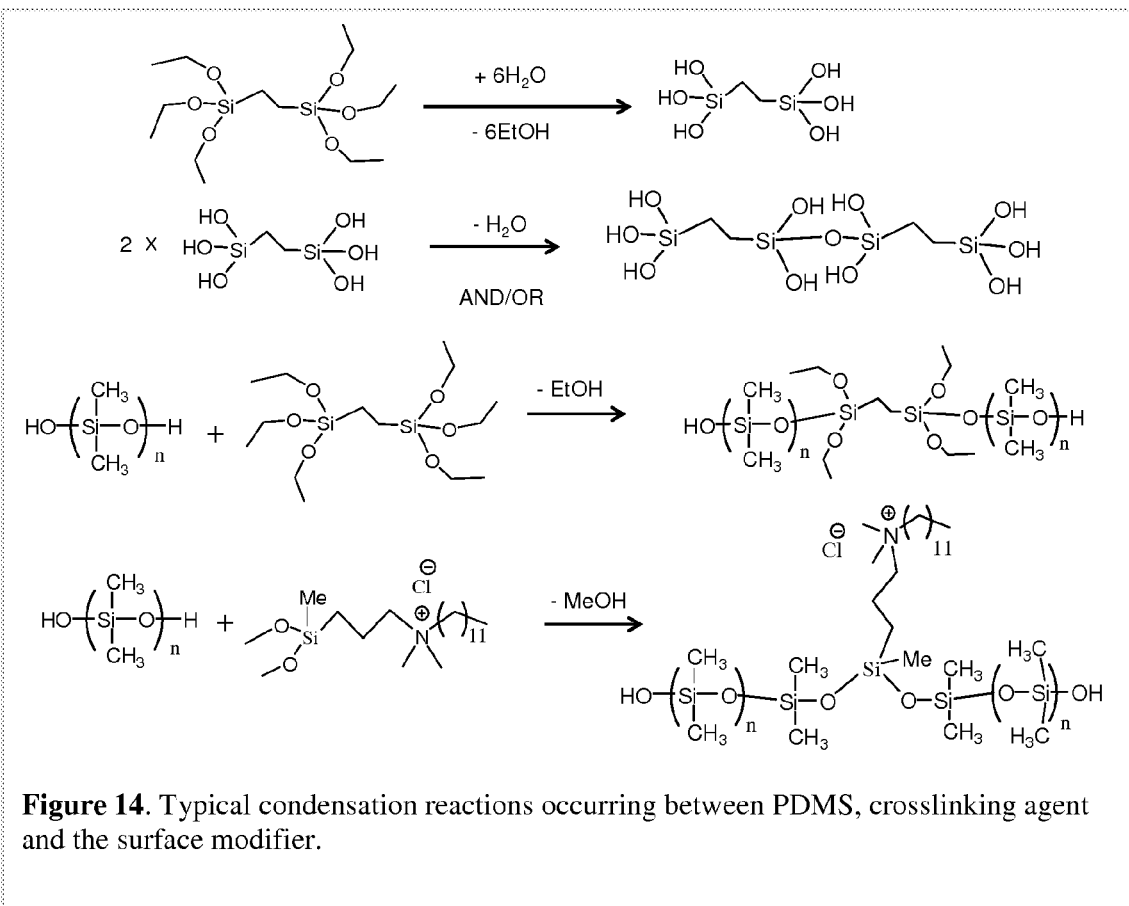
Figure 14. Typical condensation reactions occurring between PDMS, crosslinking agent and the surface modifier.

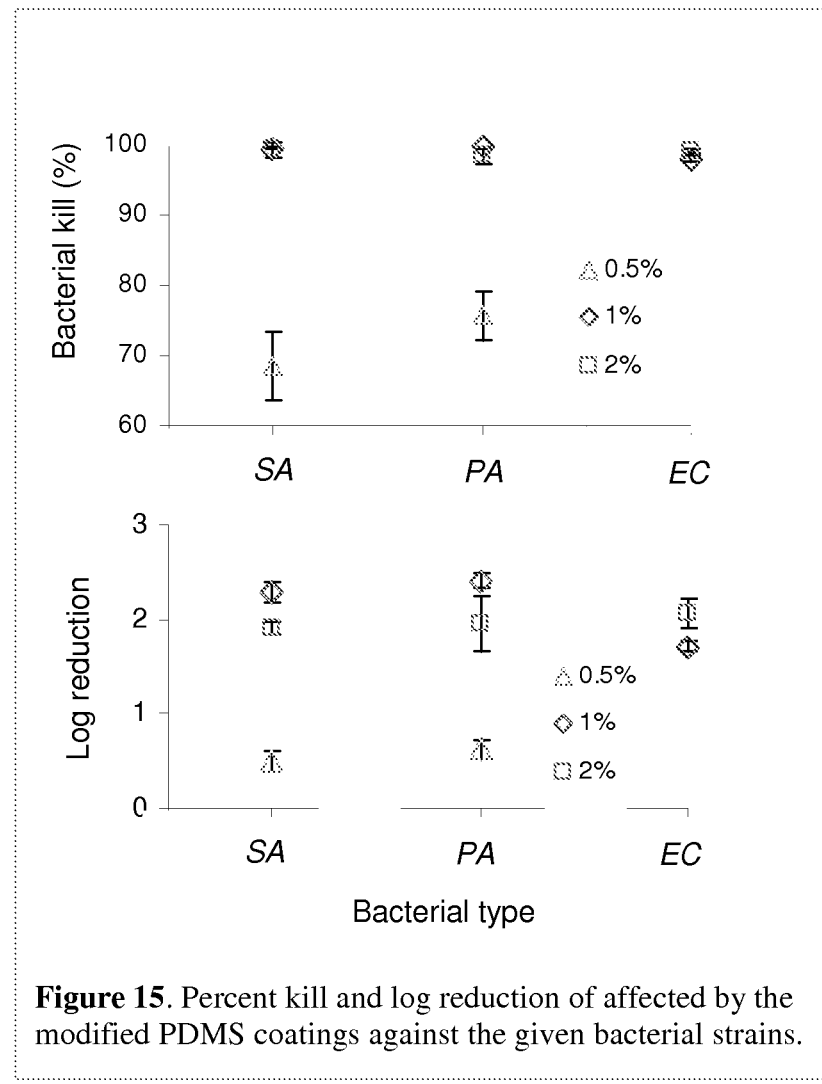
Figure 15. Percent kill and log reduction of affected by the modified PDMS coatings against the given bacterial strains.

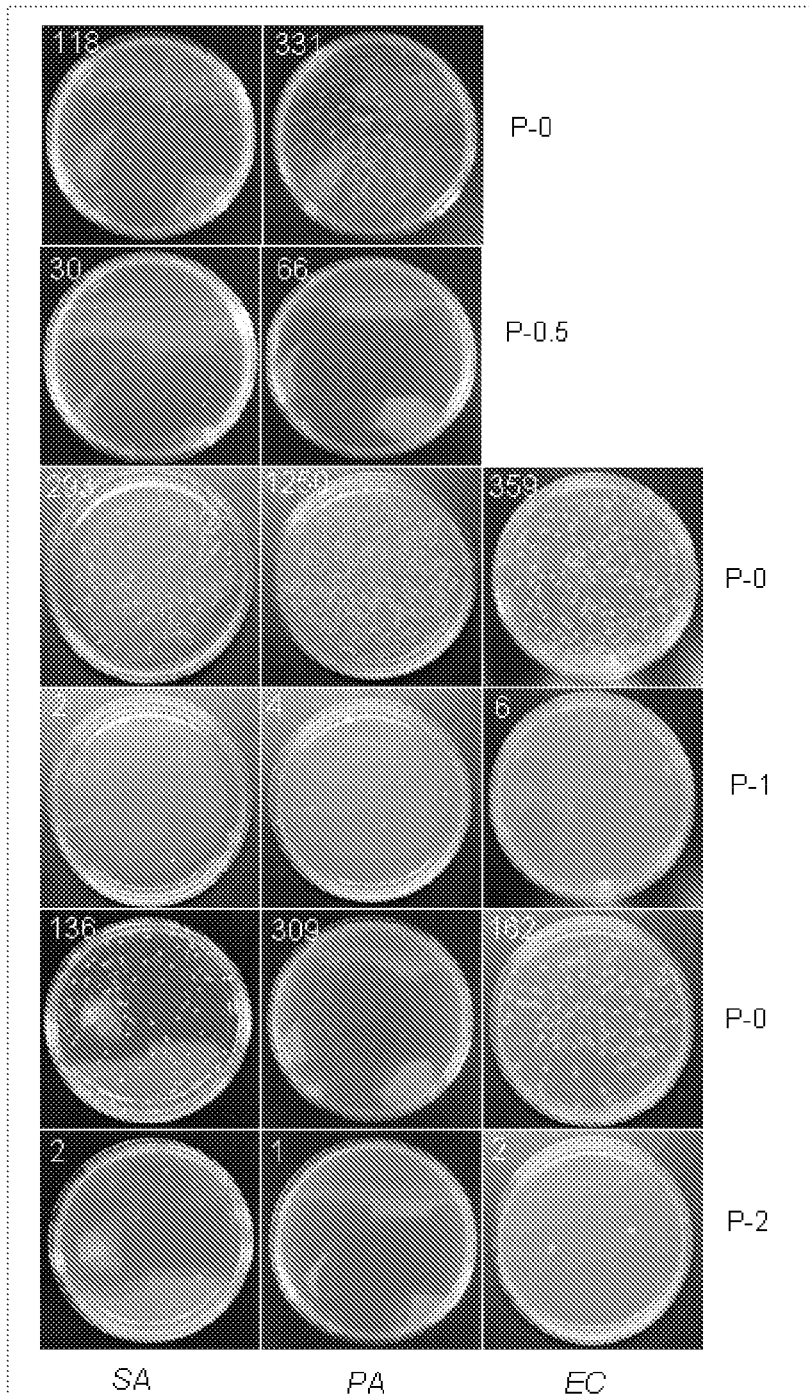
Figure 16. Representative biocidal test results showing the number of remnant CFU in the control and in the modified PDMS coatings.

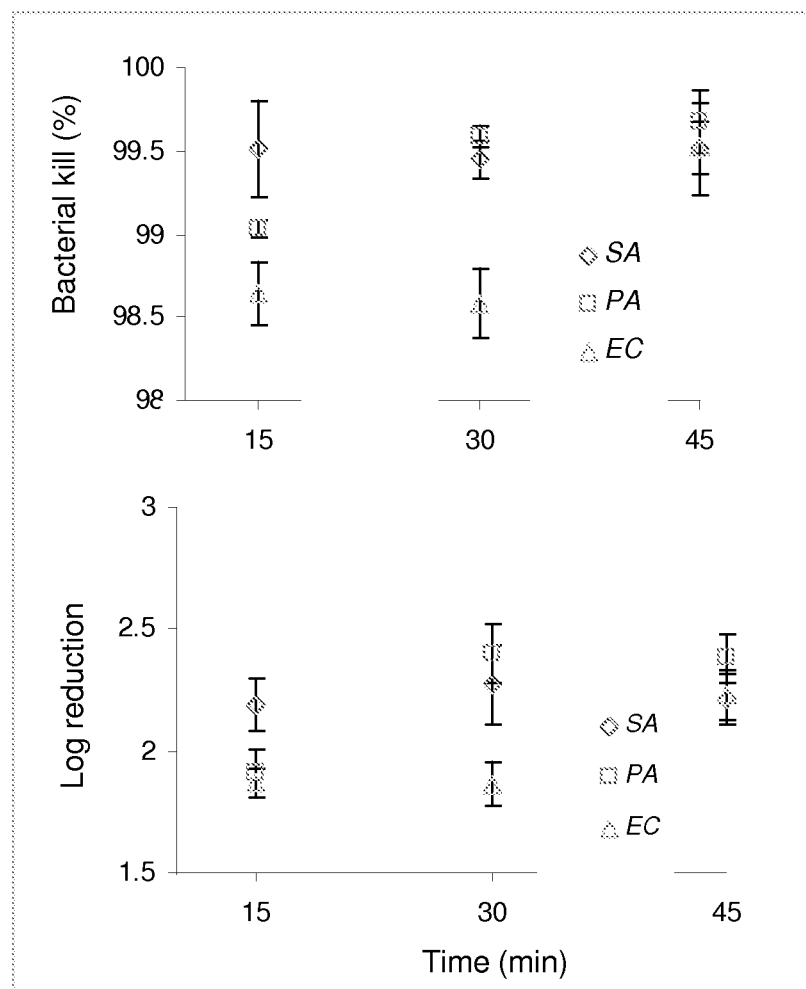
Figure 17. Percent kill and log reduction of a PDMS coating modified with 1 wt% of QAM, as a function of time.

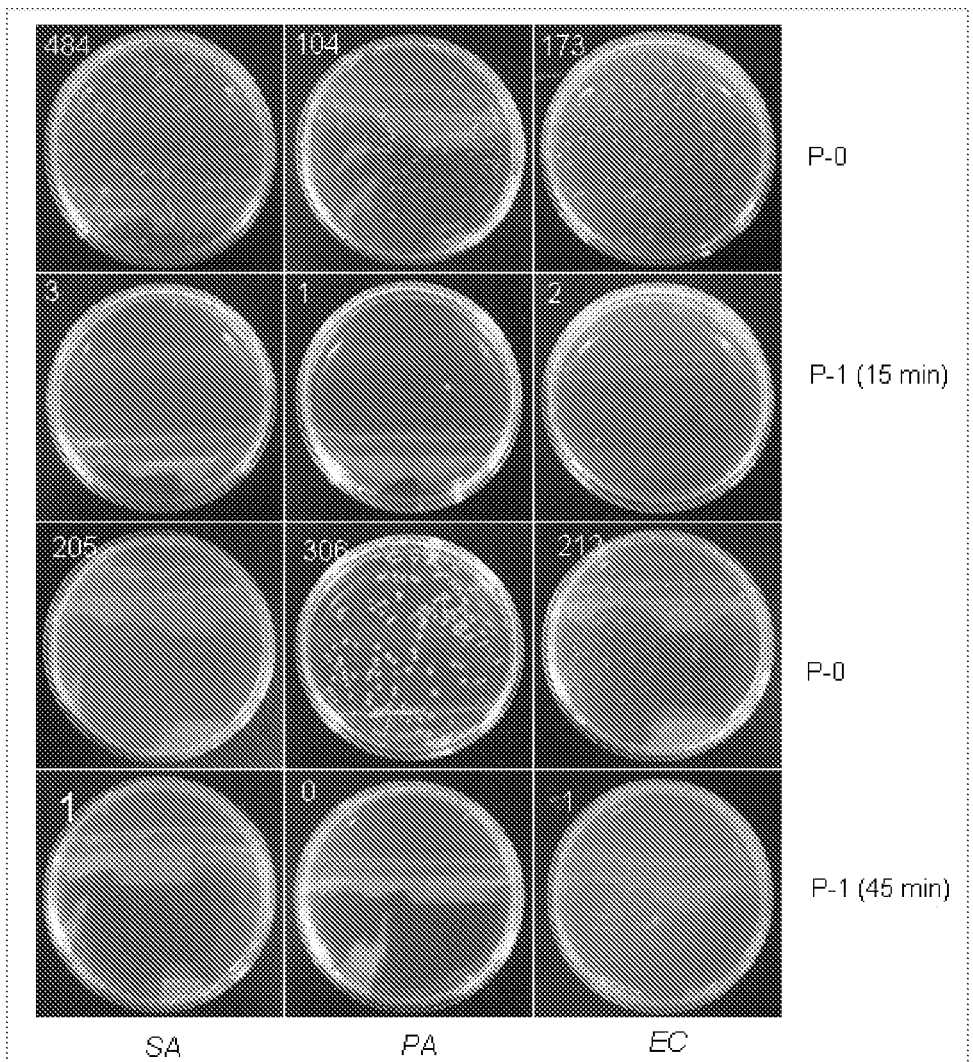
Figure 18. Results from the antimicrobial assay with residence time of 15 and 45 min, demonstrating time dependant biocidal activity.

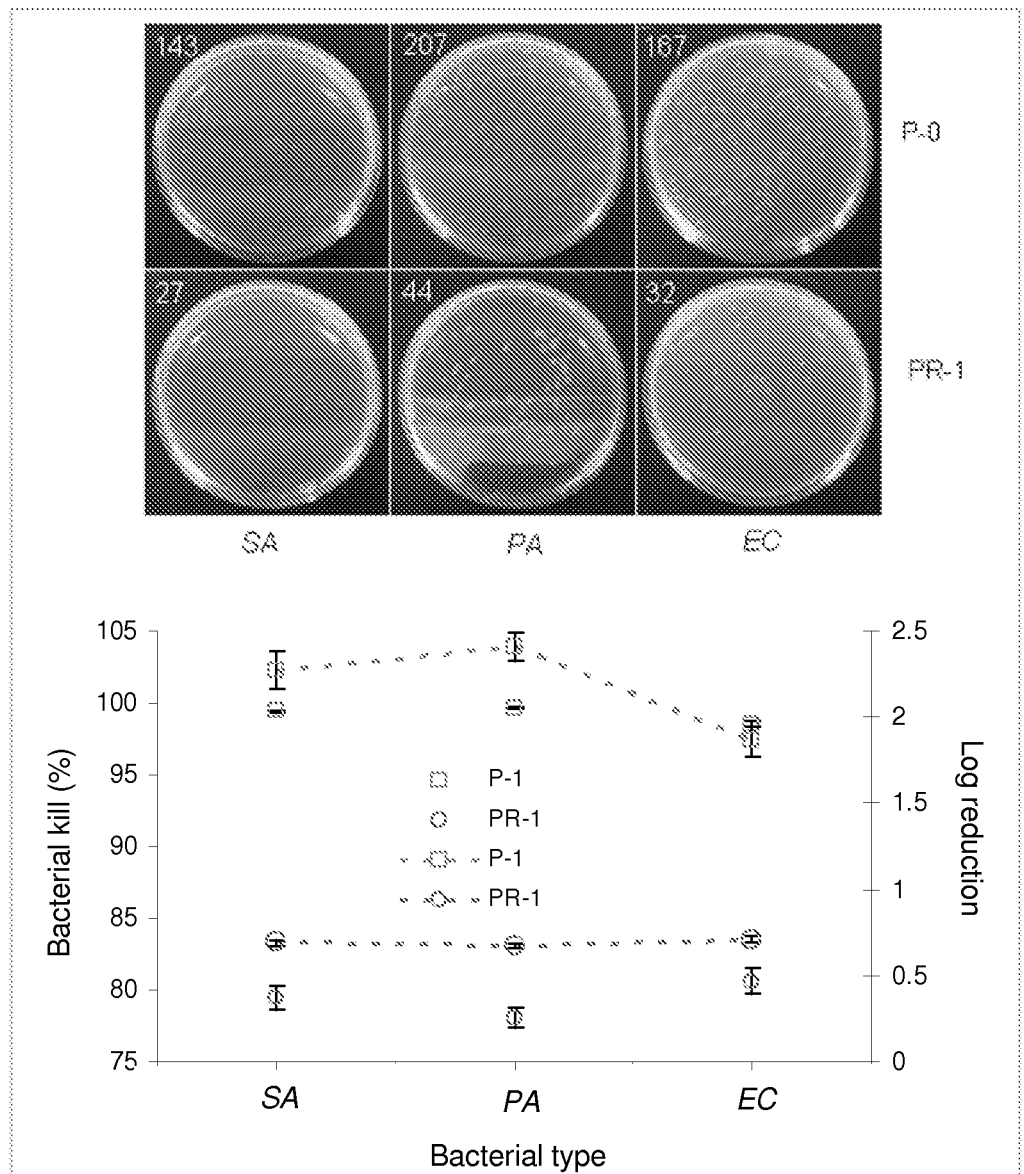
Figure 19. (Top)-Biocidal test results with a control and the filled PDMS coating (1% modified), showing the remnant number of cfu. (Bottom)-Comparison of biocidal activity (% kill and log reduction in bacterial cfu) between an unfilled and filled PDMS sample modified with 1 wt% of the QAM.

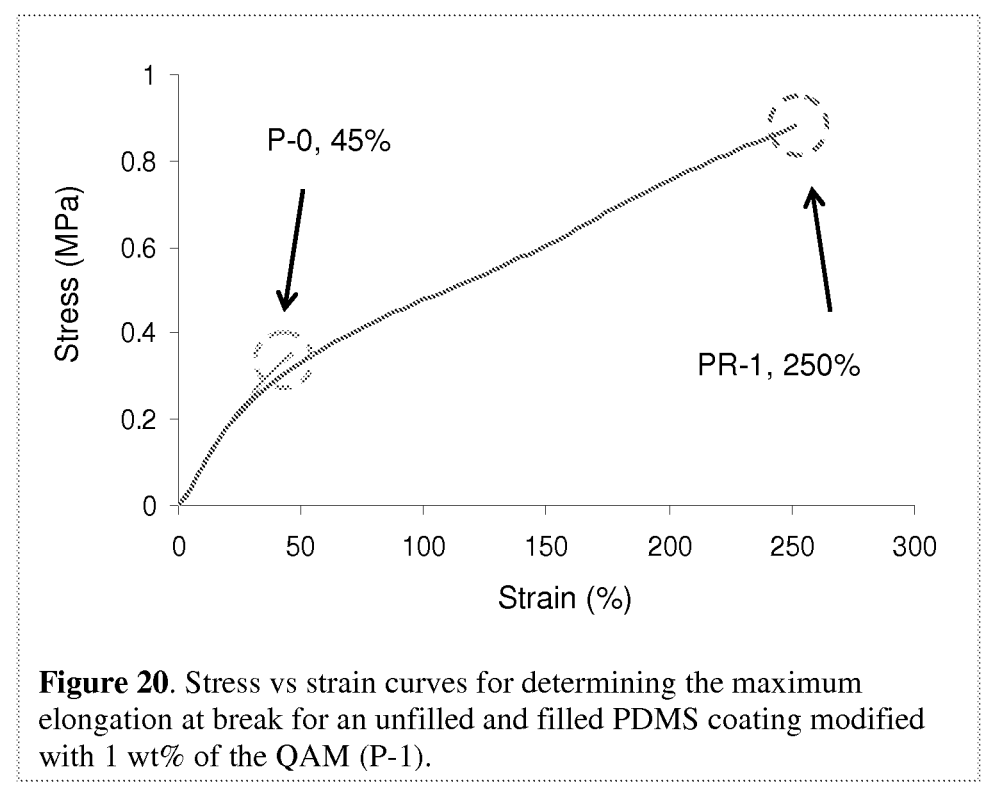
Figure 20. Stress vs strain curves for determining the maximum elongation at break for an unfilled and filled PDMS coating modified with 1 wt% of the QAM (P-1).

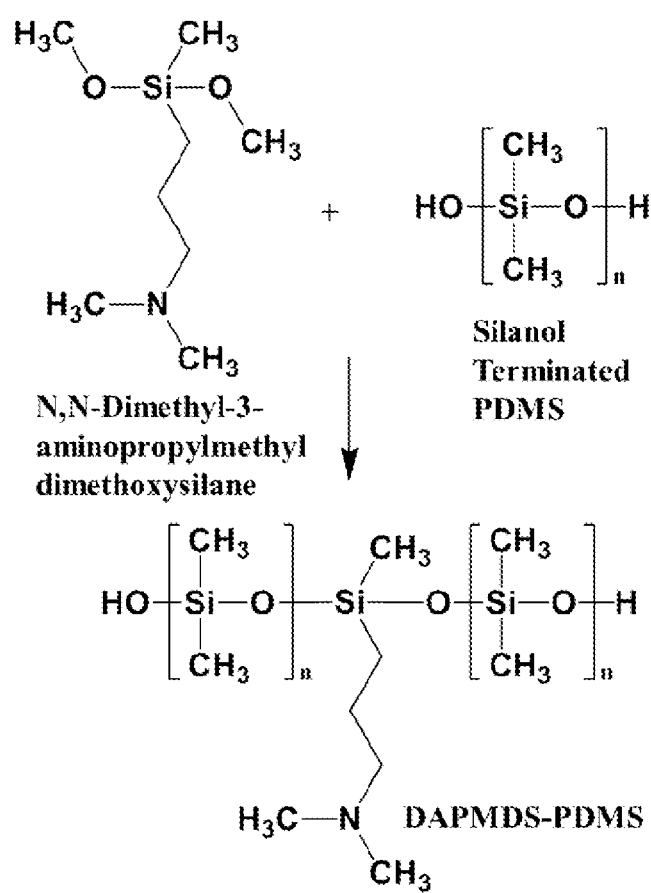
Figure 21. Synthetic route of DAPMDS-PDMS

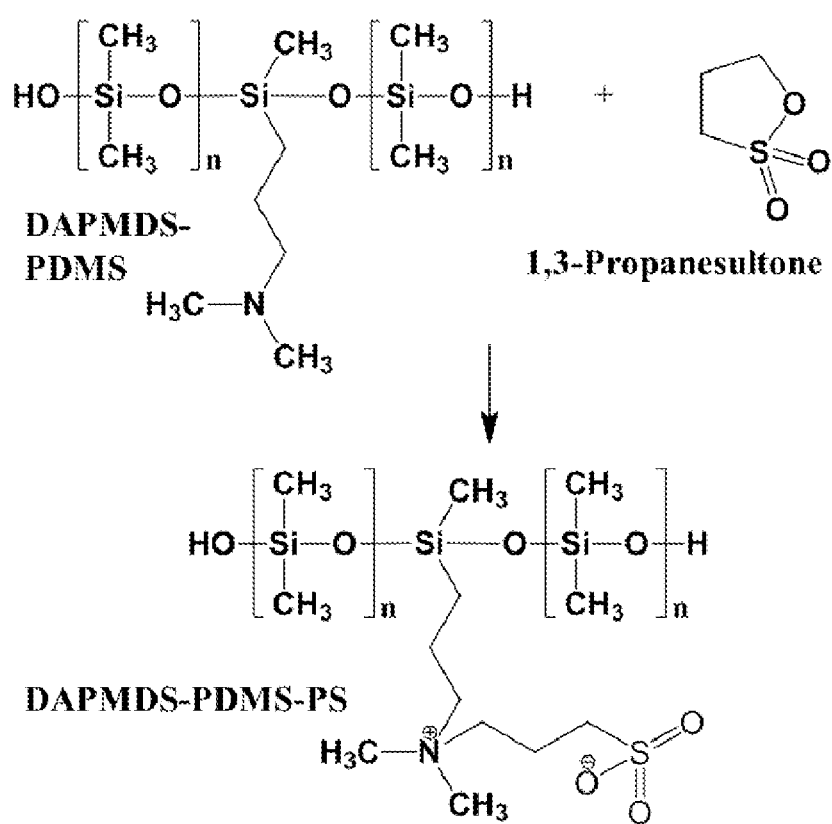
Figure 22. Synthetic route of DAPMDS-PDMS-PS

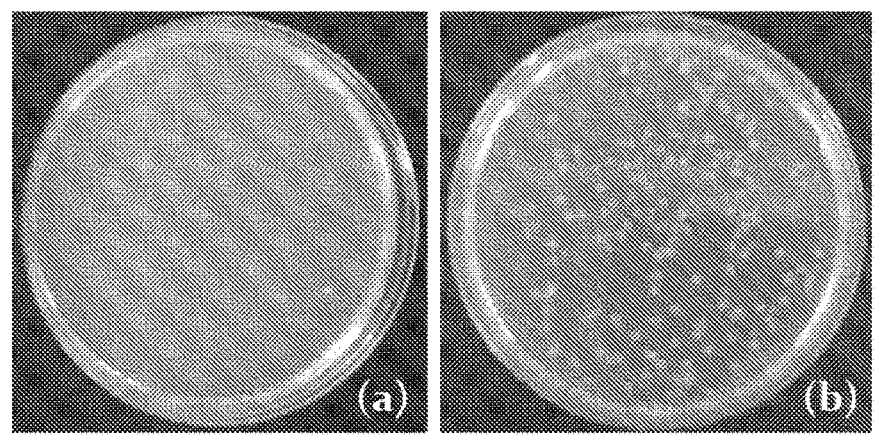
Figure 23. Antibacterial activity against *P. aureus* after 30 min contact time of (a) coating including 2 wt% DAPMDS-PDMS-PS modifier and (b) control without modifier.

ANTIMICROBIAL POLYMERIC COMPOSITIONS

REFERENCE TO EARLIER APPLICATIONS

This application claims priority to U.S. Provisional Application Ser. No. 61/552,452, filed Oct. 27, 2011, and 61/552,454, filed Oct. 27, 2011.

GOVERNMENT LICENSE RIGHTS

This invention was made with government support under DMR grants DMR-0207560 DMR-0802452, and DMR-1206259 awarded by the National Science Foundation and Office of Naval Research Grant #000140-81-09-2-2 awarded by the Office of Naval Research. The government has certain rights in the invention. National Science Foundation (DMR-grants DMR-0207560, DMR-0802452, and DMR-1206259), the Office of Naval Research (Grant #000140-81-09-2-2) and the VCU School of Engineering Foundation supported this research.

FIELD OF THE APPLICATION

The present application relates to polymer compositions which impart microbial resistance.

BACKGROUND

Infection acquired from health care environments is one of the leading major medical complications in the present world. Studies have shown that almost 6% of patients admitted to hospitals acquire infections and the number of such cases is increasing. According to reports by the US Center of Disease Control that hospital acquired infections account for more than 2 million cases leading to 99,000 deaths annually.

The most common hospital acquired infections include urinary tract infections, surgical wound infections and those associated with intravascular cannulas. The mode of transmission of these infections is mostly by physical contact with infected medical devices. *Staphylococcus aureus, Pseudomonas aeruginosa,* and *Escherichia coli* are the most common bacterial isolates that give rise to these infectious diseases. It has been observed that most of the bacterial strains develop resistance to antibiotics over a period of time. In the hospital environment, over 50% of *Staphylococcus aureus* have developed resistance to methicillin, which ultimately leads to surgical wound infection and catheter related sepsis. Some of the emerging antibiotic resistant pathogens include vancomycin resistant enterococci, vancomycin intermediate *staphylococcus*, and multiple antibiotic resistant Gram negative organisms like *acinetobacter, enterobacter* and *mycobacterium.*

Biocidal polymers offer promise in helping curb the spread of infections by providing coatings for applications such as biomedical devices or molded articles. An antimicrobial avoids adhesion and proliferation of planktonic microbes on the surface by either repelling or killing the microbes. While repelling surfaces can be achieved by creating ultrahydrophobic surfaces, the killing of microbes can be achieved by either biocide release or contact kill. In some instances release and contact kill are combined. Contact antimicrobial function is accomplished by covalently bonding the biocide; thereby, promising durability. Because contact kill precludes the biocide entering the bacterial metabolic processes, elimination of bacterial resistance buildup may result. Interest in contact kill has led to a number of studies on polymers with covalently bound alkylammonium groups.

Contact kill silicone coatings include a class of biocidal polysiloxanes with 3-(alkyldimethylammonium)propyl pendant groups. Antimicrobial activity of PDMS chains terminated with quaternary ammonium functionalities bearing oxyethylene moieties has been studied. In a humid environment, these oxyethylene chains spread out, exposing the ammonium moieties which imparts biocidal property to these compounds. Simultaneously, cationic silicones have also been used as surface modifiers, one of them being a reactive silane, $(MeO)_3Si(CH_2)_3N^+Me_2C_{18}H_{37}Cl^-$ (DC 5700). This compound, developed by Dow Corning, renders bactericidal properties to surfaces like glass, cotton, polyester fibers.

Quaternary function (sometimes referred to herein as "quat") has been introduced into PDMS coatings using $R_{quat}Si(OR)_3$ and condensation cure. With trifunctional $R_{quat}Si(OR)_3$ competition must occur between quaternary function in the bulk (crosslinker) and at the surface. Accordingly, 10-15 weight percent $R_{quat}Si(OR)_3$ was required to obtain modest antimicrobial activity, which is undesirable due to expense.

Cationic surface active polyurethane surface modifiers as antimicrobial coatings have been previously studied. Examples include HMDI-BD based polyurethanes such as shown in FIG. 1 as the polymer surface modifier containing a random P[AB] copolyoxetane soft block, where A is a fluorine based oxetane (3FOx) and B contains a quaternary ammonium side chain (C12) with a twelve membered carbon chain. HMDI is $H_{12}MDI$, (4,4'-(methylene bis-(p-cyclohexyl isocyanate)) and BD is 1,4-butane diol have been used for hard blocks in studies for antimicrobial coatings.

A small percentage of this modifier polyurethane was blended with a HMDI-BD-PTMO polyurethane (base polyurethane) which is commonly used in various industrial applications. It was observed that the resulting P[AB] polyurethane, when blended with an HMDI-BD-PTMO polyurethane, exhibited excellent antimicrobial properties. However, the surface active charge was not stable, and the antimicrobial property decreased drastically after two weeks.

Betaines are a specialized family of zwitterion that comprise both a cationic moiety and anionic functional groups. Various betaines have shown good antibacterial activity and a broad scope of inhibition. In previous studies, betaines were introduced into to the polymer backbone through ether, amide, imide, or other hydrolysable chemical bonds. However, these suffered from leaching from the substrate and decreasing antibacterial activity during use. The antibacterial agent siloxanesulfopropylbetaine (SSPB) with a reactive alkoxysilane group for the finishing of cotton textiles has been previously studied.

BRIEF DESCRIPTIONS OF THE FIGURES

FIG. 1 shows one embodiment of a conventional composition, HMDI-BD(30)-P[3FOx)(C12)-86:13-$M_n$]

FIG. 2 presents biocidal tests described in the examples.

FIG. 3 shows one embodiment of P[AB] copolyoxetane polyurethane PSM; soft block "brush" surface concentration; and base polyurethane.

FIG. 4 shows one embodiment of a conventional composition PSM MDI/BD-P[3FOx)(MEnOx)-p:(1-p)], 27-42 hard block wt %, and base MDI/BD(36)-PTMO(2200).

FIG. 5 presents biocidal test results.

FIG. 6 presents one embodiment of an exemplary composition and results observed therefor.

Figure 7:
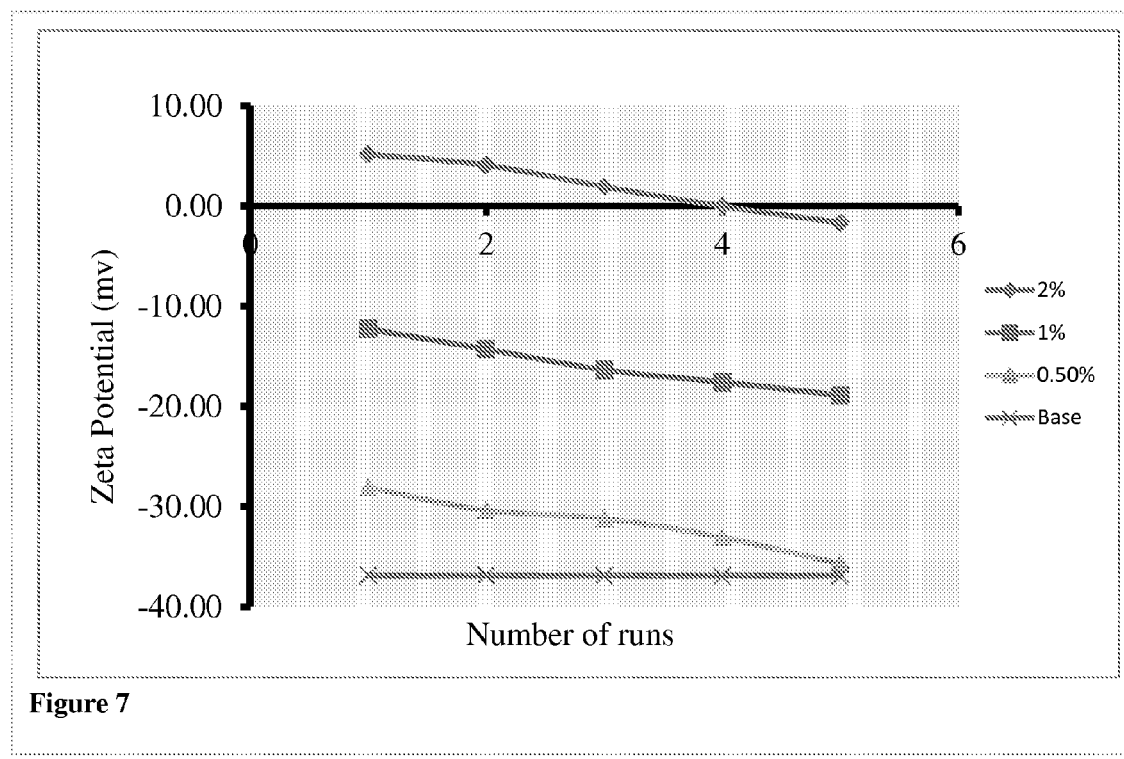

FIG. 7 presents zeta potential results described in the examples.

Figure 8:
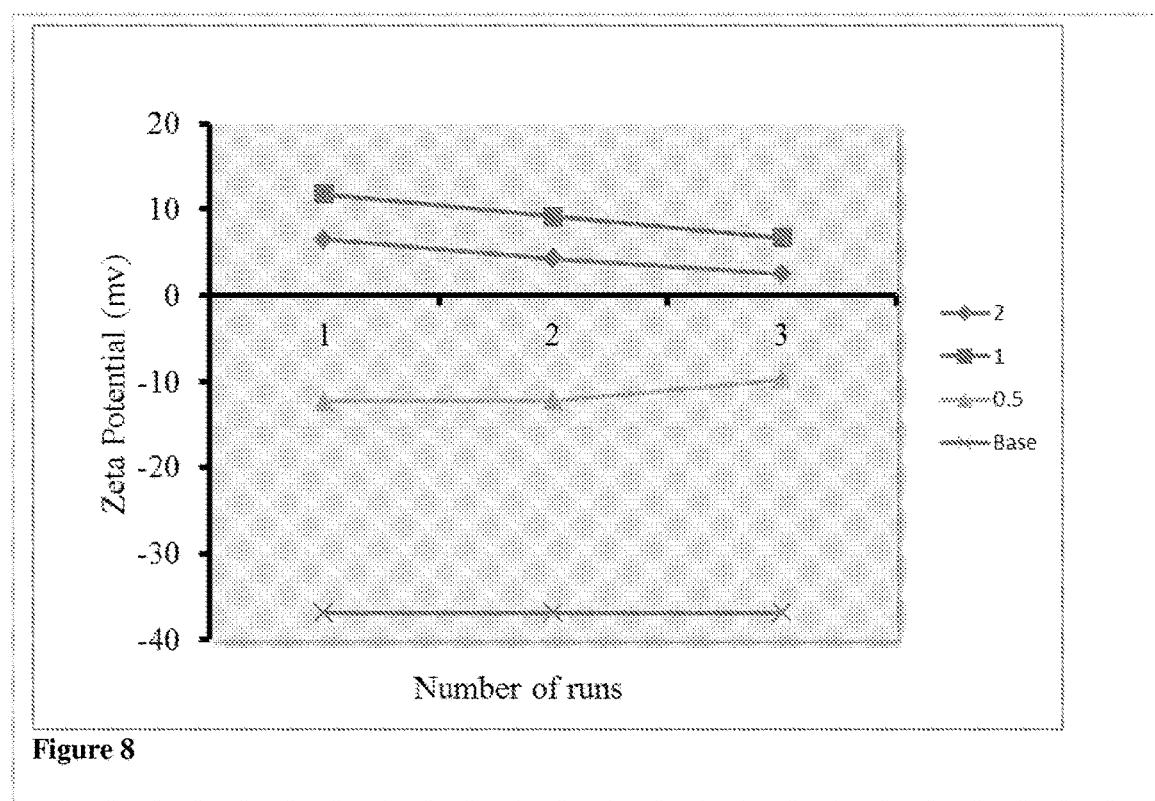

FIG. 8 presents zeta potential results described in the examples.

Figure 9:
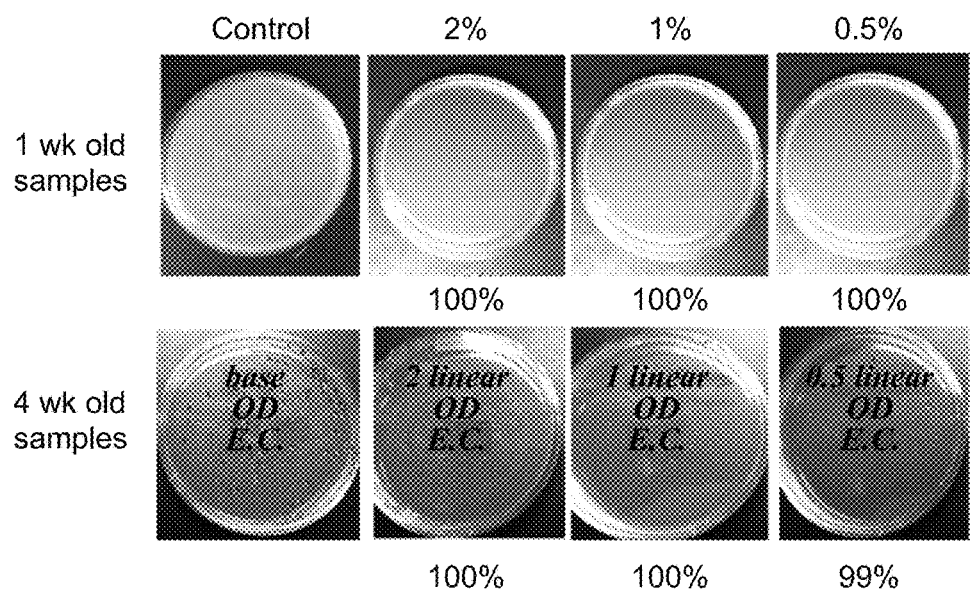

FIG. 9 presents antimicrobial results for an exemplary composition.

Figure 10:
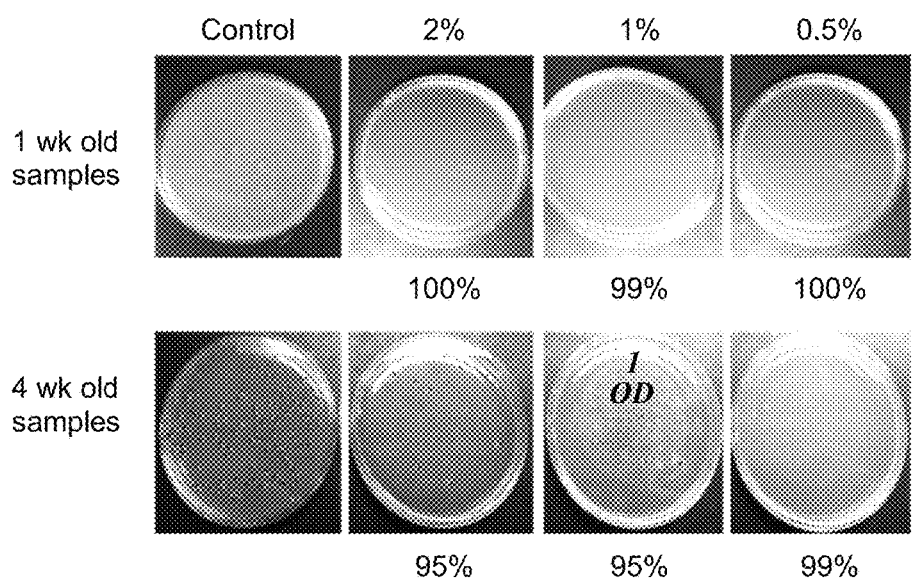

FIG. 10 presents antimicrobial results for an exemplary composition.

Figure 11:
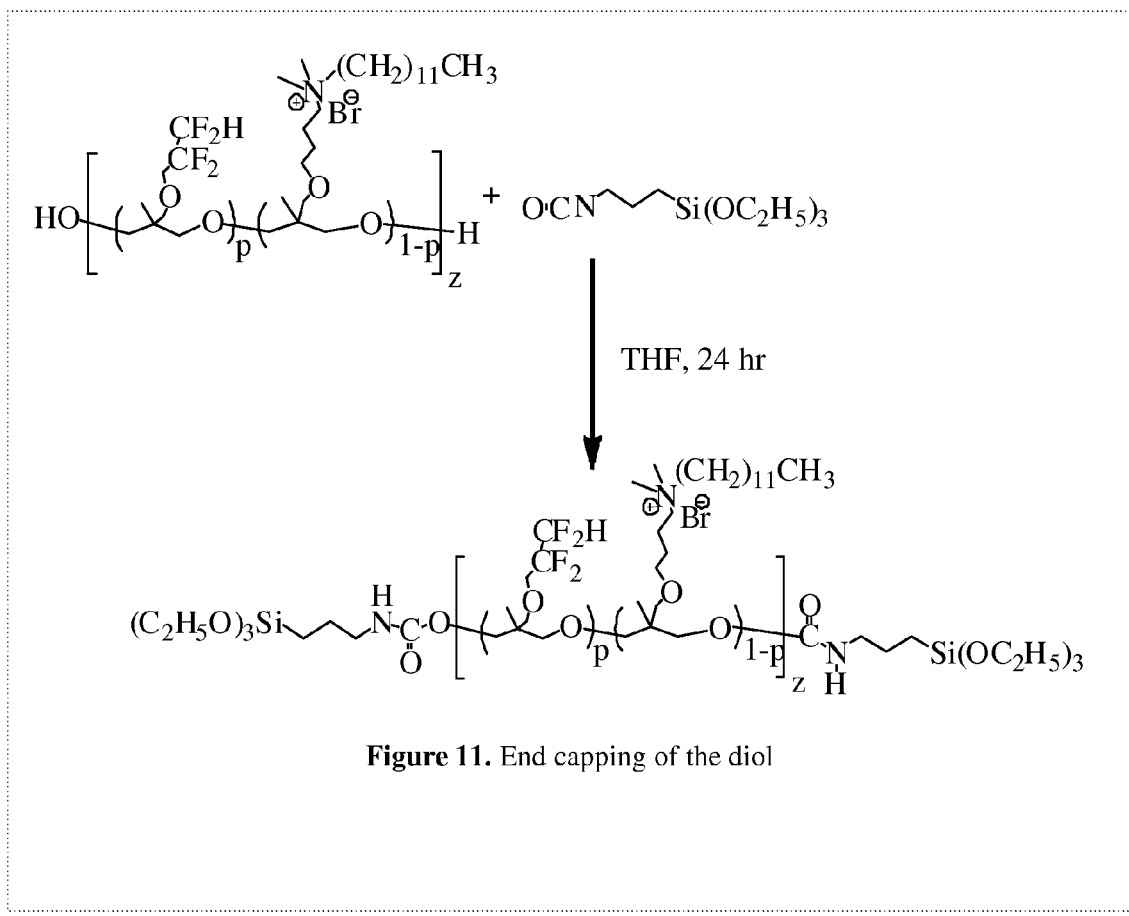

FIG. 11 presents one embodiment of end capping a diol.

Figure 12:
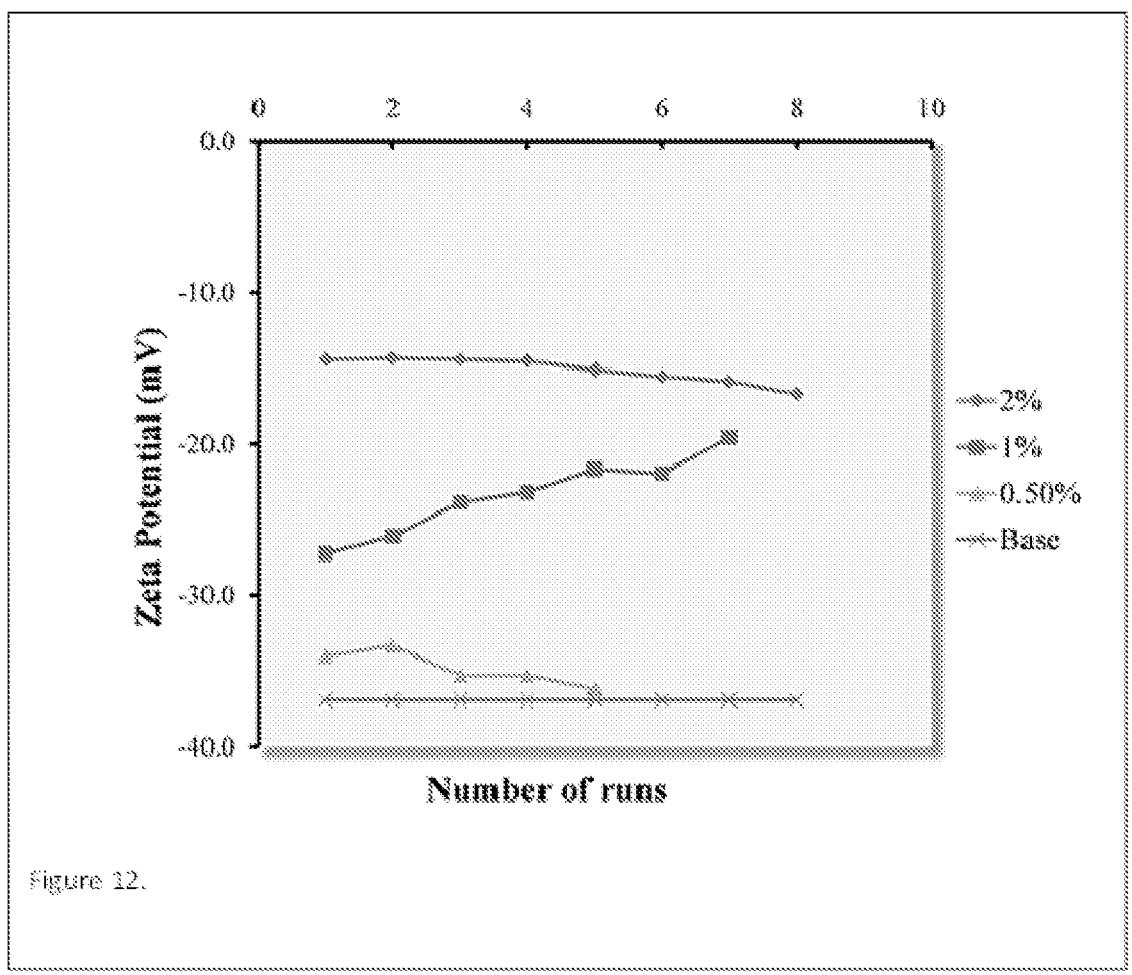

FIG. 12 presents zeta potential results described in the examples.

FIG. 13 presents one embodiment for preparation of the quaternary ammonium modifier and a representative modified PDMS coating.

FIG. 14 presents embodiments of condensation reactions.

FIG. 15 presents test results described in the examples.

FIG. 16 presents biocidal test results described in the examples.

FIG. 17 presents test results described in the examples.

FIG. 18 presents test results described in the examples.

FIG. 19 presents biocidal test results described in the examples.

FIG. 20 presents mechanical test results described in the examples.

FIG. 21 presents one embodiment of a synthetic route of DAPMDS-PDMS.

FIG. 22 presents one embodiment of a synthetic route of DAPMDS-PDMS-PS.

FIG. 23 presents biocidal test results described in the examples.

BRIEF SUMMARY OF THE SEVERAL EMBODIMENTS

One embodiment provides a polyoxetane diol having the formula:

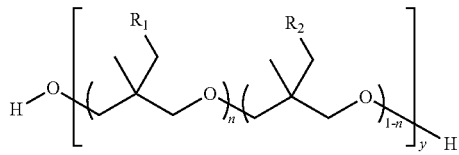

wherein n is 0 to 1;
wherein y is an integer of 1-1000; and
wherein $R_1$ and $R_2$ are not identical and are each independently —$OCH_2CF_2H$, —$OCH_2CF_2CF_2H$, —$OCH_2CF_2CF_2CF_2H$, —Br, —$(OC_2H_4)_x$(—O—$CH_3$), wherein x is 0-11, alkoxy, fluoroalkoxy, alkoxycycloalkyl, or a group having one of the following formulas:

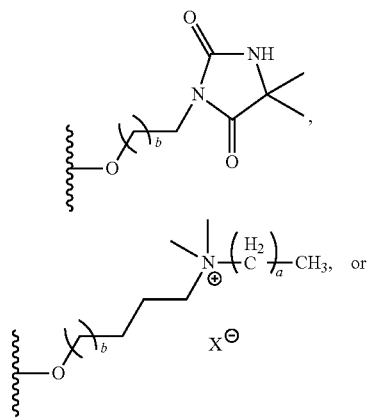

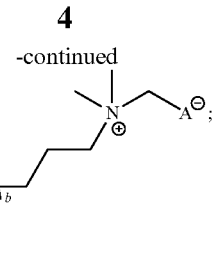

wherein a is 5-15;
wherein b is 0-5
wherein X is Cl, Br, I, OH, or $NO_3$; and
wherein A is —$CO_2$ or —$SO_3$.

In one embodiment, the polyoxetane diol may have one of the following formulas:

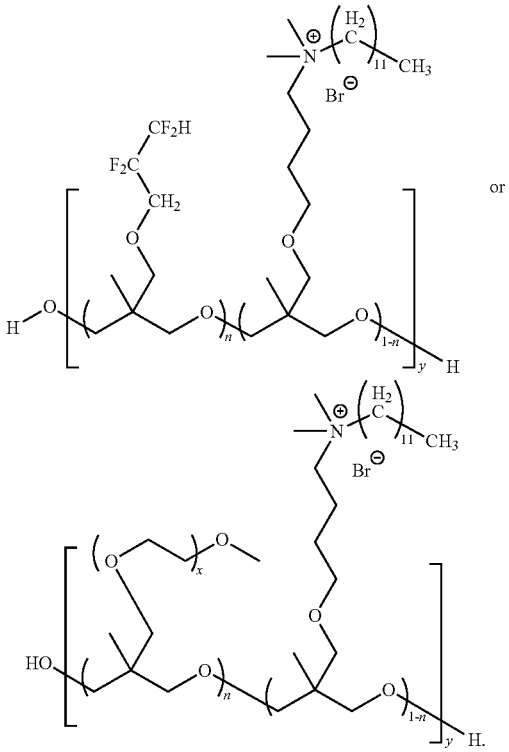

One embodiment provides a polymer, comprising a polymerization product of:
(A) the polyoxetane diol;
(B) one or more of an isocyanate, diisocyanate, or combination thereof;
(C) optionally, a diol or diamine chain extender; and
(D) optionally, a soft block diol selected from the group polydimethylsiloxane diol, polytetramethylene oxide diol, polypropylene oxide diol, polyethylene oxide diol, polybutadiene diol, polyisobutylene diol, perfluorinated diol, or a combination of two or more thereof.

In one embodiment, the isocyanate may have the formula:

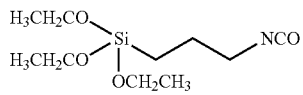

so that a compound having the following formula is produced:

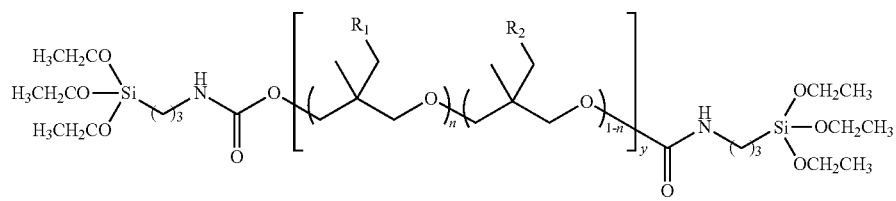

wherein n is 0 to 1;
wherein y is an integer of 1-1000; and
wherein $R_1$ and $R_2$ are not identical and are each independently —$OCH_2CF_2H$, —$OCH_2CF_2CF_2H$, —$OCH_2CF_2CF_2CF_2H$, —Br, —$(OC_2H_4)_x$(—O—$CH_3$), wherein x is 0-11, alkoxy, fluoroalkoxy, alkoxycycloalkyl, or a group having one of the following formulas:

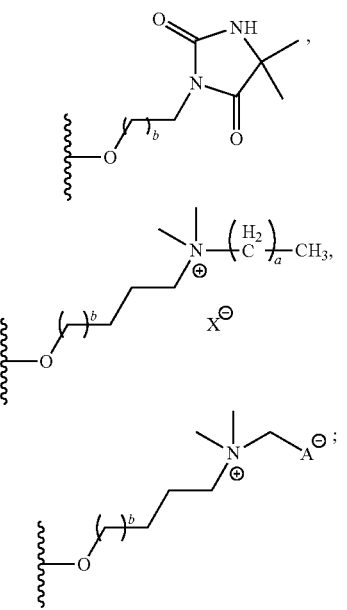

wherein a is 5-15;
wherein b is 0-5
wherein X is Cl, Br, I, OH, or $NO_3$; and
wherein A is —$CO_2$ or —$SO_3$.

One embodiment provides an end-capped compound having the formula:

wherein $R_1$ and $R_2$ are not identical and are each independently —$OCH_2CF_2H$, —$OCH_2CF_2CF_2H$, —$OCH_2CF_2CF_2CF_2H$, —Br, —$(OC_2H_4)_x$(—O—$CH_3$), wherein x is 0-11, alkoxy, fluoroalkoxy, alkoxycycloalkyl, or a group having one of the following formulas:

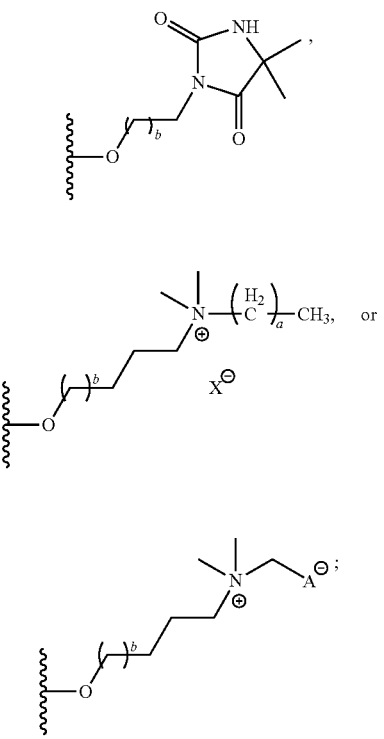

wherein a is 5-15;
wherein b is 0-5
wherein X is Cl, Br, I, OH, or $NO_3$; and
wherein A is —$CO_2$ or —$SO_3$.

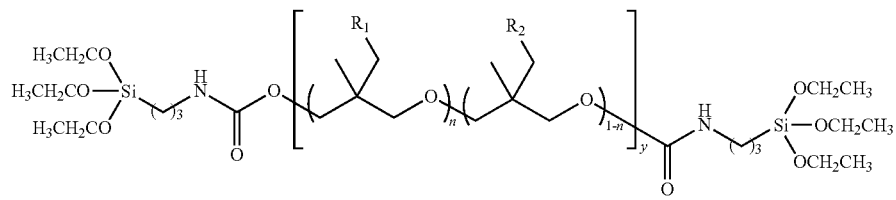

wherein n is 0 to 1;
wherein y is an integer of 1-1000; and

In one embodiment, the end-capped compound may have one of the following formulas:

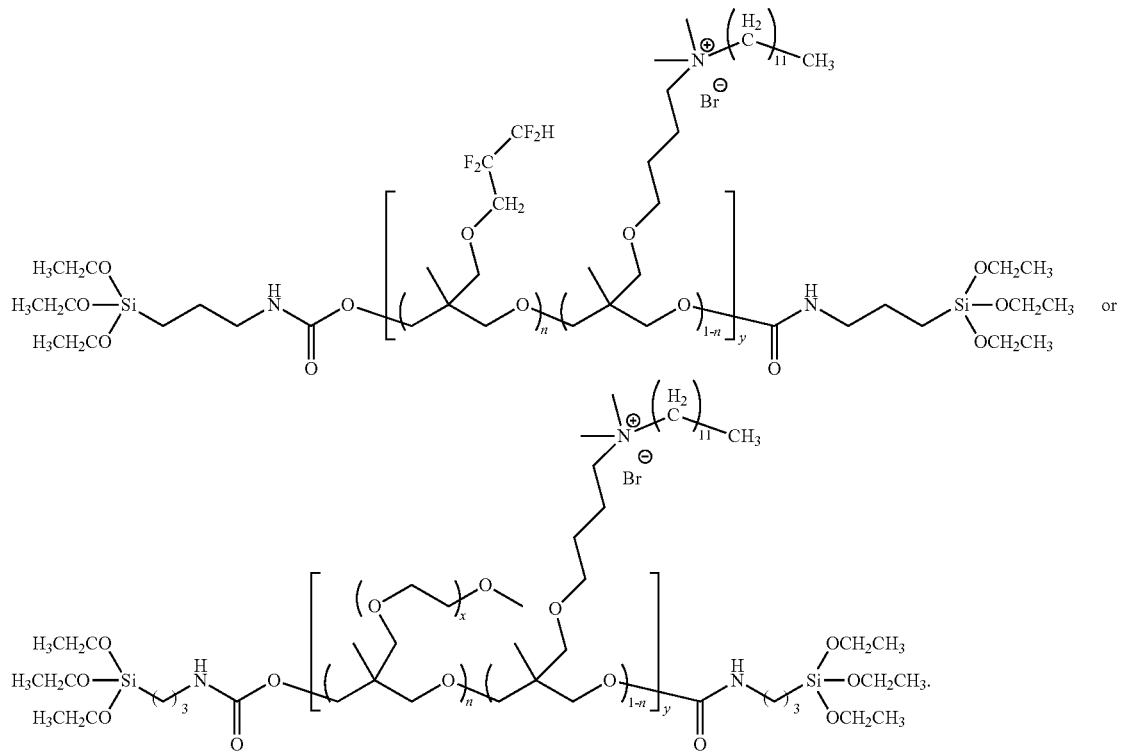

One embodiment provides a composition, comprising a polymerization product of:
(A) the end-capped compound;
(B) one or more bis(trialkoxysilyl)alkanes having the formula:

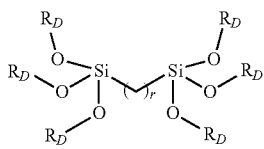

wherein $R_D$ is —CH$_3$, —CH$_2$CH$_3$, —CH$_2$CH$_2$CH$_3$, or —CH$_2$CH$_2$CH$_2$CH$_3$; and wherein r is an integer of 1-10;
or one or more polydialkoxysiloxanes having the formula:

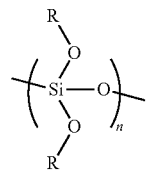

where R is —CH$_3$ or —C$_2$H$_5$;
(C) one or more of an isocyanate, diisocyanate, or combination thereof;
(D) optionally, a diol or diamine chain extender; and
(E) optionally, a soft block diol selected from the group consisting of polydimethylsiloxane diol, polytetramethylene oxide diol, polypropylene oxide diol, polyethylene oxide diol, or a combination of two or more thereof.

In one embodiment, (B) may have the formula:

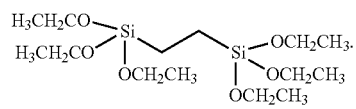

One embodiment provides a composition, comprising:
(a) a reaction product of:
(A) the end-capped compound; and
(B) one or more bis(trialkoxysilyl)alkanes having the formula:

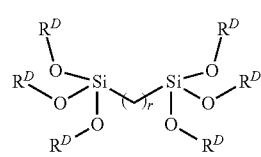

wherein $R_D$ is —CH$_3$, —CH$_2$CH$_3$, —CH$_2$CH$_2$CH$_3$, or —CH$_2$CH$_2$CH$_2$CH$_3$; and wherein r is an integer of 1-10;

or one or more polydialkoxysiloxanes having the formula:

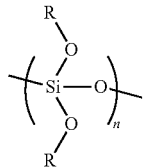

where R is —CH$_3$ or —C$_2$H$_5$;
and
(b) a polymerization product of:
  (C) one or more of an isocyanate, diisocyanate, or combination thereof;
  (D) optionally, a diol or diamine chain extender; and
  (E) optionally, a soft block diol selected from the group consisting of polydimethylsiloxane diol, polytetramethlene oxide diol, polypropylene oxide diol, polyethylene oxide diol, polydimethylsiloxane dipropylamine, or a combination of two or more thereof.

The composition may be either a blend, copolymer, or crosslinked copolymer matrix. In one embodiment, the composition is a blend of (a) and (b).

One embodiment provides a difunctional surface modifying agent, having the formula:

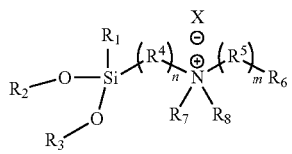

wherein R$^1$, R$^2$, R$^3$, R$^6$, R$^7$, R$^8$ are each independently hydrogen, alkyl, alkenyl, cycloalkyl, or aryl;

wherein each R$^4$ is independently a —CR$^9$R$^{10}$— group wherein R$^9$ and R$^{10}$ are each independently hydrogen or alkyl;

wherein each R$^5$ is independently a —CR$^9$R$^{10}$— group wherein R$^9$ and R$^{10}$ are each independently hydrogen or alkyl;

wherein X is anion, Cl, Br, I, OH, or NO$_3$;
wherein n is 1-20; and
wherein m is 1-20.

In one embodiment, the difunctional surface modifying agent has the formula:

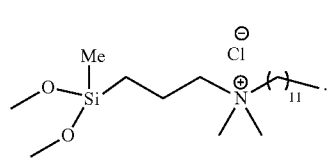

One embodiment provides a method of making the difunctional surface modifying agent, comprising reacting a compound having the formula:

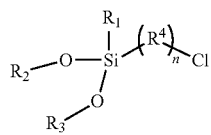

with a compound having the formula:

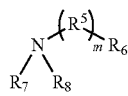

to produce the surface modifying agent.

In one embodiment, the reactants for the surface modifying agent have the respective following formulas:

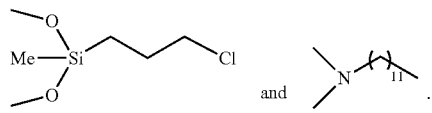

One embodiment provides a polymer, comprising a polymerization product of:
  (A) the difunctional surface modifying agent;
  (B) a soft block diol selected from the group polydimethylsiloxane diol, polytetramethylene oxide diol, polypropylene oxide diol, polyethylene oxide diol, polybutadiene diol, polyisobutylene diol, perfluorinated diol, or a combination of two or more thereof; and
  (C) optionally, one or more bis(trialkoxysilyl)alkanes having the formula:

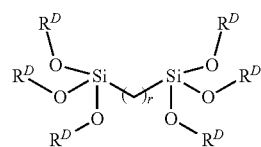

wherein R$_D$ is —CH$_3$, —CH$_2$CH$_3$, —CH$_2$CH$_2$CH$_3$, or —CH$_2$CH$_2$CH$_2$CH$_3$; and wherein r is an integer of 1-10;

or one or more polydialkoxysiloxanes having the formula:

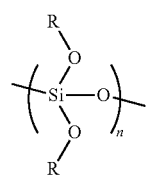

where R is —CH$_3$ or —C$_2$H$_5$.

In one embodiment, (A) is a compound having the formula:

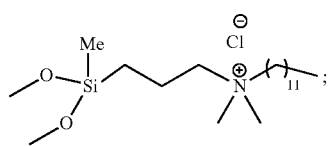

(B) is a polydimethylsiloxane diol; and
(C) is a compound having the formula:

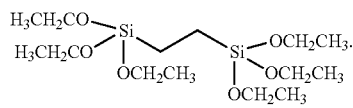

One embodiment provides a polymer, comprising a polymerization product of:
(A) a compound having one of the following formulas:

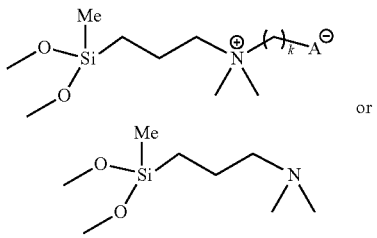

wherein k is 1-4;
and wherein A is —CO$_2$ or —SO$_3$;
(B) a soft block diol selected from the group polydimethylsiloxane diol, polytetramethylene oxide diol, polypropylene oxide diol, polyethylene oxide diol, polybutadiene diol, polyisobutylene diol, perfluorinated diol, or a combination of two or more thereof; and
(C) optionally, one or more bis(trialkoxysilyl)alkanes having the formula:

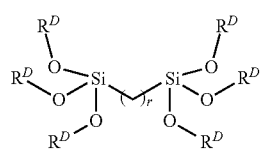

wherein $R_D$ is —CH$_3$, —CH$_2$CH$_3$, —CH$_2$CH$_2$CH$_3$, or —CH$_2$CH$_2$CH$_2$CH$_3$; and
wherein r is an integer of 1-10;
or one or more polydialkoxysiloxanes having the formula:

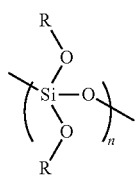

where R is —CH$_3$ or —C$_2$H$_5$.
In one embodiment in the polymer above, (B) is a polydimethylsiloxane diol; and (C) is a compound having the formula:

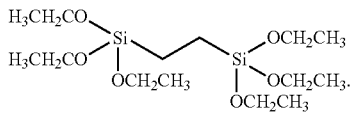

The ranges described in the embodiments above can have any values or subranges therebetween. For example, wherein n is 0 to 1, referring to a mixture, n can have any value therebetween, including 0, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, any combination thereof, or any subrange therein. This nomenclature and equivalent versions of it are well-known in the polymer arts.

For example, wherein y is an integer of 1-1000, y may adopt any value including for example, 1, 2, 3, 4, 5, 6, 7, 8, 9, 10, 20, 30, 40, 50, 60, 70, 80, 90, 100, 200, 250, 500, 750, 900, 1000, any combination thereof, or any subrange therein. This nomenclature and equivalent versions of it are well-known in the polymer arts.

So long as $R_1$ and $R_2$ are not identical, each may be independently —OCH$_2$CF$_2$H, —OCH$_2$CF$_2$CF$_2$H, —OCH$_2$CF$_2$CF$_2$CF$_2$H, —Br, —(OC$_2$H$_4$)$_x$(—O—CH$_3$ (wherein x is 0-11, including 0, 1, 2, 3, 4, 5, 6, 7, 8, 9, 10, and 11 or any subrange therein), alkoxy, fluoroalkoxy, alkoxycycloalkyl, or a group having one of the following formulas:

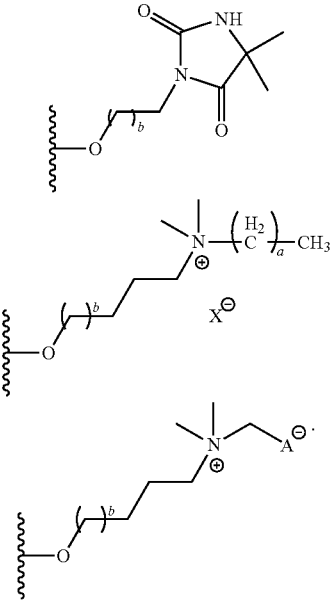

In the formulas described, a is 5-15 or any subrange therebetween, including 5, 6, 7, 8, 9, 10, 11, 12, 13, 14, 15, or any subrange therein.

In the formulas described, b is 0-5 or any subrange therebetween, including 0, 1, 2, 3, 4, 5, or any subrange therein.

In the formulas described, r is an integer of 1-10 or any subrange therebetween, including 1, 2, 3, 4, 5, 6, 7, 8, 9, 10, or any subrange therein.

In the formulas described, X may be any one of Cl, Br, I, OH, or NO$_3$ or, if more than one compound is present, each compound may have a different X, or every compound may have the same X.

In the formulas described, A is —CO₂ or —SO₃ or, if more than one compound is present, each compound may have a different A or every compound may have the same A.

In the formulas described, the isocyanates and diisocyanates are not particularly limited and, given the teachings herein combined with the knowledge of one of ordinary skill, they can be selected as appropriate. For example, methylene dicyclohexyl diisocyanate, diphenylmethane diisocyanate, hexamethylene diisocyanate, isophorone diisocyanate, toluene diisocyanate, xylylene diisocyanate, cyclohexane diisocyanate, tetramethyl xylylene diisocyanate, trimethylhexamethylene diisocyanate, norbornane diisocyanate, phenylene diisocyanate, or a combination of two or more thereof.

Similarly, the isocyanate is not particularly limiting. Non-limiting examples of the isocyanate include compounds having the formula:

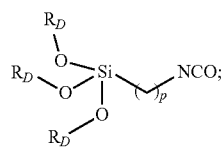

wherein $R_D$ is —CH₃, —CH₂CH₃, —CH₂CH₂CH₃, —CH₂CH₂CH₂CH₃, and p is an integer of 1-10. The p range includes all values and subranges therebetween, including 1, 2, 3, 4, 5, 6, 7, 8, 9, 10, and 11, or any subrange therein. In one embodiment, p is 1, 2, 3, or 4.

If desired, one or more chain extenders may be used, which are not particularly limiting. Any suitable diol or diamine chain extender may be used. Non-limiting examples of the diol include a $C_{1-10}$ alkylene diol, $C_{1-10}$ alkenylene diol, $C_{1-20}$ aralkylene diol, 1,4-butanediol, or the like, or combinations of two or more thereof, though others are possible. Similarly, non-limiting examples of diamine chain extenders include $C_{1-10}$ alkylene diamine, $C_{1-10}$ alkenylene diamine, $C_{1-20}$ aralkylene diamine, or the like or combinations of two or more thereof, though others are possible.

Similarly, in the formulas described, the diol or diamine chain extender are not particularly limited and, given the teachings herein combined with the knowledge of one of ordinary skill, they can be selected as appropriate. For example, chain extending diols may include a $C_{1-10}$ alkylene diol, $C_{1-10}$ alkenylene diol, $C_{1-20}$ aralkylene diol, 1,4-butanediol, or the like, or combinations of two or more thereof, although others are possible. Similarly, non-limiting examples of diamine chain extenders include $C_{1-10}$ alkylene diamine, $C_{1-10}$ alkenylene diamine, $C_{1-20}$ aralkylene diamine, or the like, or combinations of two or more thereof, although others are possible.

Similarly, in the formulas described, the soft block diol may be suitably chosen from known polydimethylsiloxane diols, polytetramethylene oxide diols, polypropylene oxide diols, polyethylene oxide diols, polybutadiene diols, polyisobutylene diols, perfluorinated diols, or a combination of two or more thereof.

HMDI/BD(30)-[(4FOx)(C12)] has the following structure:

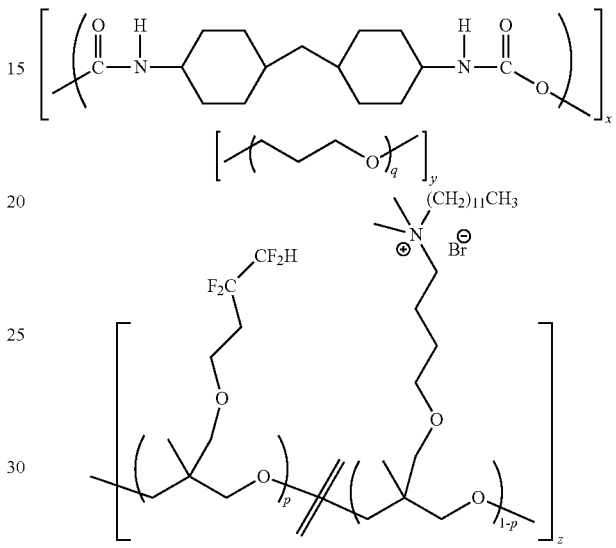

In one embodiment, a hybrid modifier may be desirable in view of stability. In another embodiment, the HMDI/BD (30)-[(4FOx)(C12)] polyurethane modifier exhibits a remarkable improvement over the conventional "—CF₃" copolyoxetane in view of the higher C12 (34 mole percent, p=66).

In one embodiment, the molecular weight for the P[4FOx) (C12)] is 5.7 kDa, which may suitably be determined by end group MW (¹H-NMR).

In one embodiment, the polyurethane modifier is HMDI/ BD(30)-[(ME2Ox)(C12)], which may be desirable in view of biocompatibility and/or cytocompatibility.

In one embodiment, the polyurethane modifier is HMDI/ BD(30)-[ME2Ox)(C12)] (with 14 mol % C12).

In one embodiment, a hybrid modifier has the following formula:

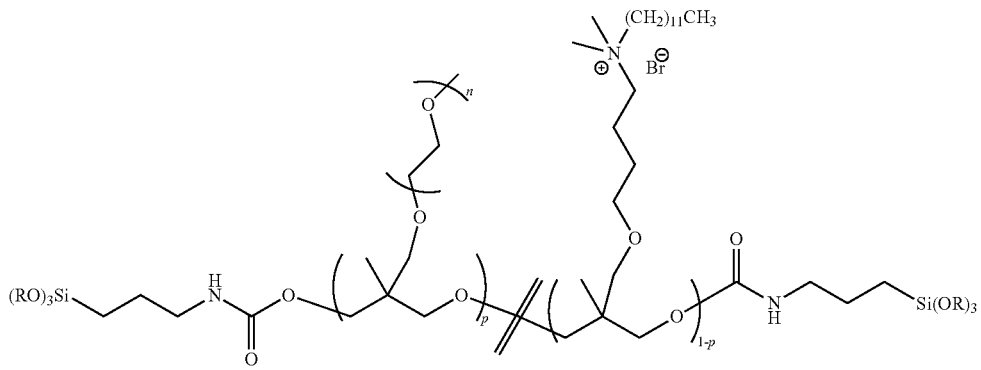

In one embodiment, for above hybrid modifier, p can range from 20-80 mol % or any subrange therein. In one embodiment, p is 50 mol % but the range.

In the compounds and compositions described, using HMDI/BD(XX)-P[(4FOx)(C12)-YY:ZZ-molecular weight] as a generic example, the "XX", "YY", and "ZZ" have the following meanings. XX is the weight percent of the "hard block" component (in this example, an HMDI/BD polyurethane, and YY is the weight percent soft block (which, in this example, is P(4FOx)(C12) copolyoxetane). The corresponding weight percent of the soft block copolyoxetane is understood, wherein the weight percents of the hard block and soft block total to 100%. The weight percents are based on those of the starting materials.

For convenience, one embodiment of a representative P[AB] diol is shown below:

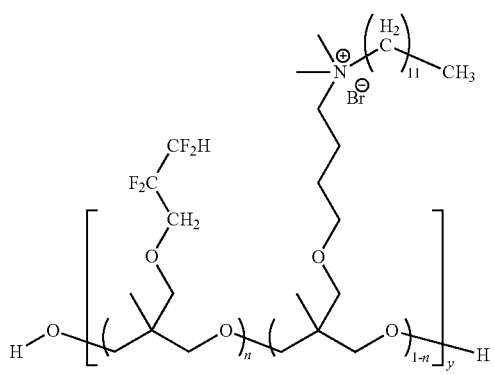

In the soft block described above (in this example, the P(4FOx)(C12) copolyoxetane) but more generically, "P[AB], the YY:ZZ refer to the mole percents of the respective A and B components (in this example, A is 4FOx oxetane co-monomer (YY), and B is the quaternised surface active oxetane co-monomer "C12".

The "-molecular weight" notation is that of the starting P[AB] diol.

In the polymer modifiers compounds and compositions described herein, XX may is not particularly limited and may suitably range from 20-40, which includes all values and subranges therebetween, including 20, 21, 22, 23, 24, 25, 26, 27, 28, 29, 30, 31, 32, 33, 34, 35, 376, 37, 38, 39, 40 wt. %, or any subrange therein. From this, the corresponding weight percent of soft block (which is not particularly limited and may range from 60-80) may be easily calculated.

The YY mole percent is not particularly limited and may suitably range from 20-80, which range includes all values and subranges therebetween, including 20, 21, 22, 23, 24, 25, 26, 27, 28, 29, 30, 31, 32, 33, 34, 35, 36, 37, 38, 39, 40, 50, 60, 70, 80 mol %, or any subrange therein. Similarly, the ZZ mole percent may range from 80-20 mol % and may be easily calculated.

The molecular weight of the starting P[AB] diol is not particularly limited and may suitably range from 200-10,000 Da, which range includes all values and subranges therebetween, including 200, 205, 225, 250, 275, 500, 505, 510, 515, 525, 550, 575, 600, 650, 700, 750, 800, 850, 900, 950, 1000, 1100, 1150, 1250, 1500, 2000, 2500, 5000, 7500, and 10,000 Da, or any subrange therein.

In one embodiment, wherein P[4FOx)(C12)] is used as the diol, YY:ZZ is 66:34.

In one embodiment, wherein P[(ME2Ox)(C12)] is used as the diol, YY:ZZ is 50:50.

In one embodiment, wherein P[(ME2Ox)(C12)] is used as the diol, the molecular weight may be 2500 Da.

In one embodiment, a hybrid modification may be used, in which a triethoxysilyl isocyanate is used to end-cap the diol, which is then combined with an alkoxysilane "booster" for the siliceous domain, added to base polyurethane solution, and drip coated or cast.

In one embodiment, amount of difunctional quaternized or zwitterionic surface modifying agent present in the modified PDMS is not particularly limited, and may be suitably range from 0.01 to 25 wt. %. This range includes all values and subranges therebetween, including 0.01, 0.02, 0.03, 0.04, 0.05, 0.06, 0.07, 0.08, 0.09, 0.1, 0.2, 0.3, 0.4, 0.5, 0.5, 0.6, 0.7, 0.8, 0.9, 1, 2, 3, 4, 5, 6, 7, 8, 9, 10, 15, 20, 25 wt. %, or any subrange therein.

In one embodiment, the amount of bis(trialkoxysilyl) alkane or poly(dialkoxysiloxane) added to the compositions is not particularly limited, and may suitably range from 0 to 35 wt. %. This range includes all values and subranges therebetween, including 0.01, 0.02, 0.03, 0.04, 0.05, 0.06, 0.07, 0.08, 0.09, 0.1, 0.2, 0.3, 0.4, 0.5, 0.5, 0.6, 0.7, 0.8, 0.9, 1, 2, 3, 4, 5, 6, 7, 8, 9, 10, 15, 20, 25, 30, 35 wt. %, or any subrange therein. One or more than one bis(trialkoxysilyl) alkane or poly(dialkoxysiloxane) may be used. Combinations of bis(trialkoxysilyl)alkane and poly(dialkoxysiloxane) may also be used. Typically, these can be used to "boost" the weight fraction of the siliceous component in the surface modifier. Such poly(dialkoxysiloxanes) are well known and may be obtained from Gelest PSI-021, Gelest PSI-023, or PSI-026. The 'n' subscript in the poly(dialkoxysiloxane) can range from 1-1000, or any integer therebetween, including 1, 2, 3, 4, 5, 6, 7, 8, 9, 10, 15, 20, 25, 30, 50, 75, 100, 200, 250, 500, 750, or any subrange therein.

The compositions may be prepared and applied to a surface or made into a device or article to impart antimicrobial resistance. As such, one embodiment relates to a device or an article having an antimicrobial surface. In one embodiment, the action is of the contact kill type, wherein the antimicrobial component does not leach out of the surface, device, or article. Non-limiting examples of such articles or devices include surface coating or composition suitable for painting, e.g., a paint, an adhesive, sealant, caulk, tubing, catheter, urinary catheter, intubation tube, shunt, cerebral shunt, transdermal device, surgical implant, artificial joint implant, medical device, bandage, dressing, fabric, clothing, utensil, food contacting surface, dental device, dental implant, breathing device, mask, tracheal implant, cannula, intravascular cannula, glove, suture material, thread, as sizing for textile materials, and the like. The compounds and compositions described herein may be used in combination as an additive, blend, copolymer, or coating with any bulk polymer such as polyesters, polyacrylates, polyurethenes, styrene butadiene rubbers, cellulosic, cotton, and the like, or other surface such as glass.

In one embodiment, the antimicrobial resistance may be effective against one or more of *Staphylococcus aureus, Pseudomonas aeruginosa, Escherichia coli*, methicillin-resistant *Staphylococcus aureus*, vancomycin resistant enterococci, vancomycin intermediate *staphylococcus*, multiple antibiotic resistant Gram negative organisms, *acinetobacter, enterobacter, mycobacterium*.

One embodiment provides a method, comprising contacting (a) at least one selected from the group consisting of polyurethane polymer, polyurethane copolymer, or a combination thereof; and (b) a composition comprising tetrahydrofuran and at least one alcohol selected from the group consisting of methanol, ethanol, propanol, isopropanol, or a combination thereof; and thereafter separating, to produce a purified polyurethane polymer, polyurethane copolymer, or a combination thereof.

Any of the polymers, blends, hybrid compositions, base polymers, coatings, and articles described herein can benefit from the application of this method.

In one embodiment, the method for purifying is carried out at a temperature of 25 to 100° C. This range includes all values and subranges therebetween, including 25, 30, 35, 40, 45, 50, 55, 60, 65, 70, 75, 80, 85, 90, 95, and 100° C.

If desired, the method for purifying additionally and optionally includes drying the purified polyurethane polymer, polyurethane copolymer, or combination thereof.

The polyurethane polymer or copolymer is not particularly limited, and the method for purifying may be suitably used on any polyurethane moiety. For example, the polyurethane can be any of an alternating copolymer, periodic copolymer, statistical copolymer, random copolymer, block copolymer, diblock copolymer, triblock copolymer, branched copolymer, linear copolymer, star copolymer, brush copolymer, comb copolymer, crosslinked copolymer, thermoplastic elastomeric copolymer, HMDI/BD-30-(PTMO), copolymer of polyurethane and 4FOx-C12, copolymer of polyurethane and 3FOx, copolymer of polyurethane and 3FOx-C12, Lubrizol ESTANE ALR-E72A™ or a combination thereof.

The relative amounts of tetrahydrofuran and alcohol used in the purification method are not particularly limiting. In one embodiment, the THF and alcohol may have a weight:weight ratio ranging from 90:10 to 10:90. This range includes all values and subranges therebetween, including any of 90, 85, 80, 75, 70, 65, 60, 55, 50, 45, 40, 35, 30, 25, 20, 15, and 10 to any of 10, 15, 20, 25, 30, 35, 40, 45, 50, 55, 60, 65, 70, 75, 80, 85, and 90 (weight:weight).

The contacting time in the purification method is not particularly limiting. In one embodiment, it may suitably range from 0.1 hr to 400 hrs. This range includes all values and subranges therebetween, including 0.1, 0.5, 1, 2, 3, 4, 5, 6, 7, 8, 9, 10, 12, 24, 36, 48, 60, 72, 96, 100, 120, 150, 180, 200, 300, and 400 hrs or any combination thereof.

In one embodiment of the purification method, the alcohol is aqueous.

So long as it is applied to a polyurethane moiety, the purification method may be used as part of a polymerization method. In one embodiment, the polymerization method comprises purifying one or more of a reactant oligomer, prepolymer, combination thereof, or the like as appropriate before further polymerizing. In another embodiment, the purification method comprises purifying a resultant polymer, copolymer, combination thereof, or the like as appropriate. Combinations are possible.

One embodiment provides a purified polyurethane polymer, copolymer, or combination thereof produced by the purification method.

In the context of the method or products prepared thereby, for a polymer to be 'purified' it need not be completely or even substantially purified after undergoing the method. That is, it may still contain a measurable or even substantial portion of impurities or contamination, e.g., unreacted monomers or reactants, surface active molecules, small molecules, water-soluble components, and the like. One way to determine whether contaminants remain is so place the purified polymer into clean water for a few minutes, then interrogate that water using a dynamic contact angle (DCA) apparatus and a clean flamed glass slide. Such methods are well-known in the art.

Conventional condensation cure is used to make coatings and elastomers. An additive that copolymerizes with standard polydimethylsiloxane diols and alkoxysilane crosslinking agents concentrates at the surface of the coating or article and generates contact antimicrobial function (no release of biocide). The additive is selectively concentrated at the surface of the coating or elastomeric object and is effective at a level of 1 wt %. The additive confers highly effective contact kill of bacteria in tests that mimic a cough, sneeze, or touch.

A recent study was done on poly(dimethylsiloxane) based coatings containing quaternary ammonium salt (QAS 1) moieties, exerting biocidal activity through contact kill. A major point of concern about this study was the use of a high weight percent (10-15%) of the trimethoxy functionalized alkylammonium salt (QAS 1).

The moderate biocidal activity observed for these coatings suggest the presence of a substantial amount of the alkylammonium modifier QAS 1, in the bulk.

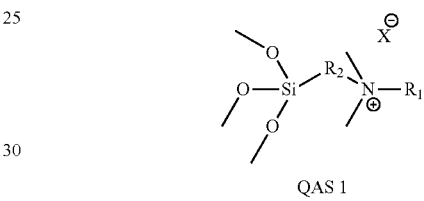

QAS 1

We have developed a new strategy for surface modification of PDMS with cationic moieties. We have found that the presence of a dimethoxy functional group provides an unexpected improvement compared to QAS 1. A difunctional alkoxy group allows incorporation of the modifier in the linear polymer chain favoring surface concentration, and prevents it from getting trapped in the bulk. While not wishing to be limited by theory, it is believed that the alkylammonium surface modifier being in the linear chain would have greater mobility and a tendency of concentrating at the surface.

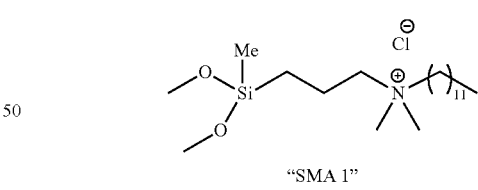

"SMA 1"

We have quantitatively generated a quaternary ammonium salt, which is a difunctional quaternary alkoxide (referred to herein as "SMA 1" or "QAM"), in a one-step reaction of the commercially available chloropropyl precursor with C12 amine. Probing the efficacy of SMA 1, 1 wt % was added to a 5 kDa PDMS diol followed by conventional condensation cure with BTSE, 8. A bacterial spray test with a 30 min exposure time gave >99% kill against Gram(−) (*P. aeruginosa, E. coli*) and Gram(+) (*S. aureus*) bacteria. Results indicate good stability in air over several months, which is surprising.

One embodiment relates to the development of new silicone antibacterial modifiers for applications such as coatings and tubing used in biomedical applications. One embodiment relies on surface concentration of betaines, a specialized family of zwitterions, comprising of cationic moiety such as quaternary ammonium species and anionic functional groups like sulfo-, carboxy-, hydroxyl-, and phosphobetaines, and the approach is introducing a group that is "self chaperoning" or self-surface concentrating into the polydimethylsiloxane (PDMS) main chain. The resulting coating or object has a contact antibacterial surface. The modified resin is suitable for a wide variety of applications including tubing, implants, breathing devices, masks, tracheal implants, and the like.

It is known that with long fluorous side chains ($\geq C_f 8$, $C_f$=perfluorinated carbon), replacement of terminal —$CF_3$ by —$CF_2H$ results in decreased surface tension. For fluoromethacrylate block copolymers having "short" side chains (<$C_f 8$) a similar reduction of $\theta_{adv}$ and $\theta_{rec}$ is observed by substituting —$CF_3$ terminated side chains with —$CF_2H$ termination. We have found that a co-repeat unit with a —$CF_2H$ side chain together with a co-repeat unit having a quaternary side chain is more stable both in dry and wet conditions and is less prone to surface phase separation.

In one embodiment, we have found that the so-called, "4FOx" (a fluorinated side chain with a —$CF_2H$ end group) instead of 3FOx, may be a more useful "chaperone" to direct the cationic antimicrobial moiety to the surface because of its amphiphilic nature.

In one embodiment, bacteria exposed to the contact kill antimicrobial surfaces described herein do not build up resistance to contact kill.

In one embodiment, the polydimethylsiloxane (PDMS) coatings and antimicrobial surfaces described herein result in a contact kill of bacteria without release of biocide.

Stepwise synthesis of surface modifying additive 'SMA 1' and its incorporation into PDMS elastomers.

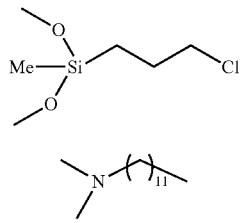

The surface modifying additive, SMA 1 is synthesized by performing a substitution reaction between the 3-chloropropyl dimethoxysilane 1 and N,N-dodecyldimethylamine 2, leading to replacement of the chlorine atom in 1 by the tertiary aminie. This substitution reaction incorporates a quaternary positive charge in the modifier which can then be reacted in varying weight percents with a PDMS elastomer. It is believed that the charge bearing quaternary ammonium groups in SMA 1 may be entropically driven to the surface producing coatings with near surface quaternised cationic moieties.

In one embodiment, synthesis of the quaternised PDMS compositions involves a two step method. The first step involves a substitution reaction between 3-chloropropyl dimethoxysilane 1, and N,N-dimethyldodecylamine 2. Step 2 involves a condensation reaction between the precursor synthesized in step 1, a crosslinking agent 3 and a low molecular weight silanol terminated PDMS.

Precursor Synthesis.

In one embodiment, SMA 1 may be made by reacting 5 g (27.4 mmol) of the chlorosilane 1 with 5.5 g (25.8 mmol) of the dodecylamine 2 in a reaction vessel at 30° C. for 48 hrs. A constant supply of nitrogen was maintained inside the reaction flask to eliminate the presence of any moisture since the methoxy functional groups present in 1 are susceptible to hydrolysis. Chlorosilane 1 was taken in excess since its high volatility enabled removal of traces of unreacted 1 under vacuum.

In one embodiment, a P-Q-C12 (a quaternised PDMS) synthesis involves reacting various wt % of the SMA1 with a silanol terminated PDMS (4 kDa), a crosslinking agent to promote the formation of a network structure. This reaction is allowed to take place in the presence of 0.5 wt % DBTDA catalyst.

In one embodiment, minuscule amount of SMA1 in the PDMS matrix will surface concentrate and confer antimicrobial characteristic to the polymer.

In one embodiment, the alkyl side chain bearing a cationic charge may be entropically driven to the surface of the polymer.

Assay for Antimicrobial Activity.

Bacterial strains of *Pseudomonas aeruginosa* PAO1 and *Staphylococcus aureus* ATCC-25904 were used for investigating the biocidal efficacy of PDMS doped with 0.5 wt % of SMA1. The bacterial cultures were streaked on Luria Agar plates from frozen stocks and incubated overnight at 37° C. A single colony from each strain was used to inoculate 6 ml of Luria Broth (LB), was grown overnight at 37° C. at 225 rpm. A starting inoculum of $10^8$-$10^9$ colony forming units per milliliter (CFU/ml) of the desired pathogen was used for the culture. Aliquots from the overnight culture were taken and reinoculated in a 1:100 dilution in LB.

A biocidal test was devised to simulate aerosol deposition (cough, sneeze) of pathogenic bacteria. With a sprayer designed to deliver a controlled volume, a challenge of *Pseudomonas aeruginosa* ($10^7$ CFU/mL) was delivered to the surface of these PDMS coatings containing 0.5 wt % of SMA1. A constant volume of 5-mg of the bacterial culture was sprayed on the coated microscope slides. The coated slides were placed in a constant humidity (85-95%) environment. A constant humidity is important for testing because control experiments in ambient air showed irreproducible fractions of dead bacteria as a function of time. After 30 min, the slides were placed in saline solution and vortexed for 2 min. One hundred microliter aliquots and dilutions were removed and spread onto agar plates that were incubated at 37° C. for 18 h. Live bacteria (cfu's) on plates were counted to obtain the percent kill and log reduction. A 30 minute residence time was chosen in order to achieve complete kill. The same protocol was followed for microscope slides coated with conventional condensation cured PDMS that served as a control.

Antimicrobial Activity of the 0.5 wt % P-Q-C12 Composition.

Biocidal efficacy of the 0.5 wt % P-Q-C12 coatings have been investigated against *P. aeruginosa* and *S. aureus* and the results have been compared with the antimicrobial activity for a conventional PDMS coated slide. One aim was also to investigate the biocidal efficacy of this quaternised PDMS composition against both Gram (+ve) *S. aureus* and Gram (−ve) *P. aeruginosa* bacteria. See FIG. 2.

For *S. aureus*, the control slide had an average of 118 and 123 cfu, whereas the 0.5 wt % PQ-C12 slides had 30 and 46 cfu respectively.

For *P. aeruginosa*, the PDMS control had 331 and 305 cfu of viable bacteria, while the 0.5 wt % PQ-C12 coated slide had 66 and 87 colonies remaining. It was observed that this surface modifier had an ~69% kill for *S. aureus* and an ~75% kill for *P. aeruginosa* strains.

Investigation of Varying the Weight Percent of the PQ-C12 Modifier on Biocidal Activity.

We have achieved a considerable antimicrobial activity by having 0.5 wt % of the modifier in the matrix. Varying the amounts of the cationic surface modifier can be correlated to the biocidal efficacy of the modified PDMS.

A 1 wt % and 2 wt % of the modifier in PDMS has been used in biocidal tests to investigate their antimicrobial effectiveness. These modified coatings were also tested against *Escherecia coli*, a Gram (-ve) bacteria, in addition to the *S. aureus* and *P. aeruginosa*.

Antimicrobial Activity of the 1 wt % and the 2 wt % P-Q-C12 Compositions.

An improvement in the antimicrobial activity of these modified PDMS coatings were observed on increasing the amount of surface modifier. A remarkable improvement in antimicrobial effectiveness has been observed going from 0.5% to 1% of the PQ-C12 surface modifier. The percent kill for *S. aureus* increased from 69% to 99.3%, similarly, 99.5 for *P. aeruginosa*. The 1% modified coatings were also very effective against *E. coli*, affecting a 97.8% kill in the first 30 minutes.

Results with the 2% modified PDMS coating has been achieved. It has been observed that the 2% modified coating affects a 98.5% kill for *S. aureus*, 99.6% for *P. aeruginosa* and 98.7% for *E. coli* strains.

Polyoxetanes:

Introduction.

FIG. 3 depicts one embodiment of our model in surface modification using P[AB]-polyurethanes. It is well known that concentration of soft blocks occur at the air-polymer interface in polyurethanes. FIG. 3b shows copolyoxetane soft blocks as P[AB] "bottle brushes". Copolyoxetane brushes have flexible main chains ($T_g$'s, −40 to −60° C.) and relatively short side chain "bristles".

Designations.

Notations for base polyurethane are typified by HMDI/BD(50)-PTMO(1000) (FIG. 3c), where HMDI is H12MDI, (4,4'-(methylene bis-(p-cyclohexyl isocyanate)), BD is 1,4-butane diol, and 50 is the wt % HMDI/BD hard block. FIG. 3a shows the 1,3-propylene oxide main chain and side chains that comprise P[AB] copolyoxetane bottle brushes, "BB". A and B (and sometimes C) side chain designations are also used for soft block repeat units. By extension, bottle brush polyurethane modifiers (BB-U) results in notations such as HMDI/BD(30)-P[(A)(B)-p:(1-p)-5.1], where P denotes ring opened structures for repeat units A and B, p is the A mole fraction, and 5.1 is the soft block $M_n$ (kDa). In ring opening polymerization, simultaneous feed of A and B monomers gives random copolyoxetanes (Scheme 1). In one embodiment, the P[AB] copolyoxetanes are random copolymers so that the designation P[AB] is used rather than P[A-r-B].

Scheme 1. Oxetane ring opening copolymerization to a P[AB] diol.

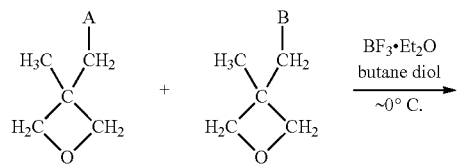

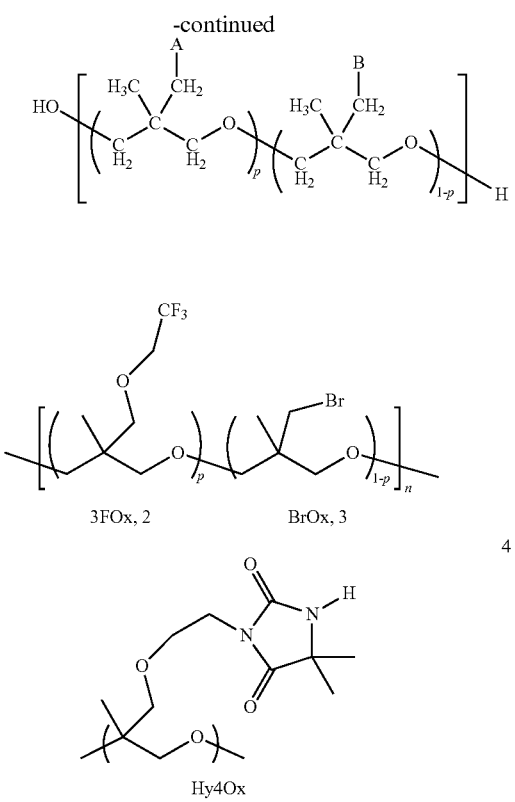

Model Polymer Surface Modifier, PSM.

A model PSM was investigated having a P[(3FOx)(BrOx)] copolyoxetane soft block (2 and 3, respectively). 3FOx was essential in that study for BrOx surface concentration. For example, with 0.5 wt % P[(3FOx)(BrOx)-1:1] polyurethane modifier, Br was 2.2 atom % by XPS, but Br was at the XPS detection limit (0.1 atom %) for a control having a P[BrOx] polyoxetane soft block. The notion of a fluorous "chaperone" for functional moiety B was thus established.

Hydantoin PSM.

The conversion of hydantoin to chloramines (—N—H→—N—Cl) by bleach results in powerful oxidative antimicrobial functionality. Chloramine functionalized surfaces (e.g., fibers) are stable in air and even to laundering. This work stimulated the preparation of a copolyoxetane with Hy4Ox 4 as a precursor to chloramine function. Surprisingly, polyurethanes with 3FOx "chaperone" A and Hy4Ox B copolyoxetane soft blocks had unprecedented wetting characteristics. The dry surface was moderately hydrophilic with 70-80° advancing contact angles ($\theta_{adv}$), while the wetted surface was hydrophobic with $\theta_{adv}$>100°. This is opposite usual behavior by which water adsorption or surface reconstruction results in decreased contact angles.

The original goal of introducing oxidative antimicrobial function was attained. Less than 2 wt % of the above PSM had surface accessible N—H convertible to chloramine (N—Cl) with dilute bleach. The coatings effected rapid 100% kill of sprayed on Gram+/- bacterial challenges.

P[(3FOx)(MEnOx)] Copolyoxetane Diols.

Both random and block [(3FOx)(MEnOx)-p:(1-p)] copolyoxetane diols were prepared. These amphiphilic diols containing PEG-like (ME3Ox or ME7Ox, Scheme 2) and 3FOx side chains were incorporated in polyurethanes (FIG. 4a). P[A-r-B] and P[A-b-B] polyurethanes were employed as PSMs for a conventional MDI/BD-PTMO base polyurethane (FIG. 4b). Surface composition (XPS), morphology (AFM) and wetting behavior for the respective P[A-r-B] and P[A-b-B] polyurethane modified base polyurethane are distinctly different.

Alkyl-Ammonium PSMs.

catheters to touch pads. Criteria were set for contact antimicrobial elastomers and coatings: (a) no biocide leaching, (b) stability in air and water and (c) unlike —N—Cl, low or no cytotoxicity.

Scheme 2. MEnOx designations.

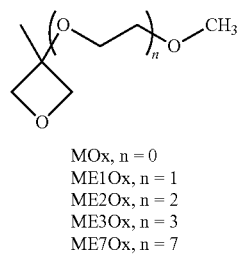

MOx, n = 0
ME1Ox, n = 1
ME2Ox, n = 2
ME3Ox, n = 3
ME7Ox, n = 7

Coating surface modification, which uses 1 or 2% PSM with a conventional "base" polymer, has important and distinguishing features that contribute to intellectual merit including (a) retention of established bulk properties for the majority polymer (FIG. 3b), (b) compositional economy that results from using the P[AB]-soft block polyurethane as a minor constituent, and (c) potential for translation to applications.

HMDI-BD(30)-P[3FOx)(C12)-87:13-6.5] 5, shown, was generated as a trial PSM. The matrix polyurethane HMDI/BD(50)-PTMO is shown in FIG. 3. In a spray test, 2 wt % PSM 5 provided 100% kill against a $10^7$ CFU/mL aerosol challenge of Gram(−) (P. aeruginosa, E. coli) and Gram(+) (S. aureus) bacteria during an exposure time of 30 min (FIG. 5b). Excellent contact antimicrobial kill was consistent with 5a surface concentration by XPS analysis.

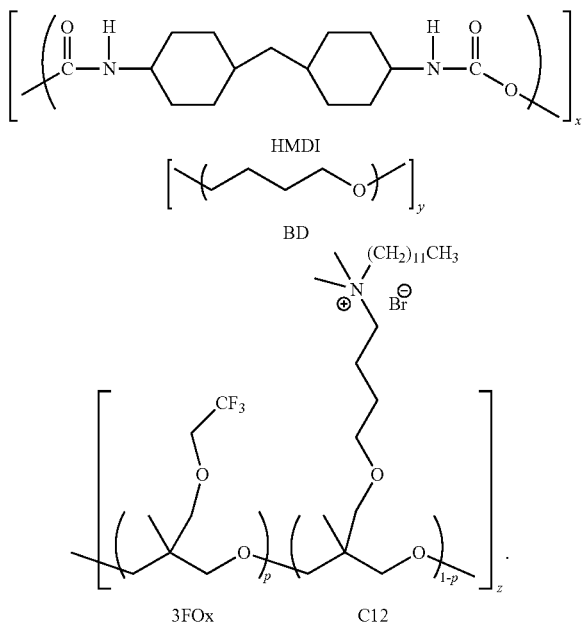

Components of HMDI-BD(30)-P[(3FOx)(C12)-86:13-M$_n$],
5 and P[AB] soft block 5a

Stability of 2 wt % PSM 5.

A series of HMDI/BD(30)-P[(3FOx)(C12)-86:13-M$_n$] modifiers with systematic changes in M$_n$ (kDa). Temporal stability of antimicrobial effectiveness was previously evaluated. Tests 2-3 days after drip coating reproduced previous results (FIG. 5b), but after two-weeks coatings gave widely varying results with 50% or less kill. A representative result for a 2 wt % HMDI/BD(30)-P[(3FOx)(C12)-86:14] modified coating after 2 weeks is shown in FIG. 5d. Longer times gave worse results.

To begin understanding loss of antimicrobial function, surface morphology was investigated by TM-AFM. 3D height images (not shown) for 2 wt % HMDI/BD(30)-P[(3FOx)(C12)-86:14] were observed as a function of time. Two days after coating, the image was observed to be almost featureless. After 2 weeks multiple 2-3 μm features up to ~500 nm high appear. After 8 weeks the surface is topologically complex with a high density of nano- and microspike features. Loss of antimicrobial effectiveness correlates with the observed surface phase separation of the HMDI/BD(30)-P[(3FOx)(C12)-86:14] modifier. The phase separated domains apparently sequester quaternary charge leading to ineffective contact antimicrobial kill.

Zeta Potentials.

Zeta potential measurements offer a direct determination of surface charge. Compared to the relatively slow deactivation of quaternary charge density in air (biotesting, AFM), streaming potential measurements indicate that water accelerates loss of surface accessible positive charge for the series of 5-modified polyurethanes (HMDI/BD(30)-P[(3FOx)(C12)-86:14]). The unexpected temporal instability of quaternary charge led to a major thrust in proposed research on stabilization strategies.

New P[AB] soft block BB-polyurethane (BB-U) modifiers with improved temporal stability are described. In one embodiment, a facile route to quat-surface concentration for condensation cured PDMS is described.

The Matrix.

In one embodiment, HMDI-BD(50)-PTMO(1000) may be used as a convenient matrix or base polyurethane. This thermoplastic polyurethane is easily prepared (50-100 g) and unlike most tested alternatives, does not confuse dynamic contact angle analysis (DCA, Wilhelmy plate) by water contamination. With a high hard block wt % HMDI-BD(50)-PTMO(1000) has a moderate strain-to-break (~400%) and a relatively high modulus (9.7 MPa).

New Bottle Brushes.

To help thwart phase separation, new BB-U surface modifiers based on two classes of P[AB] copolyoxetanes are described. Results demonstrate surface concentration without phase separation for both, and we have found that same P[AB]

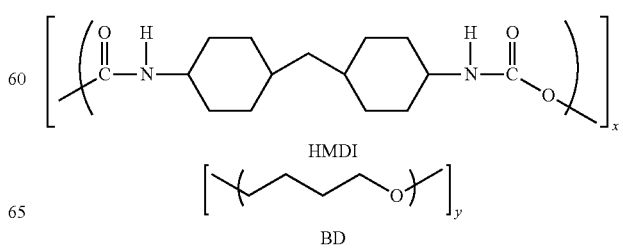

-continued

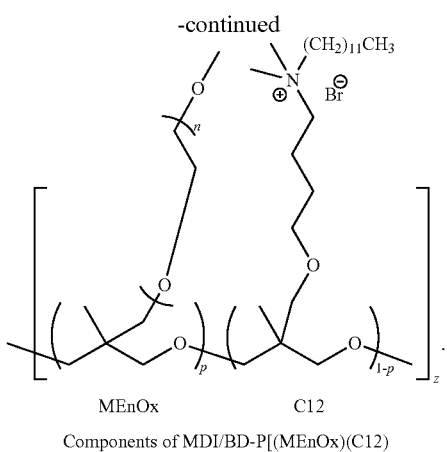

Components of MDI/BD-P[(MEnOx)(C12)]

copolyoxetane diols can be used with new bottle brush-nanoglass (BB-NG) surface modifiers described herein.

i. PEG/Alkylammonium Copolyoxetanes,

The soft block in HMDI/BD(30)-P[(ME2Ox)(C12)-0.86:0.14] is shown. This PSM was found highly effective in antimicrobial testing. At short times after coating preparation, it was nearly equivalent to the 3FOx analog 5. In this regard, the 19 atom C12 side chain acted as a "self-chaperone"; the 13 atom side chain analog "C6" was considerably less effective in biotesting.

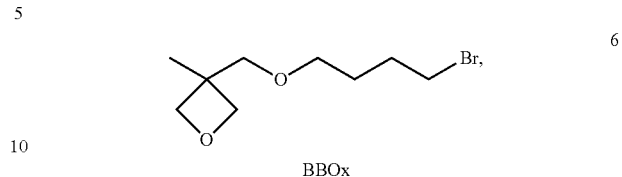

BBOx

PEG side chain length. The initial advancing contact angle ($\theta_{adv}$, DSC) for a 2 wt % blend of HMDI/BD(30)-P[(ME2Ox)(C12)-0.86:0.14] with the HMDI/BD(50)-PTMO-1000 base polyurethane (FIG. 2) was 94°, followed by a drop to 80° in the second cycle (total time ~5 min).

Quat mole fraction. C12 mole fraction can increased by increasing the BBOx 6 mole fraction in the precursor P[(ME2Ox)(BBOx)-p:(1-p)] diols. In solution, it was found that an optimum range of C12 mole fraction (0.4-0.6) was suitable for biocidal kill (lowest minimum inhibitory concentration, MIC).

In one embodiment, low MICs may be obtained for 40-60 mol % C12 in P[(ME2Ox)(C12)-p: (1-p)].

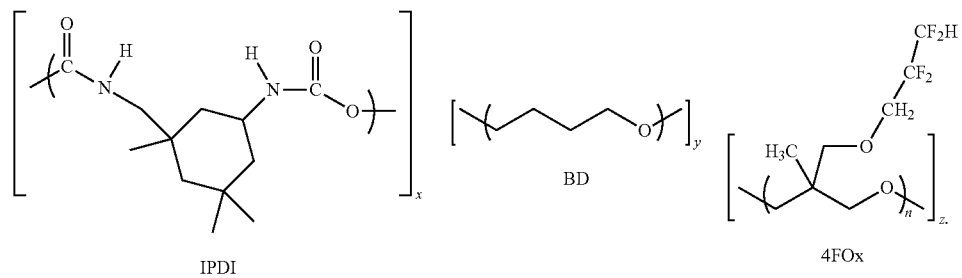

Components of IPDI/BD(40)-P[4FOx]

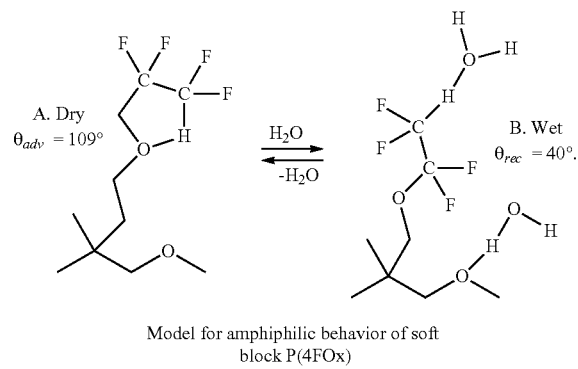

Model for amphiphilic behavior of soft block P(4FOx)

4FOx/Alkylammonium Copolyoxetanes.

With long fluorous side chains (≥$C_f8$, $C_f$=perfluorinated carbon), replacement of terminal —$CF_3$ by —$CF_2H$ results in decreased surface tension. For fluoromethacrylate block copolymers having "short" side chains (<$C_f8$) a similar reduction of $\theta_{adv}$ and $\theta_{rec}$ is observed; low contact hysteresis was attributed to above-ambient $T_g$'s.

Compared to methacrylates, completely different wetting behavior is observed for a polyurethane with the 4FOx polyoxetane soft block shown. A striking feature for IPDI/BD(40)-P(4FOx) is $\theta_{adv}$ ~108° (like —$CF_3$) but $\theta_{rec}$ ~40°, resulting in a large contact angle hysteresis ($\theta_\Delta$=68°). The model shown may account for the amphiphilic behavior of the P(4FOx) polyurethane. In air, enthalpically driven H-bonding of $CF_2H$ to ether moieties is believed to result in —$CF_2$—$CF_2$— groups dominating the surface. XPS is consistent with this view. Hydrogen bonding may account for the 40° $\theta_{rec}$.

Coatings with 2 wt % HMDI/BD(30)-P[(4FOx)(C12)-p:(1-p)] were prepared, where 4FOx to C12 ratios were 86:14 and 66:34. Zeta potentials and contact kill against PA, *P. aeruginosa*, by the spray test described herein show that the zeta potential is higher for the modifier with 34 mol % C12 (92.1 mV) compared to that for the one with 14 mol % C12 (68.2 mV). Importantly, the zeta potential was nearly the same (±1 mV) over the course of two runs for each of the two modified coatings (2×20 min≈40 min, $10^{-3}$ M KBr). In keeping with the

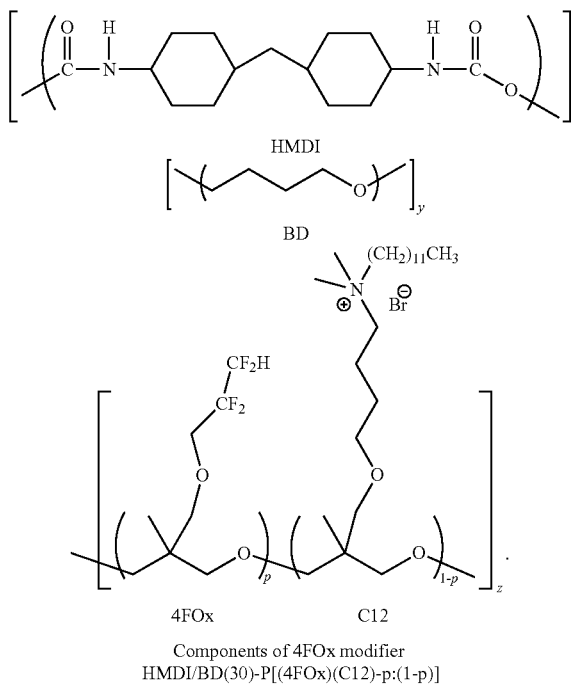

Components of 4FOx modifier
HMDI/BD(30)-P[(4FOx)(C12)-p:(1-p)]

high positive zeta potentials, high contact kill against PA was observed for both coatings.

The "bottle brush-nanoglass" (BB-NG) surface modification includes two principle components: (a) a polyoxetane BB with triethoxysilyl end groups and (b) an alkoxysilane that together with BB chain ends comprise precursors to a "nanoglass", NG phase via hydrolysis and condensation reactions.

One embodiment of the BB-NG concept is illustrated in FIG. 6 with a P[AB] copolyoxetane soft block brush (see also FIG. 2). We have found that BB-NG surface modification is broadly applicable, as any P[AB] copolyoxetane diol or other diol can be quickly and easily converted in one step to a BB 7-analog. The BB-NG concept is related to the use of glass and/or silicon wafers for growing functional thin films such as by controlled radical polymerization. For BB-NG the nanoglass domains are generated in situ from alkoxy end functionalized brushes and an alkoxysilane nanoglass precursor.

For P[AB] copolyoxetanes, P[(ME2Ox)(C12)] and P[(4FOx)(C12)] diols are easily converted to 7-analogs and in turn to modified base polyurethanes.

A conversion of P[(4FOx)(C12)-64:24] diol to a 7-analog was carried out. This reaction to form the 7-analog designated 9 is shown in FIG. 6. This was followed by (b) modification of base polyurethane (FIG. 2) with 1 wt % 9 and bis(triethoxysilyl)ethane ("BTSE") (10 wt %). Biotesting with sprayed-on *P. aeruginosa* (1 hr residence) confirmed feasibility with 100% kill. Two weeks later with tests in triplicate, 100% kill was once again realized indicating good temporal stability in air. This is surprising because (a) it demonstrates the general reaction of a P[AB] diol to form a 7-analog (namely 9) and (b) the surface modification of a conventional polyurethane "delivers" quaternary antimicrobial function that is stable with time, which is in contrast to the instability of the conventional polyurethane modifier HMDI-BD(30)-P[(3FOx)(C12)-86:13-$M_n$]. Preliminary results suggest somewhat better stability than even the much-improved 4-FOx based polyurethane modifier HMDI/BD(30)-P[(4FOx)(C12)-p:(1-p)]. In this regard, an important practical advantage is achieved by P[(4FOx)(C12)]-TES 9, which is also much simpler to prepare and has good solubility.

If desired, varying wt % of NG can be achieved with increasing increments of BTSE.

In one embodiment, the BB-NG modifier may be adapted to other polymers such as acrylates seems likely. P[(ME2Ox)(C12)]-7 analogs will be soluble in alcohol-water mixtures while 4FOx-based precursors will be soluble in alcohols.

Scheme 3. "One pot" end-capping reactions with dibutyltin diacetate catalysis giving condensation curable PDMS-3FOx-PDMS block copolymer I-3; U, urethane; UR, urea.

Eq 1

HO—P(3FOx)—OH + HDMI →

HMDI-U-P(3FOx)-U-HMDI (I-1)

Eq 2

I-1 + $H_2N(CH_2)_3$-PDMS-$(CH_2)_3NH_2$ →

[$H_2N(CH_2)_3$-PDMS-UR-HMDI]-P(3FOx)-U-HMDI_UR-PDMS-$(CH_2)_3NH_2$ (I-2)

Eq 3

I-2 + OCN—$(CH_2)_3$—$Si(OEt)_3$ →

I-2[UR-$(CH_2)_3$-$Si(OEt)_3$]$_2$ (I-3)

Surface Modification of Polydimethylsiloxane (PDMS).

Translation to applications is strongly inhibited by the presence of a $C_f$8 component that could degrade to perfluorooctanoic acid (PFOA), which is bioaccumulative. Therefore, the preparation of the hybrid triblock copolymer, PDMS-P(3FOx)-PDMS is noteworthy as a "Cf-1 modifier.

In one embodiment, the introduction of P[3FOx], 2, provides a "C$_f$1" modifier that is not a PFOA precursor.

A one pot three step reaction generates the condensation curable PDMS-3FOx-PDMS triblock I-3 (Scheme 3). Dibutyltin diacetate catalyzes urethane, urea, and condensation cure. Cured I-3 coatings show no hint of fluorous (oleophobic) surface properties. XPS and contact angles are identical to a PDMS control.

Although the condensation cured triblock I-3 has a PDMS-like surface, at low wt % I-3 triblock might modify a PDMS elastomer creating a fluorous surface. Previously, isopropanol was used to differentiate PDMS (0° contact angle) from fluorous C$_f$8 (30-80°) surfaces. In a pilot study, condensation cured PDMS coatings with 0.1-2 wt % 1-3 had contact angles of ≥20° with isopropanol as a probe liquid indicating a fluorous surface component. The contact angle decreased to 5° at 10 wt % suggesting P(3FOx) phase separation/aggregation that depletes fluorous surface concentration.

The fluorinated polyoxetanes P(3FOx) and P(5FOx) described herein may be obtained from OMNOVA Solutions, Akron Ohio.

EXAMPLES

Example 1: Polyurethane Purification

In a 60 mL vial, 30 grams of methanol and 6 grams of THF were mixed. Into the vial, 3 grams of polyurethane pellets (Lubrizol Estane ALR-E72A) was added. The mixture was then heated to 60° C. PU pellets swell to at least double their original size within one hour, which further coalesced into one piece overnight.

Every 24 hours, a sample was taken and dried under vacuum to remove solvents. A few dried pellets were soaked in clean water that was confirmed by pre-interrogation water check with flamed glass slide and dynamic contact angle (DCA, Wilhelmy plate, degrees). After at least 5 minutes of soaking the purified polyurethane pellets, the water was checked with DCA using a flamed glass slide to determine whether contamination is present (i.e., small molecule or surface active molecules leaching out of the purified polyurethane). After at least 5 minutes of soaking, a water check with DCA and flamed glass slide is done to check whether contamination is detected. Samples were checked at 24, 48, 72, and 96 hour. The results (not shown) indicate that for PU pellets soaked in methanol/THF mixture for 96 hours, water contamination is negligible after 96 hours.

Example 2: Polyurethane Purification

In a 200 mL vial, 100 grams of ethanol and 20 grams of THF were mixed. Into the vial, 10 grams of polyurethane pellets (Lubrizol Estane ALR-E72A) was added. The mixture was then heated to 30° C. PU pellets swell to at least double of its original size within 24 hours. The pellets were soaked for 2 weeks and no significant coalescence was observed. Ten pellets were taken out and dried under vacuum to remove solvents. Five dried pellets were soaked in clean water that was confirmed by pre-interrogation water check with flamed glass slide. After at least 5 minutes of soaking, a water check with flamed glass slide showed no water contamination.

Example 3: Synthesis and Characterization of Blends of HMDI/BD P[(3FOx)(C12)]

Materials
Synthesis of Monomers:
Synthesis of 4FOx: 3-Methyl-3-(2,2,3,3,-tetrafluoropropoxymethyl)oxetane, 4FOx, was synthesized by replacing Br in BrOx with fluorinated alcohols using phase transfer catalysis (TBAB). A typical synthesis involved reacting 41.25 g (250 mmol) of BrOx with 46.2 g (350 mmol) of 2,2,3,3,-tetrafluoropropan-1-ol with in presence of TBAB (5 g, 0.0125 mmol). The mixture was heated to 60° C. in 20 ml of water. KOH (15.78 g, 87%) was dissolved in water (20 ml) and added drop wise over one-hour period. This solution was then heated to 75° C. and stirred for 72 hr. The resulting 4FOx is separated from the aqueous layer using dichloromethane. The resulting dichloromethane solution was dried with magnesium sulfate and dichloromethane evaporated using a rotovap. GC-MS showed a small percentage of BrOx. Short path distillation gave 99%+4FOx monomer.

Synthesis of BBOx: The precursor to BBOx (Bromobutyl oxetane) is 3-(hydroxymethyl)-3-methyl oxetane (HOOx) which was prepared via the pyrolysis of diethyl carbonate and 1,1,1 tris (hydroxymethyl) ethane as described in the literature. BBOx was prepared from HOOx and dibromobutane via a phase transfer catalysis reaction and is also described in the literature.

Preparation of P[AB] diol: The P[AB] diol is prepared via cationic ring opening polymerization following the process described previously. Two different diols of varying 4Fox:C12 ratio were prepared to study the effect of changing the amount of quaternary ammonium on the antimicrobial properties of the surface modifier. The two different diols obtained were P[(4FOx)(BBOx)-0.86:0.14] and P[(4FOx)(BBOx)-0.66:0.34]. Molecular weights of the two diols were calculated using NMR end group analysis. These diols were then quaternized by the substitution of C—Br with N,N dimethyl dodecyl amine (C12) in acetonitrile for 18 hours. The diols are then used as soft blocks for making polyurethanes using the soft block first method, were the ratio of the hard block to soft block was 30:70 (wt/wt).

The base polyurethane was synthesized using a two-step solution polymerization, using PTMO (1000) as soft block and HMDI-BD as the hard block (50 wt %).

Preparation of Blends and Coatings:

2, 1, and 0.5 wt % blends of the surface modifier in base polyurethane were prepared. It was observed that unlike the 3FOx based P[AB] polyurethane, the 4FOx based polyurethanes were insoluble in THF. DMAC (dimethyl acetamide) was used as an alternative solvent. Blends of the PSM in DMAC and base polyurethane in THF produced fairly transparent coatings. However, over a period of 7 days, the surface modifier was observed to be phase separating out of the blends. This prompted the use of DMAC as a solvent for the entire blend. Coatings were prepared by drip coating glass slides and glass cover slips with the blend. Due to the low volatility of DMAC, the coatings had to be heated in an oven at 120° C., overnight. Transparent coatings were obtained.

Characterization:

X-Ray Photoelectron Spectroscopy: XPS spectra were studied for both 4FOx and 8FOx Polyurethanes. The measurements were carried out on the Thermo Fisher Scientific ESCALAB 250 "X-ray Photoelectron spectrometer". This instrument has monochromatized Al K α X-ray and low energy electron flood gun for charge neutralization. X-ray spot size for these acquisitions was on the order of 500 mm. Pressure in the analytical chamber during spectral acquisition was less than 2×10-8 Torr Pass energy for survey spectra was 150 eV. The take-off angle was 90°. The data were analyzed with the Thermo Avantage software (v4.40).

Samples of 2, 1 and 0.5 wt % blends were cut and attached to the sample holder using carbon tape.

Atomic Force Microscopy: Morphological analyses of polyurethane surfaces were carried out using a Dimension-3100 (Digital Instruments, CA) atomic force microscope with a NanoScope V controller. Imaging was performed in tapping mode using a microfabricated silicon cantilever (40 N/m, Veeco, Santa Barbara, Calif.) in air. Images were analysed using the Nanoscope v710 software.

Zeta Potential: The electrokinetic analyzer in surface analysis or SurPASS from Anton PAAR was used to investigate the zeta potential of the coated surfaces based on a streaming potential and streaming current measurement. The Zeta Potential is measured using the Helmholtz-Smoluchowski method.

Bactericidal Test: Bacterial spray testing has been used in other studies of non-leaching biocidal materials and was used herein to determine biocidal activity of the P[(4FOx)(C12)] PSM blend.

Agar plates were streaked with the desired bacteria from a stock culture kept frozen at −70° C. and incubated at 37° C. for 18-24 hrs. From this plate a single colony was collected and used to inoculate 10 mL of luria broth. This culture solution was incubated for 18-24 hrs at 37° C. After incubation, the 1:50 dilution of the culture was prepared and incubated at 37° C. until an optical density of 0.2-0.3 was observed for 1 mL of culture. Once the desired optical density has been achieved, the culture solution is used in bacteria challenges.

A biocidal test was devised to deposit the bacterial solution via an aerosol spray. Using as stock bacteria concentration of $10^6$ colony forming units (CFU)/mL, slides coated with 2 wt % and 1 wt % PSM blends where spray for 1 second and weighed to determine the amount of bacteria solution deposited. Sprayed slides were then placed in a constant humidity (85-95%) environment. Keeping the samples at constant humidity is important because control experiments in ambient air showed irreproducible fractions of dead bacteria as a function of time which is likely to the bacteria experiencing osmotic shock. After 60 min, the slides were placed in saline solution and vortex stirred for 2 min. One hundred microliter aliquots and (×10) dilutions were removed and spread onto agar plates that were incubated at 37° C. for 18 h. After incubation, bacteria colonies were counted to obtain the percent kill.

Results and Discussion:

We have developed antimicrobial polymeric coatings without affecting the bulk properties of the polymer which retain their antimicrobial properties over a period of time. All the samples were studied for changes in morphology both immediately after coating and also four weeks after coating. The results obtained would be an indicator of how the coatings would perform in real life conditions. Quantifying surface accessible charge of 3FOx based polyurethane coatings by the microfluidic capillary method has shown that a 2 wt % coating of HMDI/BD(30)-P[3FOx)(C12)-86:14] had a sharp fall in the surface accessible positive charge within 80 seconds. This had explained the loss in antimicrobial properties of the 3FOx based coatings when tested after two weeks of preparing the coatings.

X-ray Photoelectron Spectroscopy:

The coatings of the blends were studied by XPS to understand the surface composition. A survey spectrum for each of the blends confirmed the presence of carbon, oxygen, fluorine and nitrogen. Table 1 gives comparison between the calculated and observed atom percentages of the four elements. The calculated percentage assumes 100% surface modifier soft block on the surface.

Zeta Potential measurements: 2 wt % blends of both HMDI/BD(30)-P[(4FOx)(C12)-66:34-5.7] and HMDI/BD(30)-P[(3FOx)(C12)-86:14-4.2] were prepared and tested for their zeta potential values. The results obtained are summarized in Table 2.

TABLE 1

Calculated vs observed atom percentages of 0.5, 1 and 2 wt % blends of surface modifier.

| | No of atoms in soft block | Calculated atom % | Observed atom % Surface modifier percentage in blend 0.5 | 1 | 2 |
|---|---|---|---|---|---|
| C | 13.1 | 72% | 67% | 68% | 65% |
| O | 2 | 11% | 20% | 21% | 19% |
| F | 2.64 | 15% | 10% | 9% | 13% |
| N | 0.34 | 2% | 3% | 3% | 3% |

We found that increasing the percentage of C12 in the polyurethane imparted a higher positive charge on the surface. Antimicrobial tests were also carried out on these two coatings and the results showed that while the HMDI/BD(30)-P[(4FOx)(C12)-66:34-5.7] showed a 100% kill of bacteria, HMDI/BD(30)-P[(3FOx)(C12)-86:14-4.2] caused 90% kill. Based on these preliminary data, detailed Zeta Potential measurements were carried out for 2, 1 and 0.5 wt % blends of HMDI/BD(30)-P[(4FOx)(C12)-66:34-5.7]. The results obtained are summarized in FIG. 7.

TABLE 2

Zeta potentials for 2 wt % HMDI/BD(30)-P[(4FOx)(C12)-p:(1-p)]

| p | 1-p | ζ (mV) |
|---|---|---|
| 86 | 14 | 68.2 |
| 66 | 34 | 92.1 |

The results show a very clear distinction in the surface accessible positive charge for the 2, 1 and 0.5 wt % of the blends. It is believed that the fluorous side chain of the soft block acts as a chaperone for the quaternary ammonium side chain to be on the surface, hence, increasing the amount of C12 increases the positive charge on the surface. A surprising observation is that the 2 wt % blend gives positive zeta potential values even after 3 hours of exposure to the electrolyte. This is a significant improvement over what had been previously observed for the 2 wt % coatings of HMDI/BD(30)-P[(3FOx)(C12)-86:14].

The coatings were again tested after 4 weeks to see if they had lost the surface accessible positive charge. The results are summarized in FIG. 8.

Atomic force microscopy—To understand the surface morphology with changing surface modifier concentration, TM-AFM images of 0.5 wt %, 1 wt % and 2 wt % blends were obtained. The images were obtained at a setpoint ratio of 0.9 and an area of 25 μm×25 μm was investigated. The images (not shown) were obtained within one week of coating of the samples. It was observed that surface roughness increases with increasing percentage of surface modifier in the blend. In previous studies of evolving surface morphologies of HMDI/BD(30)-P[3FOx)(C12)-86:14], it was shown that not only does the surface phase separates within three to four days of preparing the coatings, but the phase separation is extremely dynamic with micropeak like features appearing and multiplying on the surface over a period of time, and within 8 weeks of coating the surface is completely covered with these features.

To analyze the surface stability of the new coatings, the samples were investigated under similar conditions and the images obtained (not shown) show no significant change in the surface morphology over time, which is surprising.

Antimicrobial tests: Antibacterial tests were performed on the three different concentrations of the blend. The results are shown in FIGS. 9 and 10.

Example 4: Blends of P[4FOx:C12-66:34] Diol BTSE Hybrid

Polymer surfaces modified with polyurethanes containing P[3FOx):(C12)m:n] polyoxetane soft blocks (where 3FOx is a trifluoroethoxy side chain and C12 is the quaternary ammonium containing side chain) have the ability to kill bacteria via non-leeching contact kill. However, further research showed the dynamic nature of these surfaces and the antimicrobial property was found to be diminished over time. Streaming potential studies on these surfaces showed the rapid lowering of surface accessible positive charge from 140 mv to 85 my within a period of 80 seconds for a 2 wt % blend. Changing the fluorinated side chain from a —$CF_3$ group to a —$CF_2CF_2H$ group was found to be an effective solution for increasing the stability of the positive charge on the surface. It was however observed that although the change in the fluorinated side chain remarkably improved the surface stability of positive charge, it did not completely "lock" the positive charge on the surface. Zeta potential studies showed the diminishing positive charge of about 10 mv over a period of 3 hours for a 2 wt % blend of polymer surface modifier with base polyurethane. The antimicrobial property, which was excellent (100% kill) for surfaces tested within 1 week of preparation of the blend, was found to be reduced over a period of one month. Hence a simple modification of the surface was tested to stabilize the charge on the surface by restricting the movement of the side chains. Guided by the fact that surface modifier polyurethanes made from P[(4FOx)(C12)-66:34] showed good antimicrobial properties, it was decided to test the concept with the same diol.

Experiment:

Materials: P[4FOx:C12-66:34] diol was prepared according to the method discussed earlier. 3-isocyanatopropyltriethoxysilane (SII 6455) and bis(triethoxysilyl)ethane (SIB 1817, BTESE) were purchased from Gelest, Inc. Dibutyltin diacetate was used as a catalyst and was purchased from Aldrich. Tetrahydrofuran, 99.6%, (for analysis ACS, stabilized with BHT) was obtained from Acros.

The reaction takes place in two steps:

FIG. 11 gives a schematic of step 1 of the preparative procedure:

In step 1, the diol is end-capped with isocyanatopropyltriethoxysilane. A 1:2 molar ratio of diol and the silane is used as the reactant. A solution of isocyanatopropyl triethoxysilane in THF was prepared in a 100 ml round bottom flask in the presence of DBTDA (0.5 wt %) catalyst (Solution A). The solution of the diol in THF was added dropwise to solution A under dry nitrogen purge. The disappearance of the isocyanate peak was studied at intervals to ensure 100% endcapping of the diol.

Step 2 includes of preparation of three different blends of the endcapped diols with base polyurethane. In the first step, calculated quantities of the end capped diol is added to an alkoxysilane (BTSE). The latter, together with end caps are precursors to the "nanoglass" domain via hydrolysis and condensation reaction. The solutions were then added to a 20 wt % solution of base polyurethane in THF.

Three different blends of base polyurethane with 0.5, 1 and 2 wt % endcapped diol were prepared. 10 wt % BTSE was added in each case.

Base polyurethane for this reaction was synthesized using a two-step solution polymerization, using PTMO (1000) as soft block and HMDI-BD as the hard block (50 wt %).

Coatings with the resulting solution were prepared within 15 min of Step 2. Microscope slides and glass cover slips were drip coated for zeta potential, AFM measurements and antimicrobial tests respectively. Dip coated slides were prepared for studying wetting behavior of samples via dynamic contact angle measurements.

Cure was overnight at ambient temperature followed by 100° C. for 24 hr.

Zeta Potential measurements: The electrokinetic analyzer in surface analysis or SurPASS from Anton PAAR was used to investigate the zeta potential of the coated glass slides based on a streaming potential and streaming current measurement. The electrolyte used was 0.1 mmol NaBr solution. The choice of electrolyte was governed by the presence of a common anion ($Br^-$) in the polyurethane so that secondary factors such as anion exchange do not interfere with the results.

Bactericidal Test: Bacterial spray testing has been used in other studies of non-leaching biocidal materials and was the used to determine biocidal activity of the P[(4FOx)(C12)] PSM blend.

Agar plates were streaked with the desired bacteria from a stock culture kept frozen at −70° C. and incubated at 37° C. for 18-24 hr. From this plate a single colony was collected and used to inoculate 10 mL of Luria broth. This culture solution was incubated for 18-24 hr at 37° C. After incubation, the 1:50 dilution of the culture was prepared and incubated at 37° C. until an optical density of 0.2-0.3 was observed for 1 mL of culture. Once the desired optical density has been achieved, the culture solution is used in bacteria challenges.

A biocidal test was devised to deposit the bacterial solution via an aerosol spray. Using as stock bacteria concentration of $10^6$ colony forming units (CFU)/mL, slides coated with 2 wt %, 1 wt % and 0.5 wt % blends where sprayed for 1 sec and quickly weighed to estimate the amount of bacteria solution deposited. Sprayed slides were then placed in a constant humidity (85-95%) environment. Keeping the samples at constant humidity is important because control experiments in ambient air showed irreproducible fractions of dead bacteria as a function of time which is likely to the bacteria experiencing osmotic shock. After 60 min, the slides were placed in saline solution and vortex stirred for 2 min. One hundred microliter aliquots and (×10) dilutions were removed and spread onto agar plates that were incubated at 37° C. for 18 h. After incubation, bacteria colonies were counted to obtain the percent kill.

Results and Discussion:

Atomic Force Microscopy:

A study of the topology and morphology provides an idea of the extent of phase separation, if any, of the blends and hence can provide important information about their performance over a period of time. Images (not shown) were taken at a setpoint ratio ($r_{sp}$) of 0.9 with a scan size of 25 μm. Two sets of images were studied to observe the change in the morphology of the surfaces with time. Images of surfaces of the blends obtained within 1 wk of coating indicated near surface phase separation for all the three blends with the 1 wt % blend exhibiting maximum roughness. The size of phase separated features is observed to be increasing with the increase of the percentage of surface modifier in the blend.

X-Ray Photoelectron spectroscopy: Elemental composition of the surface was studied with the help of X-Ray photoelectron spectroscopy. Table 3 with the calculated and observed percentages of the elements is given below. The calculated percentage assumes 100% of the fluorinated diol to be on the surface irrespective of the composition of the blend.

TABLE 3

Calculated vs observed atomic percentages of elements on the surface of blends

| | Calculated composition (at %) | | Observed composition of blends (at %) | | |
|---|---|---|---|---|---|
| | Soft Block only | Hybrid | 0.5 | 1 | 2 |
| O | 11.06 | 19.4 | 25.97 | 20.74 | 23.29 |
| C | 72.46 | 58.48 | 56.85 | 63.42 | 59.03 |
| F | 14.6 | 7.32 | 4.64 | 6.97 | 8.55 |
| Si | 0 | 8.31 | 11.6 | 7.39 | 7.41 |
| N | 1.88 | 6.49 | 0.94 | 1.48 | 1.73 |

From the above data it is observed that the observed percentage of nitrogen is lower than the calculated amount. It is also observed that increasing the percentage of the surface modifier diol increases the availability of nitrogen on the surface.

Zeta Potential:

Measuring and relating surface accessible positive charge to the antimicrobial property of a blend is a unique and much less time consuming process that helps assess not only the bactericidal property of a blend but also the durability of the blend. The presence of quaternary ammonium on the surface was already confirmed by XPS. Stability of the positive charge on the surface was studied by analyzing the surface by continuous flow of electrolyte for a period of 3 hours. The results are shown in FIG. 12.

The zeta potential values show excellent stability of the blends over time. For the 2 wt % blend the zeta potential remains almost constant for a period of three hours within which eight individual runs of 2 cycles each were carried out. Zeta potential increases about by about 7 mV for 1 wt % blends while the 0.5 wt % blend proves to be only slightly better than a control sample of base polyurethane. This explains the absence of measurable quaternary ammonium nitrogen for the 0.5 wt % blend as observed by XPS.

Example 5: Quaternary Ammonium Modified Silicones

Materials.

Hydroxyl terminated polydimethylsiloxane (DMS-S21, 90-120 cSt, 4 kDa), 3-chloropropylmethyldimethoxysilane (SIC 2355) and bis(triethoxysilyl)ethane (SIB 1817, BTESE) were purchased from Gelest Inc. N,N-dodecyldimethylamine (C12) and dibutyltin diacetate were obtained from Aldrich. Tetrahydrofuran, 99.6%, (for analysis ACS, stabilized with BHT) was obtained from Acros. Modified fumed silica nanoparticles (T-FSN, Cab-o-sil T5530 HMDZ treated fumed silica) having a BET surface area of 200 $m^2/g$ was generously provided by Quantum Silicones, Midlothian, Va.

Quaternary Ammonium Modifier (QAM/SMA 1) Synthesis.

With reference to FIG. 13, synthesizing the modifier involves a single step. A substitution reaction occurs between 3-chloropropylmethyldimethoxysilane 1 and N,N-dodecyldimethylamine 2 to incorporate the quaternary charge.

A typical precursor synthesis involves reacting 5 g (27.4 mmol) of reactant 1 with 5.5 g (25.8 mmol) of the tertiary amine 2 in a reaction vessel at 30° C. for 48 hrs. The reaction was carried out in the presence of ~25 ml of THF as a solvent. A constant purge of dry nitrogen was maintained inside the reaction vessel to eliminate the presence of any moisture since the methoxy functional groups present in 1 are susceptible to hydrolysis. The reaction of 1 with 2 provided the QAM 3 in quantitative yield. A complete substitution of the chlorine atom by the C12 tertiary amine was characterized by $^1$H-NMR and FT-IR spectroscopy. The modifier was stored below room temperature inside a properly vacuum sealed container to prevent hydrolysis of the alkoxy functional groups.

Coating Preparation.

Coatings were prepared on microscope slides by adding varying weight percents of the QAM to a silanol terminated PDMS following a condensation cure. PDMS coatings with 0.5%, 1% and 2% (by weight) of the modifier were prepared for further characterization. The modified coatings have been designated as P-x, where, 'P' stands for the 4 kDa poly(dimethylsiloxane) and 'x' refers to the wt % of the surface modifier incorporated in the coating. Preparation of a typical 0.5 wt % modified PDMS (P-0.5) coating involves adding 0.025 g of the QAM 3 to 5 g of a 4 kDa silanol terminated PDMS. The resin was mixed in high shear equipment (Speed Mixer) at 2700 rpm for 4 times at 60 seconds/cycle. A transparent, homogenous resin was obtained to which 0.25 g (5 wt %) of the crosslinker, BTESE along with 0.5 wt % of DBTDA catalyst was added. The resulting resin was again mixed in high shear equipment at 2700 rpm for 3 times at 60 sec/cycle. Microscope slides were drip coated with the resin and was kept at ambient (~25° C.) overnight to initiate the formation of crosslinks. The condensation cure process was driven to completion by keeping the coated microscope slides at 100° C. for 24 hr. Plaques were formed by pouring the resin into PTFE plates and following the same curing technique (FIG. 14).

A representative PDMS coating reinforced with 10 wt % of fumed silica nanoparticles was synthesized to investigate the effect of adding fillers on surface and bulk properties. Treated fumed silica nanoparticles (0.5 g, 10 wt %) was added to 5 g of the 4 kDa poly(dimethylsiloxane) and mixed in a high shear equipment at 2700 rpm for 60 sec. The cycle was repeated for 4 more times to obtain a homogenous resin. The remaining process is identical to that described in the above paragraph. These samples are designated as PR-x, where 'PR' stands for reinforced PDMS and 'x' denotes the wt % modifier.

Characterization.

Infrared Spectroscopy.

FT-IR spectra were obtained using a Nicolet 400 FT-IR spectrometer. A background spectrum was taken before running each sample and 32 scans were taken from 500 to 4000 cm-1. The spectra were analyzed using Omnic software.

NMR Spectroscopy.

$^1$H-NMR (Varian Mercury 300, 283 MHz) spectra were used to qualitatively confirm the complete substitution of the chlorine atom from 1, followed by quaternisation. Spectrum for QAM samples dissolved in chloroform-d was obtained for 32 scans.

Antimicrobial Assay.

Bacterial strains of *Pseudomonas aeruginosa* (PAO1), *Staphylococcus aureus* (ATCC-25904) and *Escherichia coli* (DH5α) were used for investigating the biocidal activity of P-0.5, P-1 and P-2 coatings. Condensation cured PDMS elastomer (P-0) was used as a control for this study. Bacterial cultures were streaked on Luria Agar plates from frozen stocks and incubated overnight at 37° C. A single colony from each strain was used to inoculate 6 ml of Luria Broth (LB) and grown overnight at 37° C., 225 rpm. A starting inoculum of $10^8$-$10^9$ colony forming units per milliliter (CFU/ml) of the desired pathogen was used for the culture. Aliquots from the overnight culture were taken and reinoculated in LB in a 1:100 dilution.

A biocidal test was devised to simulate aerosol deposition (cough, sneeze) of pathogenic bacteria. With a sprayer designed to deliver a controlled volume (or weight), a challenge of the bacterial culture (~$10^7$ CFU/mL) was delivered to the surface of the coated samples. A constant weight of ~6 mg of the bacterial culture was sprayed on the coated microscope slides. The coated slides were placed in a humidified chamber (85-95%) environment, since a constant humidity is important because control experiments at ambient air showed irreproducible fractions of dead bacteria as a function of time. This step anticipates future studies for estimating kill kinetics. After 30 mm residence time, the slides were placed in saline solution and vortexed for 2 mm. An 100 µl aliquot and a 1:100 dilution were removed and spread onto agar plates that were incubated at 37° C. for 18 h. Live bacteria (cfu's) on plates were counted to obtain the percent kill and log reduction. The same protocol was followed for microscope slides coated with conventional condensation cured PDMS that served as a control for this study. Kinetics of kill was determined by altering the residence time to 15 and 45 min.

Mechanical Test.

For tensile testing, samples were stamped out of cast plaques, which were measured for thickness, width and gauge prior to mounting in the RSA III tensile clamps. Data acquisition rate was 1 Hz while the initial sample elongation rate was 10 mm/min. The maximum elongation at break was determined for different samples.

Results and Discussion.

Quaternary Ammonium Modifier (QAM) Synthesis.

The QAM was synthesized by following a substitution reaction between 3-chloropropylmethyldimethoxysilane 1 and N,N-dodecyldimethylamine 2 leading to quaternization of the ammonium moiety. The presence of alkoxy functional groups in 1 increases its susceptibility towards hydrolysis. As a preventive measure, both inner and outer walls of the reaction vessel were properly flamed to eliminate the presence of any adhered water molecules. The reaction was carried out in a moisture controlled environment by having a continuous supply of dry nitrogen through the reaction vessel. Generally, a quaternisation reaction is performed at higher temperatures (~60° C.), but this reaction was carried out at a temperature close to ambient (~30° C.) in order to protect the methoxy groups from hydrolysis.

Formation of the quaternary ammonium modifier was monitored and confirmed by $^1$H-NMR and IR spectroscopic analysis.

Coating Preparation.

As shown in FIG. 14, coating preparation involved condensation cure reaction between: (1) PDMS and QAM, (2) PDMS and BTESE (crosslinking agent) and between BTESE moieties themselves. Low weight percent modifier (0.5%, 1% and 2%, by weight) were used in the coatings. FIG. 14 demonstrates a condensation cure technique, where water is both a reactant and a product. The surface modifier was physically mixed with the hydroxyl terminated PDMS, which ensured incorporation of the modifier in the linear siloxane chain due to its difunctional methoxy groups. To further facilitate formation of crosslinks, an additional amount of BTESE (5 wt %) was added. Condensation reaction proceeds in the presence of trace amounts of catalyst, DBTDA (0.5 wt %) to form a slightly viscous resin. Microscope slides were drip coated and kept in the ambient overnight to initiate the formation of crosslinks. Finally, the condensation reaction was driven to completion by placing the slides at 100° C. for 24 hour. The resultant coatings were optically transparent.

Antimicrobial Assay.

Having established the presence of positive charges at the polymer-air interface, the antimicrobial activity of these coatings was investigated against both Gram positive and Gram negative strains of bacteria. Antimicrobial activity of the modified samples was tested for a residence time of 30 min. As compared to the control (P-0) which had 118 and 331 cfu for *S. aureus* and *P. aeruginosa* respectively, P-0.5 showed biocidal activity by affecting 68% kill against *S. aureus* and 75% against *P. aeruginosa* in 30 min. Increasing the amount of surface modifier to 1% (for P-1) led to an enhancement in biocidal activity to 99.5% (SA), 99.6% (PA) and 98% (EC) as seen in FIG. 15. Within experimental error, the same extent of bacterial kill was achieved on increasing the amount of QAM to 2% (P-2). Log reductions in bacterial cfu's follow the same trend, with the P-1 having comparatively higher values than P-2 for all three strains (FIG. 15).

The biocidal test result complies well with the observed streaming potential measurements, where P-2>P-1>P-0.5>P-0. It is believed that increasing the weight percent of the quaternary ammonium surface modifier leads to an increase in the fraction of cationic groups at the surface, which would translate to an enhanced biocidal activity. In the present study, the biocidal activity increased from P-0.5 to P-1 whereas, and increasing the concentration of the surface modifier from 1% to 2% (P-2) affects the same extent of bacterial kill (FIG. 15). The results demonstrate that an optimum biocidal activity is achieved at a modifier concentration of 1% (P-1), after which the antimicrobial effectiveness stabilizes even though there is an increase in the surface charge density.

FIG. 16 shows the remnant number of bacterial CFUs from antimicrobial assays performed on different modified coatings and the control.

Kill kinetic assay was performed in order to determine the dependence of biocidal activity on residence time. A representative P-1 coating affected >99% kill on strains of SA, PA and EC in the first 15 min (FIG. 17). The P-1 coatings show remarkable biocidal activity as compared to the quaternized silanes which reach a 99% kill for a time >45 min. The remnant number of bacterial CFUs after the kill kinetic assay are shown in FIG. 18.

Antimicrobial tests were also performed on the filled PDMS sample modified with 1 wt % of the QAM. Biocidal activity of the 1 wt % modified PDMS sample decreased on adding filler (10 wt % FSN, fumed silica nanoparticles) (FIG. 16). The percent kill ranges from 78% (PA) to 81% (EC), which is ~20% less than the unfilled sample and there was a decrease in the log reduction by a factor of 3 (FIG. 19). It is believed that a condensation reaction occurs between the hydroxyl moieties at the surface of silica nanoparticles and the methoxy functional groups present in the QAM. This leads to FSN surface modification and subsequent internalization of the quaternary charge, rendering the surface with a lesser concentration of cationic charge. Silica nanoparticles may be treated with hexamethyldisilazane to incorporate a trimethylsilyl group at the surface, facilitating good particle dispersion. Although, in the process of silylation, a certain fraction of nanoparticle surface may remain unmodified.

From the present result it is believed that for PR-1 (filled PDMS), a condensation reaction takes place at the surface of the nanoparticle between fractions of remnant hydroxyl groups and the methoxy groups of the modifier. Immobilization of the modifier at the nanoparticle surface leads to internalization and their concentration at the surface of the coating would diminish.

Mechanical property. Polydimethylsiloxane elastomers are well known for their low glass transition temperatures ($T_g \sim -120°$ C.) and high thermal stability (~250° C.). Fumed silica nanoparticles (FSN) treated with hexamethyldisilazane were used as filler for the present study.

Tensile tests were done on an unfilled PDMS sample with 1 wt % of the QAM was (control) and a sample filled with 10 wt % of the treated FSN. The unfilled sample had a tensile behavior similar to a PDMS elastomer, with a maximum elongation of 45% at break. The filled sample underwent 250% elongation before break (FIG. 20).

Conclusion.

The present study has shown a new route for synthesizing thermosetting siloxane-based elastomers having antimicrobial activity. Small amounts (0.5, 1 and 2 wt %) of a surface modifier has been added to a PDMS matrix, following a condensation reaction to concentrate positive quaternary charges at the coating surface. Streaming potential (SP), an effective engineering technique has been utilized in this study to quantify the surface accessible quaternary charge in the modified coatings. Streaming potential measurements have shown a modifier concentration dependant charge density, with the SP increasing from P-0 (unmodified control) to P-2. Antimicrobial assays have demonstrated remarkable biocidal activity for the P-1 and P-2 coatings against strains of *S. aureus, P. aeruginosa* and *E. coli*, achieving >99% kill in 30 min. Kinetics of kill was investigated for the P-1 coatings, where they were observed to affect >99% kill in the first 15 min. Weak mechanical property of PDMS led to reinforcing a representative P-1 coating with 10 wt % of treated fumed silica nanoparticles. An improvement in tensile property was observed with an increase in elongation at break from 45% (P-1) to 250% (PR-1). Adsorption of the modifier at the nanoparticle surface led to internalization and a decrease in surface potential and biocidal activity. Biocompatibility of PDMS combined with antimicrobial activity would offer immense potential for their use in biomedical applications.

Example 6: Synthesis and Characterization of DAPMDS-PDMS-PS

Materials 1,3-Propanesultone (1,3-PS) was purchase from Sigma Aldrich. Dibutyltindiacetate (DBTDA), N,N-Dimethyl-3-aminopropylmethyldimethoxysilane (DAPMDS), silanol terminated polydimethylsiloxane (HO-PDMS-OH), 1,2-bis (triethoxysilyl)ethane (BTSE), tetrahydrofuran (THF) were purchased from Gelest and used without further purification. The microslides (25×75 mm, 1.0 mm thickness) used in this work were purchased from VWR.

Synthesis of DAPMDS-PDMS-PS

The synthetic route of DAPMDS-PDMS is presented in FIG. 21. N,N-Dimethyl-3-aminopropylmethyldimethoxysilane (0.01 mol) and silanol terminated PDMS (MW=500-700; viscosity=25 cSt; 0.02 mol) were added to a 100 mL round bottomed flask in the presence of 0.5% catalyst, DBTDA, and stirred under nitrogen atmosphere overnight at room temperature. The DAPMDS contains methoxide groups which easily hydrolyze to silanol groups, thereafter condensing with the silanol groups on the PDMS (25 cSt). At the end of the reaction, methanol formed during the reaction was removed under vacuum and the intermediate compound DAPMDS-PDMS was obtained.

The synthetic route of DAPMDS-PDMS-PS, modifier, is presented in FIG. 22. 1,3-propane sultone (0.01 mol, 1,3-PS, dissolved in ~5 mL THF) was added to the stirred reaction intermediate from step 1 and left to reflux at 50° C. overnight. THF was removed by rotary evaporation followed by thorough removal of residual solvent under vacuum.

Preparation of Coating Finished with Modifier, DAPMDS-PDMS-PS

DAPMDS-PDMS-PS (2.0 wt %) and silanol terminated PDMS (1,000 cSt) were introduced into a speed-mixer vial in the presence of 25 L DBTDA, and speed-mixed for a cycle of 60 sec at 2700 rpm. At the end of the cycle, 0.5 wt % BTESE, cross-linker, was added into the vial then speed-mixed under the same mixing condition. Under cure conditions, the silanol groups on the modifier, HO-PDMS-OH and BTESE co-condense. The surface concentration of DAPMDS-PDMS-PS imparts antimicrobial activity to the coating. Control samples were prepared following a similar procedure except without the addition of modifier.

Application of Coating on Glass Slides

The finished resin was swiftly applied to glass slides to prevent premature curing while ensuring an even distribution over the surface. Any air bubbles formed during the drip-coating process were eliminated. When drip-coating was over, the glass slides were transferred into the oven at 80° C. for 24-48 h. A similar procedure was followed for the control samples. When the curing was done, the antimicrobial activity of the coating was assessed.

Results and Discussion $^1$H NMR Analysis

NMR spectra was observed for the starting materials (DAPMDS and PDMS-25 cSt) through the synthesis of the intermediate compound, DAPMDS-PDMS and confirmed the reaction between the two starting materials and the formation of modifier, DAPMDS-PDMS-PS.

Antimicrobial Properties of Coating

The antimicrobial activities of coating finished with modifier were evaluated. The coating without the modifier was employed as a control. Bacterial colonies were allowed to grow on the surface of the coating on the glass slides. The antimicrobial activity was assessed according to their antimicrobial rate. FIG. 23 shows the antimicrobial activity of coating against *P. aureus* in parallel with the control. The results show a marked decrease in the bacterial viable colonies after 30 min contact of a sprayed on bacterial challenge. Up to 94% kill was found for *P. aureus*.

The entire contents of each of U.S. Provisional Application Ser. No. 61/457,977, filed Jul. 26, 2011; and 61/487, 991, filed May 19, 2011; and International Application No. PCT/US12/48425, filed Jul. 26, 2012 are hereby incorporated by reference.

This application is based on and claims priority to U.S. Provisional Application Ser. No. 61/552,452, filed Oct. 27, 2011, and 61/552,454, filed Oct. 27, 2011, the entire contents of each of which are hereby incorporated by reference.

The entire contents of each of the following articles are hereby incorporated by reference:

(1) Makal, U.; Uslu, N.; Wynne, K. J. Water Makes It Hydrophobic: Contraphilic Wetting for Polyurethanes with Soft Blocks Having Semifluorinated and 5,5-Dimethylhydantoin Side Chains, *Langmuir* 2007, 23, 209

(2) Wynne, K. J.; Makal, U.; Kurt, P.; Gamble, L. Model Fluorous Polyurethane Surface Modifiers Having Copolyoxetane Soft Blocks with Trifluoroethoxymethyl and Bromomethyl Side Chains, *Langmuir* 2007, 23, 10573.

(3) Zheng, Y.; Zhang, W.; Gupta, M.; Kankanala, S.; Marks, C.; Carpenter, E.; Carroll, K.; Wynne, K. J. Poly(bis-2,2, 2-trifluoroethoxymethyl oxetane): Multiple Crystal Phases, Crystallization-Induced Surface Topological Complexity and Enhanced Hydrophobicity, *J. Polym. Sci. Pt. B-Polym. Phys.* 2010, 48, 1022.

(4) Kurt, P.; Gamble, L. J.; Wynne, K. J. Surface Characterization of Biocidal Polyurethane Modifiers Having Poly(3,3-substituted)oxetane Soft Blocks with Alkylammonium Side Chains, *Langmuir* 2008, 24, 5816.

(5) Gupta, M. L.; Brunson, K.; Chakravorty, A.; Kurt, P.; Alvarez, J. C.; Luna-Vera, F.; Wynne, K. J. Quantifying Surface-Accessible Quaternary Charge for Surface Modified Coatings via Streaming Potential Measurements, *Langmuir* 2010, 26, 9032.

(6) Chakrabarty, S.; King, A.; Kurt, P.; Zhang, W.; Ohman, D. E.; Wood, L. F.; Lovelace, C.; Rao, R.; Wynne, K. J. Highly Effective, Water-Soluble, Hemocompatible 1,3-Propylene Oxide-Based Antimicrobials: Poly[(3,3-quaternary/PEG)-copolyoxetanes], *Biomacromolecules* 2011, ACS ASAP.

(7) Zhang, W.; Zheng, Y.; Orsini, L.; Morelli, A.; Galli, G.; Chiellini, E.; Carpenter, E. E.; Wynne, K. J. More Fluorous Surface Modifier Makes it Less Oleophobic: Fluorinated Siloxane Copolymer/PDMS Coatings, *Langmuir* 2010, 26, 5848.

(8) Inagi, S.; Ogoshi, T.; Miyake, J.; Bertolucci, M.; Fujiwara, T.; Galli, G.; Chiellini, E.; Chujo, Y.; Wynne, K. J. Appearing, disappearing, and reappearing fumed silica nanoparticles: Tapping-mode AFM evidence in a condensation cured polydimethylsiloxane hybrid elastomer, *Chem. Mater.* 2007, 19, 2141.

(9) Chakrabarty, S.; Zhang, X. J.; Bharti, P.; Chujo, Y.; Miyake, J.; Wynne, K. J.; Yadavalli, V. K. Processing dependence of surface morphology in condensation cured PDMS nanocomposites, *Polymer* 2010, 51, 5756.

(10) Mateo, J. N.; Kulkarni, S. S.; Das, L.; Bandyopadhyay, S.; Tepper, G. C.; Wynne, K. J.; Bandyopadhyay, S. Wetting behavior of polymer coated nanoporous anodic alumina films: transition from super-hydrophilicity to super-hydrophobicity, *Nanotechnology* 2011, 22.

(11) Chakravorty, A.; Wynne, K. J. In *AIChE National Meeting* Salt Lake City, Utah, 2010.

(12) Zhang, W.; Henke, D.; Presnall, D.; Wynne, K. J. In *AIChE* Minneapolis, Minn., 2011.

(13) King, A.; Presnall, D.; Steely, L. B.; Singh, A.; Allcock, H. R.; Wynne, K. J. in preparation.

(14) Ratner, B. D.; Yoon, S. C.; Kaul, A.; Rahman, R. In *Polyurethanes in biomedical engineering II*; Planck, H., Syre, I., Dauner, M., Egbers, G., Eds.; Elsevier: New York, 1986; Vol. 3, p 213.

(15) Andrade, J. D.; Smith, L. M.; Gregonis, D. E. *Surface and Interfacial Aspects of Biomedical Polymers*; Plenum Press: New York, 1985; Vol. 1.

(16) Andrade, J. D.; Tingey, K. G. Probing surface microheterogeniety of polyetherurethanes in an aqueous environment, *Langmuir* 1991, 7, 2471.

(17) Grasel, T. G.; Cooper, S. L. Surface properties and blood compatibility of polyurethaneureas, *Biomaterials* 1986, 7, 315.

(18) Ratner, B. D.; Cooper, S. L.; Castner, D. G.; Grasel, T. G. Characterization of alkyl grafted polyurethane block copolymers by variable takeoff angle x-ray photoelectron spectroscopy., *J Biomed Mater Res* 1990, 24, 605.

(19) Garrett, J. T.; Runt, J.; Lin, J. S. Microphase separation of segmented poly(urethane urea) block copolymers, *Macromolecules* 2000, 33, 6353.

(20) Garrett, J. T.; Siedlecki, C. A.; Runt, J. Microdomain morphology of poly(urethane urea) multiblock copolymers, *Macromolecules* 2001, 34, 7066.

(21) Sheiko, S. S.; Sumerlin, B. S.; Matyjaszewski, K. Cylindrical molecular brushes: Synthesis, characterization, and properties, *Prog. Polym. Sci.* 2008, 33, 759.

(22) Yamamoto, S.; Pietrasik, J.; Matyjaszewski, K. Temperature- and pH-responsive dense copolymer brushes prepared by ATRP, *Macromolecules* 2008, 41, 7013.

(23) Makal, U.; Uilk, J.; Kurt, P.; Cooke, R. S.; Wynne, K. J. Ring opening polymerization of 3-semifluoro- and 3-bromomethyloxetanes to poly(2,2-substituted-1,3-propylene oxide) telechelics for soft blocks in polyurethanes, *Polymer* 2005, 46, 2522.

(24) Worley, S. D.; Sun, G. Biocidal polymers, *Trends Polym. Sci.* 1996, 4, 364.

(25) Liang, J.; Chen, Y.; Barnes, K.; Wu, R.; Worley, S. D.; Huang, T. S. N-halamine/quat siloxane copolymers for use in biocidal coatings, *Biomaterials* 2006, 27, 2495.

(26) Lin, J.; Winkelmann, C.; Worley, S. D.; Kim, J. H.; Wei, C. I.; Cho, U. C.; Broughton, R. M.; Santiago, J. I.; Williams, J. F. Biocidal polyester, *J. Appl. Polym. Sci.* 2002, 85, 177.

(27) Makal, U.; Wynne, K. J. Water Induced Hydrophobic Surface, *Langmuir* 2005, 21, 3742.

(28) Grunzinger, S. J.; Wynne, K. J. Polyurethanes from Novel 1,3-Propyleneoxide Co-telechelics Having Pendant Hydantoin and Methoxymethyl Groups., *Polymer* 2006, 47, 4230.

(29) Grunzinger, S. J.; Kurt, P.; Brunson, K. M.; Wood, L.; Ohman, D. E.; Wynne, K. J. Biocidal activity of hydantoin-containing polyurethane polymeric surface modifiers, *Polymer* 2007, 48, 4653.

(30) Fujiwara, T.; Wynne, K. J. Contrasting nanoscale surface morphologies of polyurethanes containing polyoxetane soft blocks with random and block segmer sequences, *Macromolecules* 2004, 37, 8491.

(31) Zhang, W.; Fujiwara, T.; Taşkent, H.; Zheng, Y.; Brunson, K.; Wynne, K. J. Contrasting surface morphology of polyurethanes containing copolyoxetane soft blocks, *Polymer Preprints* 2009, 50, 145.

(32) Zhang, W.; Fujiwara, T.; Taşkent, H.; Zheng, Y.; Brunson, K.; Gamble, L.; Wynne, K. J. A Surface Modifier Polyurethane Having Copolyoxetane Soft Blocks with Trifluoroethoxymethyl and Polyethylene Oxide Side Chains: Contrasting Amphiphilic and Contraphilic Sur-

(33) Isquith, A. J.; McCollum, C. J. Surface Kinetic Test Method for Determining Rate of Kill by an Anti-Microbial Solid, *Appl. Environ. Microbiol.* 1978, 36, 700.

(34) Tiller, J. C.; Liao, C. J.; Lewis, K.; Klibanov, A. M. Designing surfaces that kill bacteria on contact, *Proc. Natl. Acad. Sci. U.S.A* 2001, 98, 5981.

(35) Murata, H.; Koepsel, R. R.; Matyjaszewski, K.; Russell, A. J. Permanent, non-leaching antibacterial surfaces-2: How high density cationic surfaces kill bacterial cells, *Biomaterials* 2007, 28, 4870.

(36) Majumdar, P.; Lee, E.; Patel, N.; Ward, K.; Stafslien, S. J.; Daniels, J.; Chisholm, B. J.; Boudjouk, P.; Callow, M. E.; Callow, J. A.; Thompson, S. E. M. Combinatorial materials research applied to the development of new surface coatings IX: An investigation of novel antifouling/fouling-release coatings containing quaternary ammonium salt groups, *Biofouling* 2008, 24, 185.

(37) Pant, R. R.; Buckley, J. L.; Fulmer, P. A.; Wynne, J. H.; McCluskey, D. M.; Phillips, J. P. Hybrid Siloxane Epoxy Coatings Containing Quaternary Ammonium Moieties, *J. Appl. Polym. Sci.* 2008, 110, 3080.

(38) Majumdar, P.; He, J.; Lee, E.; Kallam, A.; Gubbins, N.; Stafslien, S. J.; Daniels, J.; Chisholm, B. J. Antimicrobial activity of polysiloxane coatings containing quaternary ammonium-functionalized polyhedral oligomeric silsesquioxane, *J. Coat. Technol. Res.* 2010, 7, 455.

(39) Ye, S. J.; Majumdar, P.; Chisholm, B.; Stafslien, S.; Chen, Z. Antifouling and Antimicrobial Mechanism of Tethered Quaternary Ammonium Salts in a Cross-linked Poly(dimethylsiloxane) Matrix Studied Using Sum Frequency Generation Vibrational Spectroscopy, *Langmuir* 2010, 26, 16455.

(40) Milovic, N. M.; Wang, J.; Lewis, K.; Klibanov, A. M. Immobilized N-alkylated polyethylenimine avidly kills bacteria by rupturing cell membranes with no resistance developed, *Biotechnol. Bioeng.* 2005, 90, 715.

(41) Huang, J. Y.; Koepsel, R. R.; Murata, H.; Wu, W.; Lee, S. B.; Kowalewski, T.; Russell, A. J.; Matyjaszewski, K. Nonleaching antibacterial glass surfaces via "Grafting Onto": The effect of the number of quaternary ammonium groups on biocidal activity, *Langmuir* 2008, 24, 6785.

(42) Jeong, E. H.; Yang, H.; Youk, J. H. Preparation of polyurethane cationomer nanofiber mats for use in antimicrobial nanofilter applications, *Mater. Lett.* 2007, 61, 3991.

(43) Kurt, P.; Wood, L.; Ohman, D. E.; Wynne, K. J. Highly Effective Contact Antimicrobial Surfaces via Polymer Surface Modifiers, *Langmuir* 2007, 23, 4719.

(44) Brunson, K., Virginia Commonwealth University, 2010.

(45) Goddard, J. M.; Hotchkiss, J. H. Polymer surface modification for the attachment of bioactive compounds, *Prog. Polym. Sci.* 2007, 32, 698.

(46) Kugler, R.; Bouloussa, O.; Rondelez, F. Evidence of a charge-density threshold for optimum efficiency of biocidal cationic surfaces, *Microbiology-SGM* 2005, 151, 1341.

(47) Ledbetter, J. W., Jr.; Bowen, J. R. Spectrophotometric determination of the critical micelle concentration of some alkyldimethylbenzylammonium chlorides using fluorescein, *Anal. Chem.* 1969, 41, 1345.

(48) Stanley, J. S. The Effect of Paraffin Chain Salts on the Charge on Textile Fibers, *J. Phys. Chem.* 1954, 58, 533.

(49) Adamczyk, Z.; Zembala, M.; Warszynski, P.; Jachimska, B. Characterization of polyelectrolyte multilayers by the streaming potential method, *Langmuir* 2004, 20, 10517.

(50) Lichter, J. A.; Rubner, M. F. Polyelectrolyte Multilayers with Intrinsic Antimicrobial Functionality: The Importance of Mobile Polycations, *Langmuir* 2009, 25, 7686.

(51) Pu, Q. S.; Elazazy, M. S.; Alvarez, J. C. Label-free detection of heparin, streptavidin, and other probes by pulsed streaming potentials in plastic microfluidic channels, *Anal. Chem.* 2008, 80, 6532.

(52) Brunson, K. M. Thesis, Virginia Commonwealth University, 2006.

(53) Lamba, N. M. K.; Woodhouse, K. A.; Cooper, S. L. *Polyurethanes in Biomedical Applications*; CRC Press: Boca Raton, Fla., 1998.

(54) Cooper, S. L., Seymour R. W. Thermal analysis of polyurethane block polymers, *Macromolecules* 1973, 6, 48.

(55) Wang, C. B.; Cooper, S. L. Morphology and Properties of Segmented Polyether Polyurethaneureas, *Macromolecules* 1983, 16, 775.

(56) Kirby, B. J.; Ernest F. Hasselbrink, J. Zeta potential of microfluidic substrates: 2. Data for polymers, *Electrophoresis* 2004, 25, 203.

(57) Grapski, J. A.; Cooper, S. L. Synthesis and characterization of non-leaching biocidal polyurethanes, *Biomaterials* 2001, 22, 2239.

(58) Klibanov, A. M. Permanently microbicidal materials coatings, *J. Mater. Chem.* 2007, 17, 2479.

(59) Ellison, A. H.; Fox, H. W.; Zisman, W. A. Wetting of fluorinated solids by hydrogen-bonding liquids, *J. Phys. Chem.* 1953, 57, 622.

(60) Yang, S.; Wang, J. G.; Ogino, K.; Valiyaveettil, S.; Ober, C. K. Low-surface-energy fluoromethacrylate block copolymers with patternable elements, *Chem. Mater.* 2000, 12, 33.

(61) Kurt, P.; Wynne, K. J. Synthesis and characterization of polyurethanes containing 2,2-substituted-1,3-propylene oxide soft blocks having —$CF_3$ and —$CF_2H$ terminated side chains, *Polymer Preprints* 2005, 46, 649.

(62) Kurt, P.; Chakravorty, A.; Wynne, K. J. Unusual contact angle hysteresis for polyurethanes with copolyoxetane soft blocks having —$CF_2H$ terminal side chains in preparation.

(63) Wynne, K. J.; Kurt, P.; Ohman, D.; Rao, R.; Chakrabarty, S.; Mullins, A. U. S., 2011.

(64) Ong, M. D.; Volksen, W.; Dubois, G.; Lee, V.; Brock, P. J.; Deline, V. R.; Miller, R. D.; Dauskardt, R. H. Molecular-controlled fracture and release of templated nanoporous organosilicate thin films, *Adv. Mater.* (*Weinheim, Ger.*) 2008, 20, 3159.

(65) Ro, H. W.; Char, K.; Jeon, E. C.; Kim, H. J.; Kwon, D.; Lee, H. J.; Lee, J. K.; Rhee, H. W.; Soles, C. L.; Yoon, D. Y. High-modulus spin-on organosilicate glasses for nanoporous applications, *Adv. Mater.* (*Weinheim, Ger.*) 2007, 19, 705.

(66) Makal, U.; Fujiwara, T.; Cooke, R. S.; Wynne, K. J. Polyurethanes containing oxetane-derived poly(2,2-substituted-1,3-propylene oxide) soft blocks: copolymer effect on wetting behavior, *Langmuir* 2005, 21, 10749

(67) Saegusa, T.; Chujo, Y. An Organic Inorganic Hybrid Polymer, *Journal of Macromolecular Science-Chemistry* 1990, A27, 1603.

(68) Meuler, A. J.; Smith, J. D.; Varanasi, K. K.; Mabry, J. M.; McKiney, G. H.; Cohen, R. E. Relationships between Water Wettability and Ice Adhesion, *ACS Appl. Mater. Interfaces* 2010, 2, 3100.

(69) Kendall, K. The adhesion and surface energy of elastic solids, *J. Physics D Applied Physics* 1971,4, 1186.

(70) Newby, B. M. Z.; Chaudhury, M. K.; Brown, H. R. Macroscopic evidence of the effect of interfacial slippage on adhesion, *Science* 1995, 269, 1407.

(71) Kendall, K. Adhesion: molecules and mechanics, *Science* 1994, 263, 1720.

(72) Zhang, W.; Xu, L.; Wynne, K. J. 2011, manuscript in preparation "Modeling a test for abhesion of a soft coating".

(73) Katano, Y.; Tomono, H.; Nakajima, T. Surface property of polymer films with fluoroalkyl side chains, *Macromolecules* 1994, 27, 2342.

(74) Bertolucci, M.; Galli, G.; Chiellini, E.; Wynne, K. J. Wetting Behavior of Films of New Fluorinated Styrene-Siloxane Block Copolymers, *Macromolecules* 2004, 37, 3666

(75) Harada, K.; Koizumi, A.; Saito, N.; Inoue, K.; Yoshinaga, T.; Date, C.; Fujii, S.; Hachiya, N.; Hirosawa, I.; Koda, S.; Kusaka, Y.; Murata, K.; Omae, K.; Shimbo, S.; Takenaka, K.; Takeshita, T.; Todoriki, H.; Wada, Y.; Watanabe, T.; Ikeda, M. Historical and geographical aspects of the increasing perfluorooctanoate and perfluorooctane sulfonate contamination in human serum in Japan, *Chemosphere* 2007, 66, 293.

(76) http://www.epa.gov/opptintr/pfoa/pubs/pfoarisk.html; US Envronmental Protection Agency: 2010.

(77) Chakrabarty, S.; Wynne, K. J. Polydimethylsiloxane-fluorous polyoxetane urethane/urea linked triblock block copolymers: condensation cure to tough elastomers with PDMS surface properties., manuscript in preparation.

(78) Lee, J. N.; Park, C.; Whitesides, G. M. Solvent compatibility of poly(dimethylsiloxane)-based microfluidic devices, *Anal. Chem.* 2003, 75, 6544.

(79) Burgmann, S.; Grosse, S.; Schroder, W.; Roggenkamp, J.; Jansen, S.; Graf, F.; Busen, M. A refractive index-matched facility for fluid-structure interaction studies of pulsatile and oscillating flow in elastic vessels of adjustable compliance, *Experiments in Fluids* 2009, 47, 865.

(80) Johnston, E.; Bullock, S.; Uilk, J.; Gatenholm, P.; Wynne, K. J. Networks from alpha,omega-dihydroxypoly (dimethylsiloxane) and (tridecafluoro-1,1,2,2-tetrahydrooctyl)triethoxysilane: Surface microstructures and surface characterization, *Macromolecules* 1999, 32, 8173.

(81) Wynne, K. J.; Fujiwara, T.; Ogoshi, T.; Chujo, Y.; Bertolucci, M.; Galli, G.; Chellini, E. TM-AFM on condensation cured PDMS with fumed silica: "The Case of the Disappearing Filler!" *Polymer Preprints* 2004, 45, 628.

(82) Decher, G.; Hong, J. D. Buildup of Ultrathin Multilayer Films by a Self-Assembly Process. 1. Consecutive Adsorption of Anionic and Cationic Bipolar Amphiphiles on Charged Surfaces, *Makromolekulare Chemie-Macromolecular Symposia* 1991, 46, 321.

(83) Decher, G.; Schmitt, J. Fine-tuning of the film thickness of ultrathin multilayer films composed of consecutively alternating layers of anionic and cationic polyelectrolytes, *Prog. Colloid Polym. Sci.* 1992, 89, 160.

(84) Jaber, J. A.; Schlenoff, J. B. Counterions and water in polyelectrolyte multilayers: A tale of two polycations, *Langmuir* 2007, 23, 896.

(85) Jisr, R. M.; Rmaile, H. H.; Schlenoff, J. B. Hydrophobic and ultrahydrophobic multilayer thin films from perfluorinated polyelectrolytes, *Angewandte Chemie-International Edition* 2005, 44, 782.

(86) Perez, E.; Gomez, M. A.; Bello, A.; Fatou, J. G. Crystallization behavior of polyoxetanes: polyoxetane, poly(3,3-dimethyloxetane) and poly(3,3-diethyloxetane), *Colloid Polym. Sci.* 1983, 261, 571.

(87) Henderson, G. V. S., Jr.; Hardenstine, K. E.; Murphy, C. J.; Sperling, L. H.; Manser, G. E. Crystallization behavior and crystal structure of novel polyoxetanes, *Polym. Mater. Sci. Eng.* 1985, 53, 801.

(88) Hardenstine, K. E.; Henderson, G. V. S.; Sperling, L. H.; Murphy, C. J.; Manser, G. E. Crystallization Behavior of Poly(3,3-Bisethoxymethyl Oxetane) and Poly(3,3-Bisazidomethyl Oxetane), *J. Polym. Sci. Pt. B-Polym. Phys.* 1985, 23, 1597.

(89) Malik, A. A.; Archibald, T. G.; Aerojet General Corp., USA: US, 1998, p 32 pp

(90) Malik, A. A.; Archibald, T. G.; Carlson, R. P.; Wynne, K. J.; Kresge, E. N.; USPTO, Ed.; AMPAC Fine Chemicals LLC: US, 2006.

(91) Jiang, W.-C.; Huang, Y.; Gu, G.-T.; Meng, W.-D.; Qing, F.-L. A novel waterborne polyurethane containing short fluoroalkyl chains: Synthesis, characterization and its application on cotton fabrics surface, *Appl. Surf Sci.* 2006, 253, 2304.

(92) Zheng, Y.; Wynne, K. J. Poly(bis-2,2,2-trifluoroethoxymethyl oxetane): Enhanced Surface Hydrophobicity by Crystallization and Spontaneous Asperity Formation *Langmuir* 2007, 23, 11964.

(93) Williamson, A. W. Theory of Aetherification, *Philos. Mag.* 1850, 37, 350.

The invention claimed is:

1. A compound having the formula:

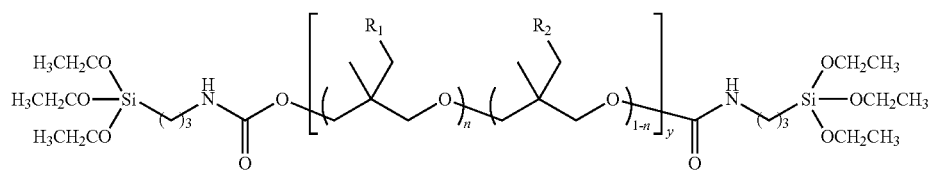

wherein n is 0 to 1;

wherein y is an integer of 1-1000; and wherein $R_1$ and $R_2$ are not identical and are each independently $-OCH_2CF_2H$, $-OCH_2CF_2CF_2H$, $-OCH_2CF_2CF_2CF_2H$, $-Br$, $-(OC_2H_4)_x-O-CH_3$, wherein x is 0-11, alkoxy, $-CF_2H$-terminated-fluoroalkoxy, alkoxycycloalkyl, or a group having one of the following formulas:

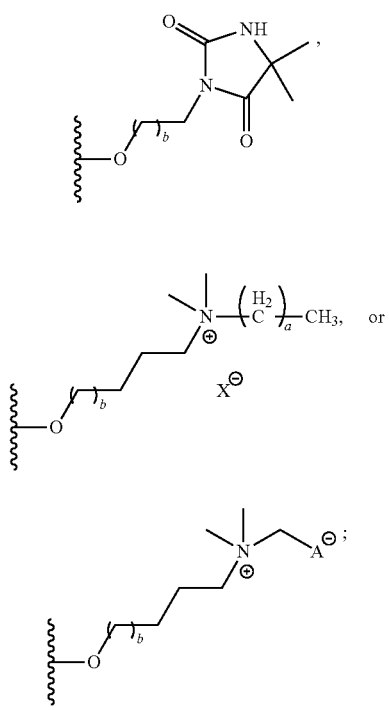

wherein a is 5-15;
wherein b is 0-5
wherein X is Cl, Br, I, OH, or NO₃; and
wherein A is —CO₂ or —SO₃.

2. The compound of claim 1, having one of the following formulas:

3. A composition, comprising a polymerization product of:
(A) the compound of claim 1;
(B) one or more bis(trialkoxysilyl)alkanes having the formula:

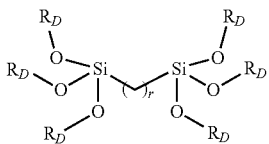

wherein $R_D$ is —CH₃, —CH₂CH₃, —CH₂CH₂CH₃, or —CH₂CH₂CH₂CH₃; and wherein r is an integer of 1-10;

or one or more polydialkoxysiloxanes having the formula:

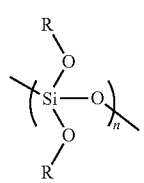

where R is —CH₃ or —C₂H₅;
(C) one or more of an isocyanate, diisocyanate, or combination thereof;
(D) optionally, a diol or diamine chain extender; and
(E) optionally, a soft block diol selected from the group consisting of polydimethylsiloxane diol, polytetram-

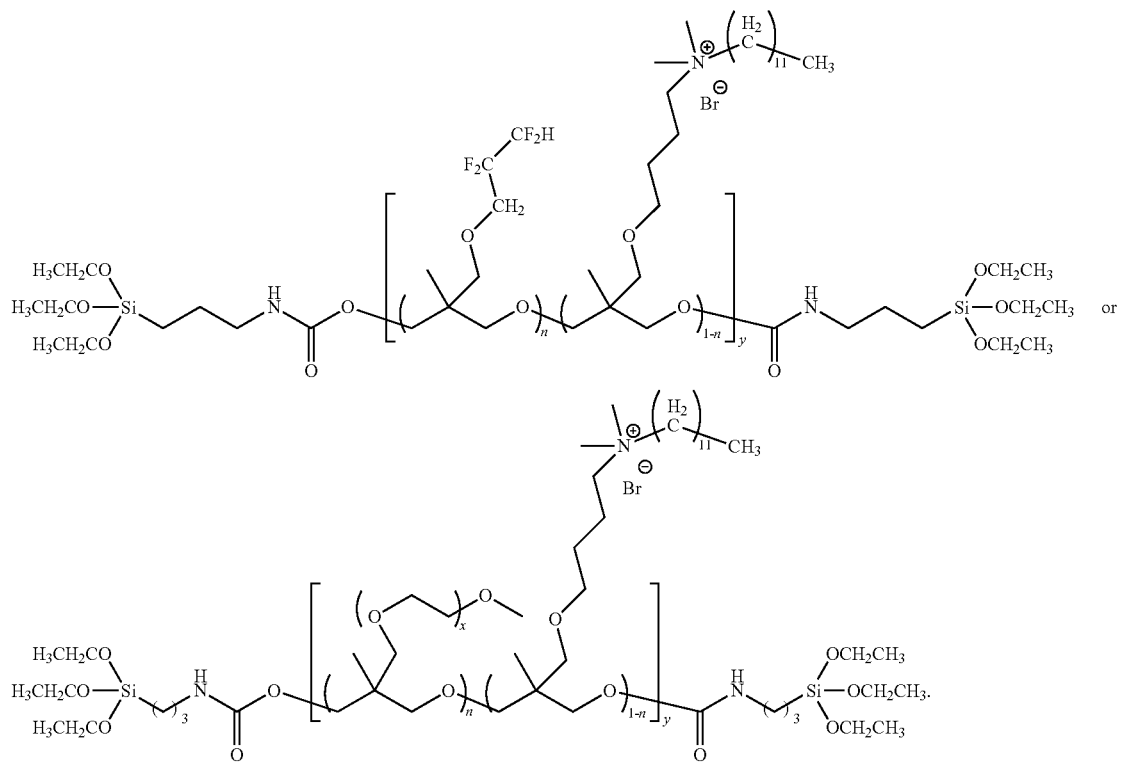

ethylene oxide diol, polypropylene oxide diol, polyethylene oxide diol, or a combination of two or more thereof.

4. The composition of claim 3, wherein (B) is a bis(trialkoxysilyl)alkane having the formula:

$$\text{(H}_3\text{CH}_2\text{CO)}_2\text{Si(OCH}_2\text{CH}_3\text{)-CH}_2\text{CH}_2\text{-Si(OCH}_2\text{CH}_3\text{)}_2\text{(OCH}_2\text{CH}_3\text{)}$$

5. A composition, comprising:
(a) a reaction product of:
(A) the compound of claim 1; and
(B) one or more bis(trialkoxysilyl)alkanes having the formula:

$$(R_DO)_3Si-(CH_2)_r-Si(OR_D)_3$$

wherein $R_D$ is —CH$_3$, —CH$_2$CH$_3$, —CH$_2$CH$_2$CH$_3$, or —CH$_2$CH$_2$CH$_2$CH$_3$; and wherein r is an integer of 1-10;
or one or more polydialkoxysiloxanes having the formula:

$$[Si(OR)_2-O]_n$$

where R is —CH$_3$ or —C$_2$H$_5$;
and
(b) a polymerization product of:
(C) one or more of an isocyanate, diisocyanate, or combination thereof;
(D) optionally, a diol or diamine chain extender; and
(E) optionally, a soft block diol selected from the group consisting of polydimethylsiloxane diol, polytetramethlene oxide diol, polypropylene oxide diol, polyethylene oxide diol, polydimethylsiloxane dipropylamine, or a combination of two or more thereof.

6. The composition of claim 5, which is a blend of (a) and (b).

7. An article or device, comprising the composition of claim 3 on a surface thereof.

8. An article or device, comprising the composition of claim 5 on a surface thereof.

9. A method for killing a microbe, comprising contacting said microbe with the composition of claim 3.

10. A method for killing a microbe, comprising contacting said microbe with the composition of claim 5.

11. The compound of claim 1, wherein $R_1$ and $R_2$ are not identical and are each independently —OCH$_2$CF$_2$H, —OCH$_2$CF$_2$CF$_2$H, —OCH$_2$CF$_2$CF$_2$CF$_2$H, —Br, —(OC$_2$H$_4$)x-O—CH$_3$, wherein x is 0-11, —CF$_2$H-terminated-fluoroalkoxy, or a group having one of the following formulas:

[hydantoin structure with —O—(CH$_2$)$_b$— linker]

[quaternary ammonium structure —O—(CH$_2$)$_b$—N$^+$(CH$_3$)$_2$—(CH$_2$)$_a$—CH$_3$, X$^-$], or

[quaternary ammonium structure —O—(CH$_2$)$_b$—N$^+$(CH$_3$)$_2$—CH$_2$, A$^-$]

12. The compound of claim 1, wherein $R_1$ and $R_2$ are not identical and at least one is —OCH$_2$CF$_2$H, —OCH$_2$CF$_2$CF$_2$H, —OCH$_2$CF$_2$CF$_2$CF$_2$H, —Br, —(OC$_2$H$_4$)$_x$—O—CH$_3$, wherein x is 0-11, or —CF$_2$H-terminated-fluoroalkoxy.

13. The compound of claim 1, wherein $R_1$ and $R_2$ are not identical and at least one is —OCH$_2$CF$_2$H, —OCH$_2$CF$_2$CF$_2$H, —OCH$_2$CF$_2$CF$_2$CF$_2$H, —(OC$_2$H$_4$)$_x$—O—CH$_3$, wherein x is 0-11, or —CF$_2$H-terminated-fluoroalkoxy.

14. The compound of claim 1, wherein $R_1$ and $R_2$ are not identical and at least one is a group having one of the following formulas:

[hydantoin structure with —O—(CH$_2$)$_b$— linker]

[quaternary ammonium structure —O—(CH$_2$)$_b$—N$^+$(CH$_3$)$_2$—(CH$_2$)$_a$—CH$_3$, X$^-$], or -continued

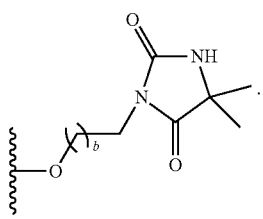

15. The compound of claim 1, wherein $R_1$ and $R_2$ are not identical and at least one is a group having the following formula:

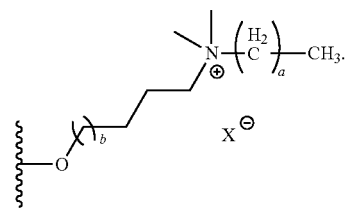

16. The compound of claim 1, wherein $R_1$ and $R_2$ are not identical and at least one is a group having the following formula:

17. The compound of claim 1, wherein $R_1$ and $R_2$ are not identical and at least one is a group having the following formula:

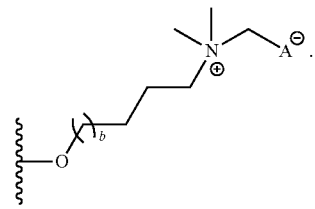

18. The compound of claim 1, having the following formula:

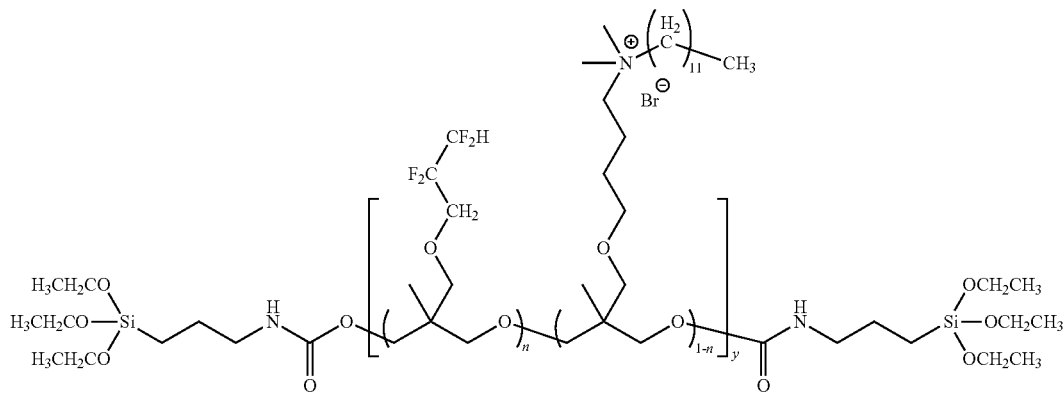

19. The compound of claim 1, having the following formula:

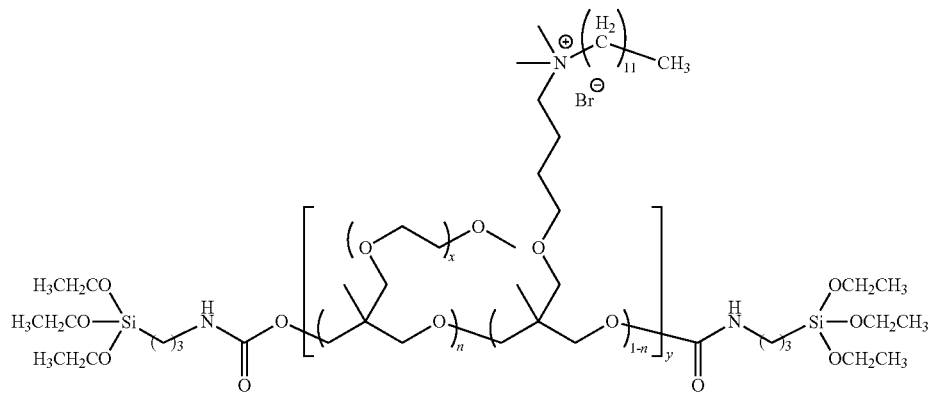

20. A method, comprising:

reacting a compound having the formula:

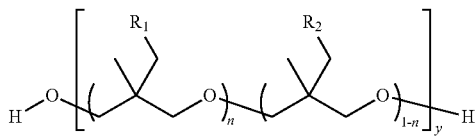

wherein n is 0 to 1;

wherein y is an integer of 1-1000; and wherein $R_1$ and $R_2$ are not identical and are each independently —$OCH_2CF_2H$, —$OCH_2CF_2CF_2H$, —$OCH_2CF_2CF_2CF_2H$, —Br, —$(OC_2H_4)_x$—O—$CH_3$, wherein x is 0-11, alkoxy, —$CF_2H$-terminated-fluoroalkoxy, alkoxycycloalkyl, or a group having one of the following formulas:

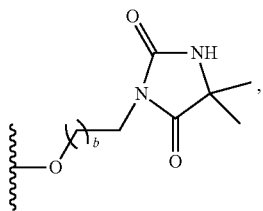

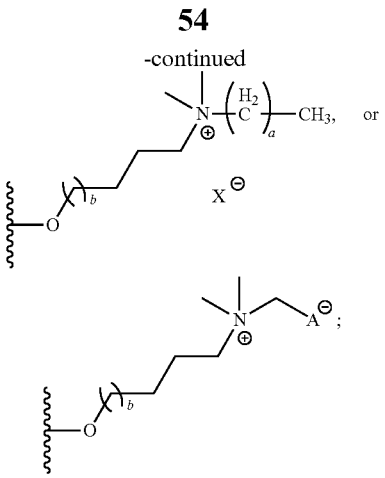

wherein a is 5-15;

wherein b is 0-5 wherein X is Cl, Br, I, OH, or $NO_3$; and wherein A is —$CO_2$ or —$SO_3$;

with one or more isocyanates having the formula:

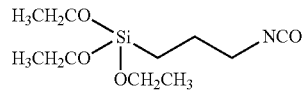

to produce the compound of claim 1.

* * * * *